United States Patent
Swift et al.

(10) Patent No.: US 9,351,855 B2
(45) Date of Patent: *May 31, 2016

(54) POWERED LOWER EXTREMITY ORTHOTIC AND METHOD OF OPERATION

(75) Inventors: Tim Swift, Albany, CA (US); Adam Brian Zoss, Berkeley, CA (US); Katherine Strausser, Berkeley, CA (US); Matthew Rosa, San Francisco, CA (US); Homayoon Kazerooni, Berkeley, CA (US); Dylan Miller Fairbanks, Guangzhou (CN); Minerva Vasudevan Pillai, Pleasant Hill, CA (US); Miclas Schwartz, Goettingen (DE); Bram Gilbert Antoon Lambrecht, Sunnyvale, CA (US); Sebastian Kruse, Berkeley, CA (US)

(73) Assignees: Ekso Bionics, Inc., Richmond, CA (US); The Regents of the University of California, Oakland, CA (US)

( * ) Notice: Subject to any disclaimer, the term of this patent is extended or adjusted under 35 U.S.C. 154(b) by 639 days.

This patent is subject to a terminal disclaimer.

(21) Appl. No.: 13/480,160

(22) Filed: May 24, 2012
(Under 37 CFR 1.47)

(65) Prior Publication Data
US 2013/0150980 A1 Jun. 13, 2013

Related U.S. Application Data

(63) Continuation-in-part of application No. 12/457,573, filed on Jun. 16, 2009, now Pat. No. 8,231,688.

(60) Provisional application No. 61/132,217, filed on Jun. 16, 2008, provisional application No. 61/136,535, filed on Sep. 12, 2008.

(51) Int. Cl.
A61F 5/00 (2006.01)
A61F 2/68 (2006.01)
(Continued)

(52) U.S. Cl.
CPC ... *A61F 2/68* (2013.01); *A61F 2/64* (2013.01); *A61F 2/80* (2013.01);
(Continued)

(58) Field of Classification Search
CPC .............. A61F 2002/30359; A61F 2002/701; A61F 2002/704; A61F 2002/741; A61F 2002/744; A61F 2002/745; A61F 2002/748; A61F 2002/7625; A61F 2002/7635; A61F 2002/7645; A61F 2220/0033; A61F 2/64
USPC ........ 602/16, 20–28; 5/624; 128/882; 623/24
See application file for complete search history.

(56) References Cited

U.S. PATENT DOCUMENTS

| 2,010,482 A | 8/1935 | Cobb |
| 2,305,291 A | 12/1942 | Filippi |

(Continued)

FOREIGN PATENT DOCUMENTS

| WO | 2007/016781 | 2/2007 |
| WO | 2007/025116 | 3/2007 |
| WO | WO 2007/103579 | 9/2007 |

OTHER PUBLICATIONS

Riener et al., "Stair Ascent and Descent at Different Inclinations", Gait and Posture, No. 15, pp. 32-44, 2002.

(Continued)

*Primary Examiner* — Michael Brown
(74) *Attorney, Agent, or Firm* — Diederiks & Whitelaw, PLC

(57) ABSTRACT

A powered lower extremity orthotic, including a shank link coupled to an artificial foot, a knee mechanism connected to the shank link and a thigh link, is controlled by based on signals from various orthotic mounted sensors such that the artificial foot follows a predetermined trajectory defined by at least one Cartesian coordinate.

20 Claims, 40 Drawing Sheets

(51) Int. Cl.
| | |
|---|---|
| *A61F 2/64* | (2006.01) |
| *A61F 2/80* | (2006.01) |
| *A61F 2/30* | (2006.01) |
| *A61F 2/70* | (2006.01) |
| *A61F 2/74* | (2006.01) |
| *A61F 2/76* | (2006.01) |

(52) U.S. Cl.
CPC ...... *A61F 2002/30359* (2013.01); *A61F 2002/701* (2013.01); *A61F 2002/704* (2013.01); *A61F 2002/741* (2013.01); *A61F 2002/744* (2013.01); *A61F 2002/745* (2013.01); *A61F 2002/748* (2013.01); *A61F 2002/7625* (2013.01); *A61F 2002/7635* (2013.01); *A61F 2002/7645* (2013.01); *A61F 2220/0033* (2013.01)

(56) References Cited

U.S. PATENT DOCUMENTS

| | | | |
|---|---|---|---|
| 2,573,866 A | 11/1951 | Murphy | |
| 3,863,274 A | 2/1975 | Glabiszewski | |
| 4,557,257 A | 12/1985 | Fernandez et al. | |
| 4,647,004 A | 3/1987 | Bihlmaier | |
| 4,872,665 A | 10/1989 | Chareire | |
| 4,964,628 A | 10/1990 | Poplawski | |
| 5,020,790 A | 6/1991 | Beard et al. | |
| 5,062,856 A | 11/1991 | Sawamura et al. | |
| 5,282,460 A | 2/1994 | Boldt | |
| 5,344,446 A | 9/1994 | Sawamura et al. | |
| 5,383,939 A | 1/1995 | James | |
| 5,405,409 A | 4/1995 | Knoth | |
| 5,443,521 A | 8/1995 | Knoth et al. | |
| 5,476,441 A | 12/1995 | Durfee et al. | |
| 5,571,205 A | 11/1996 | James | |
| 5,658,242 A | 8/1997 | McKay et al. | |
| 5,662,693 A | 9/1997 | Johnson et al. | |
| 5,704,945 A | 1/1998 | Wagner et al. | |
| 5,755,813 A | 5/1998 | Krukenberg | |
| 5,888,212 A | 3/1999 | Petrofsky et al. | |
| 5,893,891 A | 4/1999 | Zahedi | |
| 5,899,869 A | 5/1999 | Barrack, Jr. et al. | |
| 5,961,476 A | 10/1999 | Betto et al. | |
| 6,113,642 A | 9/2000 | Petrofsky et al. | |
| 6,500,210 B1 | 12/2002 | Sabolich et al. | |
| 6,517,585 B1 | 2/2003 | Zahedi et al. | |
| 6,610,101 B2 | 8/2003 | Herr et al. | |
| 6,676,707 B2 | 1/2004 | Yih et al. | |
| 6,719,806 B1 | 4/2004 | Zahedi et al. | |
| 6,755,870 B1 | 6/2004 | Biedermann et al. | |
| 6,764,520 B2 | 7/2004 | Deffenbaugh et al. | |
| 6,821,233 B1 | 11/2004 | Colombo et al. | |
| 6,966,882 B2 | 11/2005 | Horst | |
| 7,048,707 B2 | 5/2006 | Schwenn et al. | |
| 7,135,003 B2 | 11/2006 | Dariush | |
| 7,153,242 B2 | 12/2006 | Goffer | |
| 7,190,141 B1 | 3/2007 | Ashrafiuon et al. | |
| 7,198,071 B2 | 4/2007 | Bisbee, III et al. | |
| 7,217,247 B2 | 5/2007 | Dariush et al. | |
| 7,279,009 B2 | 10/2007 | Herr et al. | |
| 7,313,463 B2 | 12/2007 | Herr et al. | |
| 7,314,490 B2 | 1/2008 | Bedard et al. | |
| 7,390,309 B2 | 6/2008 | Dariush | |
| 7,393,335 B2 | 7/2008 | Carvey et al. | |
| 7,404,782 B2 | 7/2008 | Kudoh et al. | |
| 7,416,538 B2 | 8/2008 | Katoh et al. | |
| 7,485,152 B2 | 2/2009 | Haynes et al. | |
| 7,524,297 B2 | 4/2009 | Shimada et al. | |
| 7,537,573 B2 | 5/2009 | Horst | |
| 7,628,766 B1 | 12/2009 | Kazerooni et al. | |
| 7,713,217 B2 | 5/2010 | Ikeuchi et al. | |
| 7,736,394 B2 | 6/2010 | Bedard et al. | |
| 7,747,409 B2* | 6/2010 | Ladetto et al. | 702/150 |
| 7,785,279 B2 | 8/2010 | Sankai | |
| 7,883,546 B2 | 2/2011 | Kazerooni et al. | |
| 7,942,935 B2 | 5/2011 | Iversen et al. | |
| 7,947,004 B2 | 5/2011 | Kazerooni et al. | |
| 8,057,410 B2 | 11/2011 | Angold et al. | |
| 8,147,436 B2* | 4/2012 | Agrawal et al. | 602/16 |
| 8,231,688 B2* | 7/2012 | Fairbanks et al. | 623/27 |
| 2004/0116839 A1 | 6/2004 | Sarkodic-Gyan | |
| 2006/0249315 A1 | 11/2006 | Herr et al. | |
| 2006/0293761 A1 | 12/2006 | Baumann et al. | |
| 2007/0043449 A1 | 2/2007 | Herr et al. | |
| 2007/0123997 A1 | 5/2007 | Herr et al. | |
| 2007/0162152 A1 | 7/2007 | Herr et al. | |
| 2008/0009771 A1 | 1/2008 | Perry et al. | |
| 2008/0154165 A1 | 6/2008 | Ashihara et al. | |
| 2009/0292369 A1 | 11/2009 | Kazerooni et al. | |
| 2010/0010641 A1 | 1/2010 | Kazerooni et al. | |
| 2010/0023133 A1* | 1/2010 | Fairbanks et al. | 623/24 |
| 2010/0094185 A1 | 4/2010 | Amundson et al. | |
| 2010/0204627 A1 | 8/2010 | Kazerooni et al. | |
| 2011/0166489 A1* | 7/2011 | Angold et al. | 601/34 |

OTHER PUBLICATIONS

Au et al., "Powered Ankle-Foot Prosthesis for the Improvement of Amputee Ambulation", Proc. of the 29$^{th}$ Annual International Conf. of the IEEE EMBS, Lyon, France, pp. 3020-3026, 2007.

Lambrecht, "Design of a Hybrid Passive-Active Prosthesis for Above-Knee Amputees", Ph.D. Thesis, University of California at Berkeley, 2008.

Sup et al., "Design and Control of a Powered Transfemoral Prosthesis", International Journal of Robotics Research, No. 27; 263, 2008.

Lambrecht et al., "Design of a Semi-Active Knee Prosthesis", 2009 IEEE International Conference on Robotics and Automation, Kobe, JP, pp. 639-645, 2009.

Sup et al., "Design and Control of a Powered Knee and Ankle Prosthesis", 2007 IEEE International Conference on Robotics and Automation Roma, Italy, pp. 4134-4139, 2007.

Kapti et al., "Design and Control of an Active Artificial Knee Joint", Mechanism and Machine Theory, No. 41, pp. 1477-1485, 2006.

Popovic et al., "Optimal Control for an Above-Knee Prosthesis with Two Degrees of Freedom", Journal of BioMechanics, vol. 28, No. 1, pp. 89-98, 1995.

Horn, "Electro-Control: am EMG-Controlled A/K Prosthesis", Med. & Biol. Eng., vol. 10, pp. 61-73, 1972.

Bionic Technology by Ossur, "Technical Manual, Proprio Foot", 2009.

Flowers, "A Man-Interactive Simulator System", Ph.D. Thesis, Massachusetts Institute of Technology, 1972.

"Exoskeleton Prototype Project: Final Report on Phase I," (Oct. 1966). Contract No. N00014-66-C0051, Mechanical Equipment Branch, Mechanical Technology Laboratory, Research and Development Center, General Electric Company: Schenectady, New York, pp. 1-72.

"Machine Augmentation of Human Strength and Endurance: Hardiman I Prototype Project," (Jul. 1969). ONR Contract No. N00014-66-C0051, Specialty Materials Handling Products Operation, General Electric Company: Schenectady, New York, 60 pgs.

"Research and Development Prototype for Machine Augmentation of Human Strength and Endurance: Hardiman I Project," (May 1971). ONR Contract No. N00014-66-C0051, Specialty Materials Handling Products Operation, General Electric Company, Schenectady, New York, pp. 1-25.

Agrawal, A. et al. (Jul. 2005). "Design of a Two Degree-of-freedom Ankle-Foot Orthosis for Robotic Rehabilitation." *Proceedings of the 2005 IEEE 9$^{th}$ International Conference on Rehabilitation Robotics*, Chicago, Illinois, pp. 41-44.

Arroyo, P. (Dec. 1998). "Design of a Minimally Actuated Assistive Walking Device," Masters of Science Thesis submitted to the Graduate School at the University of California, Berkeley, 25 pgs.

Belforte, G. et al. (2001). "Pneumatic Active Gait Orthosis," *Mechatronics* 11:301-323.

Bharadwaj, K. et al. (Nov. 2005). "Design of a Robotic Gait Trainer using Spring Over Muscle Actuators for Ankle Stroke Rehabilitation." *Journal of Biomechanical Engineering*, vol. 127, pp. 1009-1013.

(56) References Cited

OTHER PUBLICATIONS

Chu, A. (Apr. 2003). "Design Overview of 1st Generation Exoskeleton," Master of Science Thesis submitted to the Mechanical Engineering Department at the University of California, Berkeley, pp. 1-62.

Clark, D. C. et al. (Aug. 1962). "Exploratory Investigation of the Man Amplifier Concept," Technical Documentary Report No. AMRL-TDR-62-89, Behavioral Science Laboratory, Aerospace Medical Division, Air Force Systems Command, Wright-Patterson Air Force Base: Ohio, 81 pgs.

Croshaw, P.F. (Jul. 1969). "Hardiman I Arm Test: Hardiman I Prototype Project." General Electric Company, Schenectady, New York.

Crowell, H.P. et al. (Nov. 2002). "Exoskeleton Power and Torque Requirements Based on Human Biomechanics." Army Research Laboratory, ARL-TR-2764.

Dollar, A.M. et al. (Feb. 2008). "Lower-Extremity Exoskeletons and Active Orthoses: Challenges and State of the Art." *IEEE Transactions on Robotics*, vol. 24, No. 1, pp. 144-158.

Donelan, J.M. et al. (2002). "Simultaneous Positive and Negative External Mechanical Work in Human Walking." *Journal of Biomechanics*, vol. 35, pp. 117-124.

Durfee, W.K. et al. (2004). "Preliminary Design and Simulation of a Pneumatic, Stored-energy, Hybrid Orthosis for Gait Restoration." *Proceedings of the 2004 ASME International Mechanical Engineering Congress*, Anaheim, California.

Endo, K., et al. (Oct. 2006). "A Quasi-passive Model of Human Leg Function in Level-ground Walking." *Proceedings of the 2006 IEEE/RSJ International Conference on Intelligent Robots and Systems*, Beijing, China, pp. 4935-4939.

Ferris, D. et al. (Aug. 2001). "An Ankle-foot Orthosis Powered by Artificial Muscles," *Proceedings of the 25th Annual Meeting of the American Society of Biomechanics*, 2 pgs.

Ferris, D.P. et al. (2005). "Powered Lower Limb Orthoses for Gait Rehabilitation." *Top Spinal Cord Injury Rehabilitation*, vol. 11, No. 2, pp. 34-49.

Ferris, D.P. et al. (2006). "An Improved Powered Ankle-foot Orthosis using Proportional Myelectric Control." *Gait & Posture*, vol. 23, pp. 425-428.

Gotschall, J.S. et al. (2003). "Energy Cost and Muscular Activity Required for Propulsion During Walking." *Journal of Applied Physiology*, No. 94, pp. 1766-1772.

Gregorczyk, K.N. et al. (2006). "The Effects of a Lower Body Exoskeleton Load Carriage Assistive Device on Oxygen Consumption and Kinematics During Walking with Loads." *25th Army Science Conference*, Orlando, Florida.

Griffin, T.M. et al. (Jan. 1999). "Walking in Simulated Reduced Gravity: Mechanical Energy Fluctuations and Exchange." *The Journal of Applied Physiology*, vol. 86, pp. 383-390.

Grundman, J. et al. (1987). "Computer Control of Multi-task Exoskeleton for Paraplegics." *Theory and Practice of Robots and Manipulators, Proceedings of RoManSy 1986—6th CISM-IFToMM Symposium*, The MIT Press, pp. 233-240.

Harley, J. A. (Aug. 1995). "Design and Construction of an Underactuated Assistive Walking Device," Master of Science Thesis submitted to the Graduate School at the University of California, Berkeley, pp. 1-31.

Hesse, S. et al. (Dec. 2003). "Upper and Lower Extremity Robotic Devices for Rehabilitation and for Studying Motor Control." *Current Opinion in Neurology*, vol. 16, No. 6, pp. 705-710.

Hill, J.W. (1987). "Hydraulically Powered Lower Limb Orthosis." *Theory and Practice of Robots and Manipulators, Proceedings of RoManSy 1986—6th CISM-IFToMM Symposium*, The MIT Press, pp. 182-192.

Hollander K. et al. (2006). "An Efficient Robotic Tendon for Gait Assistance." *Journal of Biomechanical Engineering*, vol. 128, No. 5, pp. 788-791.

Irby, S. et al. (Jun. 1999). "Automatic Control Design for a Dynamic Knee-Brace System," *IEEE Transactions on Rehabilitation Engineering* 7(2):135-139.

Jaukovic, N.D. (1981). "Active Peroneal Orthosis." *Proceedings of the International Symposium on External Control of Human Extremities*, pp. 13-20.

Johnson, D. et al. (1996). "Development of a Mobility Assist for the Paralyzed, Amputee, and Spastic Patient," *IEEE Proceedings of the 15th Southern Biomedical Engineering Conference*, pp. 67-70.

Kasaoka, K. et al. (2001). "Predictive Control Estimating Operator's Intention for Stepping-up Motion by Exoskeleton Type Power Assist System HAL," *Proceedings of the 2001 IEEE/RJS: International Conference on Intelligent Robots and Systems*, Maui, Hawaii, pp. 1578-1583.

Kawamoto, H. et al. (2002). "Power Assist System HAL-3 for Gait Disorder Person," Lecture Notes in Computer Science (LNCS), *Proceedings of the Eighth International Conference on Computers Helping People with Special Needs (ICCHP)*. 2398:196-203.

Kawamoto, H. et al. (2002). "Comfortable Power Assist Control Method for Walking Aid by HAL-3," *IEEE Proceedings of the International Conference on Systems, Man, and Cybernetics (SMC)*, 6 pgs.

Kawamoto, H. et al. (2003). "Power Assist Method for HAL-3 Using EMG-Based Feedback Controller." *Proceedings of the IEEE International Conference on Systems, Man and Cybernetics*, pp. 1648-1653.

Kawamoto, H. et al. (Nov. 2003). "Power Assist Method for HAL-3 Estimating Operator's Intention Based on Motion Information." *Proceedings of the 2003 IEEE International Workshop on Robot and Human Interactive Communication*, Millbrae, California, pp. 67-72.

Kazerooni, H. et al. (Apr. 2005). "On the Control of Berkeley Lower Extremity Exoskeleton (BLEEX)," *Proceedings of IEEE International Conference on Robotics and Automation*, Barcelona, Spain, pp. 4364-4371.

Kazerooni, H. et al. (Mar. 2006). "The Berkeley Lower Extremity Exoskeletons." *ASME Journal of Dynamics Systems, Measurements and Control*, vol. 128, pp. 14-25.

Kazerooni, H. et al. (Jan. 2007). "That which does not stabilize, will only make us stronger." *The International Journal of Robotics Research*, vol. 26, No. 1, pp. 75-89.

Kosso, E.V. (1973). "A Minimum Energy Exoskeleton." *Proceedings of the 1973 Carnahan Conference on Electronic Prosthetics*, pp. 86-89.

Kuo, A.D. (Feb. 2002). "Energetics of Actively Powered Locomotion Using the Simplest Walking Model." *Journal of Biomechanical Engineering*, vol. 124, pp. 113-120.

Lazarevic, S.R. et al. (1978). "Logic Control of Partial Active Orthoses via Real Time Computing Systems." *Proceedings of the International Symposium on External Control of Human Extremities*, pp. 247-257.

Lee, S. et al. (Oct. 2002). "Power Assist Control for Leg with HAL-3 Based on Virtual Torque and Impedance Adjustment." *Proceedings of 2002 IEEE Conference on Systems, Man and Cybernetics*, vol. 4, pp. 6-9.

Lee, S. et al. (Oct. 2002). "Power Assist Control for Walking Aid with HAL-3 Based on EMG and Impedance Adjustment Around Knee Joint," *Proceedings of the IEEE/RJS International Conference on Intelligent Robots and Systems (IROS)*, Lausanne, Switzerland, pp. 1499-1504.

Lim, M. Z. M. (Dec. 2000). "An Analysis on the Performance of an Underactuated Lower Extremity Enhancer," Master of Science Thesis submitted to the Mechanical Engineering Department at the University of California, Berkeley, pp. 1-33.

Low, K.H. et al. (Jul. 2005). "Development of NTU Wearable Exoskeleton System for Assistive Technologies." *Proceedings of the IEEE International Conference on Mechatronics & Automation*, Niagara Falls, Canada, pp. 1099-1106.

Liu, X. et al. (Oct. 2004). "Development of a Lower Extremity Exoskeleton for Human Performance Enhancement." *Proceedings of IEEE/RSJ International Conference on Intelligent Robots and Systems*, Sendal, Japan, pp. 3889-3894.

Misuraca, J. et al. (Nov. 2001). "Lower Limb Human Muscle Enhancer," *Proceedings of IMECE01: International Mechanical Engineering Conference and Exposition*, New York, New York, pp. 1-7.

(56) References Cited

OTHER PUBLICATIONS

Mori, Y. (Apr. 2004). "Development of Straight Style Transfer Equipment for Lower Limbs Disabled," *Proceedings of the 2004 IEEE International Conference on Robotics and Automation*, New Orleans, Louisiana, pp. 2486-2491.

Morris, S. et al. (Oct. 2002). "Shoe-Integrated Sensor System for Wireless Gait Analysis and Real-Time Feedback," *Proceedings of the Second Joint EMBS/BMES Conference*, Houston, Texas, pp. 2468-2469.

Mosher, R. S. (Jan. 1967). "Handyman to Hardiman," *Automotive Engineering Congress, Society of Automotive Engineers*, Detroit, Michigan, pp. 1-12.

Naruse, K. et al. (Nov. 2003). "Design of Compact and Lightweight Wearable Power Assist Device," *Proceedings of IMECE '03, 2003 ASME International Mechanical Engineering Congress and Exposition*, Washington, D.C., pp. 1-8.

Popovic, D. et al. (1990). "Powered Hybrid Assistive System." *Proceedings of the International Symposium on External Control of Human Extremities*, pp. 177-186.

Pratt, J. E. et al. (Apr. 2004). "The RoboKnee: An Exoskeleton for Enhancing Strength and Endurance During Walking," *Proceedings of the IEEE International Conference on Robotics and Automation*, New Orleans, Louisiana, pp. 2430-2435.

Rabischong, J.P. et al. (1975) "The Amoil Project." *Proceedings of the 5$^{th}$ International Symposium on External Control of Human Extremities*, ETAN, Dubrovnik, Yugoslavia.

Rabischong, E. et al. (1990). "Control and Command of a Six Degrees of Freedom Active Electrical Orthosis for Paraplegic Patient." *Proceedings of IEEE International Workshop on Intelligent Robots and Systems*, pp. 987-991.

Racine, J. L. C. (2003). "Control of a Lower Exoskeleton for Human Performance Amplification," PhD Thesis submitted to the University of California, Berkeley, pp. 1-832.

Rehnmark, F. L. (May 1997). "Dynamic Simulation and Design of a Powered Underactuated Assistive Walking Device," Master of Science Thesis submitted to the Graduate School at the University of California, Berkeley, pp. 1-35.

Saito, Y. et al. (Jul. 2005). "Development of Externally Powered Lower Limb Orthosis with Bilateral-servo Actuator." *Proceedings of the IEEE 9$^{th}$ International Conference on Rehabilitation Robotics*, Chicago, Illinois, pp. 394-399.

Sawicki, G.S. et al. (Jul. 2005). "Powered Lower Limb Orthoses: Applications in Motor Adaptation and Rehabilitation." *Proceedings of the 2005 IEEE 9$^{th}$ International Conference on Rehabilitation and Robotics*, Chicago, Illinois, pp. 206-211.

Valiente, A. (2005). "Design of a Quasi-Passive Parallel Leg Exoskeleton to Augment Load Carrying for Walking." Graduate Thesis, Massachusetts Institute of Technology, Department of Mechanical Engineering.

Van Den Bogert, A. J. (Oct. 2003). "Exotendons for Assistance of Human Locomotion," *Biomedical Engineering Online* 2(17):1-8.

Vukobratovic, M. et al. (Jan. 1974). "Development of Active Anthropomorphic Exoskeletons," *Medical and Biological Engineering*, pp. 66-80.

Vukobratovic, M. et al. (1981). "New Model of Autonomous 'Active Suit' for Distrophic Patients." *Proceedings of the International Symposium on External Control of Human Extremities*, pp. 32-42.

Vukobratovic, M. et al. (2002). "Humanoid Robots." The Mechanical Systems Design Handbook: *Modeling, Measurement and Control*, CRC Press, Chapter 27.

Walsh, C.J. et al. (2006). "Biomimetic Design of an Under-Actuated Leg Exoskeleton for Load-Carrying Augmentation." Graduate Thesis, Trinity College Dublin, Department of Mechanical Engineering.

Walsh, C.J. et al. (May 2006). "Development of a Lightweight, Underactuated Exoskeleton for Load-carrying Augmentation," *Proceedings of the 2006 IEEE International Conference on Robotics and Automation*, Orlando, Florida, pp. 3485-3491.

Walsh, C.J. et al. (Oct. 2006). "An Autonomous, Underactuated Exoskeleton for Load-carrying Augmentation." *Proceedings of the 2006 IEEE/RSJ International Conference on Intelligent Robots and Systems*, Beijing, China, pp. 1410-1415.

Walsh, C.J. et al. (2007). "A Quasi-passive Leg Exoskeleton for Load-carrying Augmentation." *International Journal of Humanoid Robotics*.

Yamamoto, K. et al. (2002). "Development of Power Assisting Suit for Assisting Nurse Labor," *JSME International Journal*, Series C, 45(3):703-711.

Yamamoto, K. et al. (2003). "Development of Power Assisting Suit (Miniaturization of Supply System to Realize Wearable Suit)," *JSME International Journal*, Series C, 46(3):923-930.

Zoss, A. (2003). "Mechanical Design Implementation of an Exoskeleton," Master of Science Thesis submitted to the University of California, Berkeley, pp. 1-140.

Zoss, A. et al. (Apr. 2006). "Biomechanical Design of the Berkeley Lower Extremity Exoskeleton (BLEEX)." *IEEE/ASME Transactions of Mechatronics*, vol. 11, No. 2, pp. 128-138.

* cited by examiner

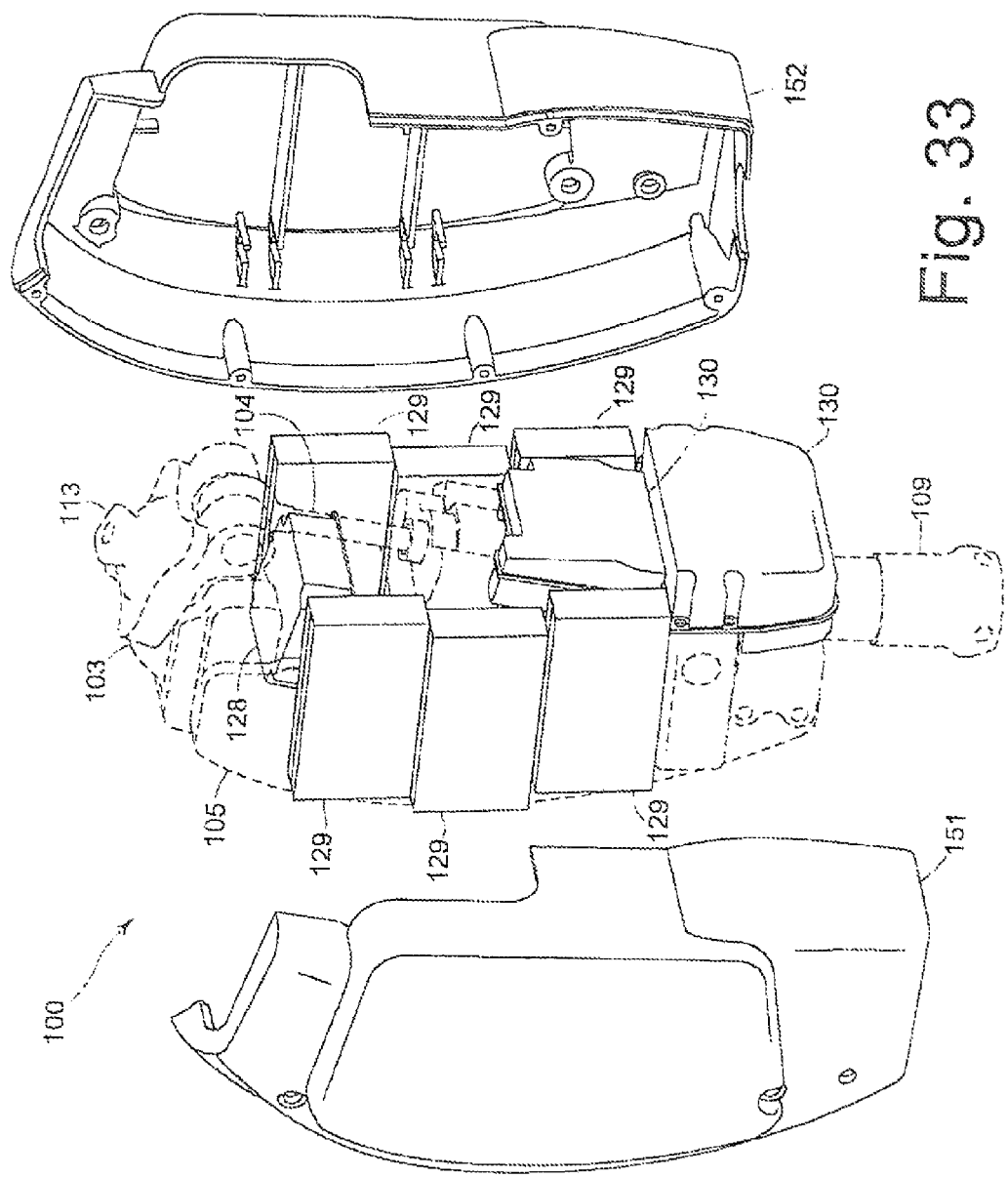

POWERED LOWER EXTREMITY ORTHOTIC AND METHOD OF OPERATION

CROSS-REFERENCE TO RELATED APPLICATIONS

This application constitutes a continuation-in-part of U.S. patent application Ser. No. 12/457,573 entitled SEMI-ACTUATED TRANSFEMORAL PROSTHETIC KNEE, filed on Jun. 16, 2009, pending, which claims the benefit of U.S. Provisional Application No. 61/132,217 entitled SEMI-ACTUATED TRANSFEMORAL PROSTHETIC KNEE, filed on filed Jun. 16, 2008, and U.S. Provisional Application No. 61/136,535 entitled SEMI-ACTUATED TRANSFEMORAL PROSTHETIC KNEE, filed Sep. 12, 2008.

STATEMENT REGARDING FEDERALLY SPONSORED RESEARCH OR DEVELOPMENT

This invention was made with government support under Award No. W81XWH-05-C-0147 awarded by Telemedicine & Advanced Technology Research Center, Department of the Army and under Award No. CMS-0510848 awarded by the National Science Foundation. The government has certain rights in the invention.

BACKGROUND OF THE INVENTION

The overall invention relates generally to the controlling the trajectory of an artificial foot. The invention expands on developments in prosthetics, while translating certain developments into the field of human exoskeletons which are orthotic devices attached to users who still retain their limbs. In particular, these human exoskeletons are used by individuals who have limbs that are paralyzed and therefore need the capability of joint motion restored much like in the case of prosthetics.

In recent years, major advancements have been made in the field of prosthetics. For instance, not only are prosthetics now commonly available for customized fit in connection with a wide range of amputations, but the prosthetics themselves can be customized for use as well. Therefore, fitting an amputee with a prosthetic includes not only customization for size, but also variations based on various other factors, particularly the types of activities in which the amputee will be utilizing the prosthetic device.

In connection with above-knee prosthetics, both swing and stance controls must be established. Certainly, swing controls have to accommodate for a greater range of motions, with the potential motions even varying in dependence on the age and activity level of the amputee. In this regard, fluid systems have been employed in the past, often due to their ability to establish relatively consistent motions. However, fluctuations in the speed of movement may be needed as well such that proper control of the fluid system is also needed. Also, it is believed that certain properties of developments in the field of prosthetics can be advantageously translated into other orthotic fields, particularly human exoskeletons.

SUMMARY OF THE INVENTION

The present invention is concerned with a powered, lower extremity orthotic which operates similarly to an above knee prosthetic. In accordance with one aspect of the invention, a semi-actuated above knee prosthetic system that is mostly passive in nature in that the system only requires power for locomotion during a portion of a walking cycle. In general, the prosthetic includes a shank link adapted to be coupled to an artificial foot, a knee mechanism connected to the shank link at a position remote from the artificial foot and a thigh link adapted to be attached to an above-knee remaining lower limb of an amputee. The knee mechanism is configured to provide flexion and extension movements of the thigh and shank links relative to each other. In accordance with the invention, the prosthetic is operable in, either an actuated mode or an un-actuated mode. In the actuated mode, power is delivered to a torque generator connected to the knee mechanism to cause a forced movement between the thigh and shank links. In the un-actuated mode, a control circuit operates in a non-powered manner to allow operation of the knee mechanism with modulated resistance.

In accordance with a preferred embodiment of the invention, an electric motor is connected to a battery source and employed to drive a hydraulic pump which is part of an overall hydraulic power unit including the torque generator used to regulate the knee mechanism. A signal processor controls the operation of the hydraulic power unit in order to establish the actuated and un-actuated modes based on signals received from a plurality of sensors provided on the above-knee prosthetic. Although the location, number and type of sensors can vary, one preferred embodiment employs a stance sensor capable of identifying a particular part of an artificial foot which is in contact with a support surface (e.g., the ground), while the signal processor selects a desired swing state when the artificial foot leaves the support surface based on an estimated location of the artificial foot with respect to a trunk of the amputee. Knee angle, thigh angle, pressure and other sensors can also be employed for additional, control purposes.

With this arrangement, the overall system advantageously employs less electric power than fully powered knees and therefore an amputee can walk much longer for a given battery size. In addition, the above-knee prosthetic of the invention is generally smaller than fully actuated knees. Furthermore, the semi-actuated prosthetic knee reduces necessary hip torque and power that the amputee must physically exert by efficiently creating synchronized torque and power during an effective portion of a walking cycle. Even further, the various sensors provide inputs to the signal processor that effectively maximize the range and type of motions generated for the amputee.

The prosthetic knee of the invention also is controlled in a manner that allows the foot, or more specifically the toe, to track a trajectory through space that is consistent with respect to the ground, rather than simply repeating a knee motion during swing regardless of the orientation of the prosthetic with respect to the ground. This is accomplished by measuring the angle of the user's thigh and using it to derive the current knee angle necessary to describe a defined trajectory. In accordance with the overall invention, in addition to uses with prosthetics, this technique has direct application to other orthotic devices, particularly human exoskeletons.

Additional objects, features and advantages of the invention will become more fully evident below from the following detailed description of preferred embodiments wherein like reference numerals refer to corresponding parts in the various views.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 33 is a partial exploded view of a semi-actuated prosthetic knee of the present invention;

DETAILED DESCRIPTION OF THE INVENTION

Figure 1:
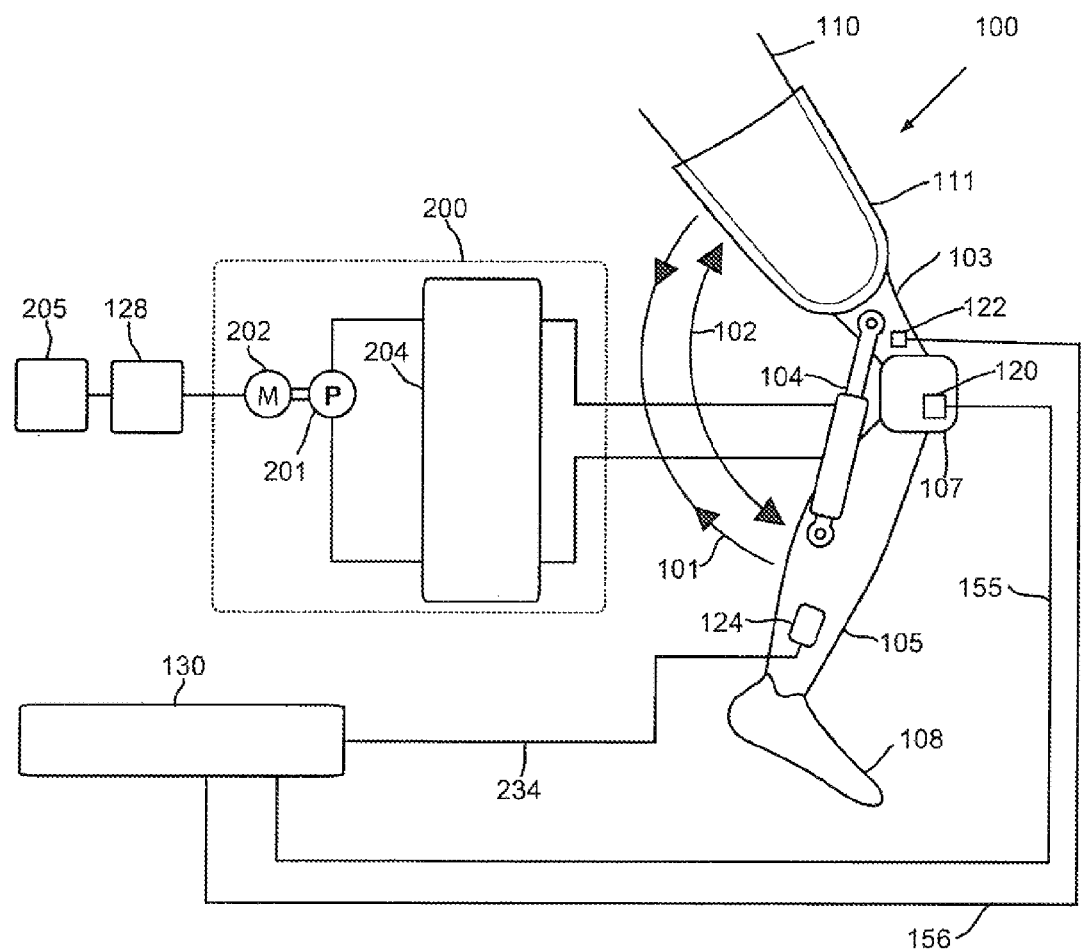
FIG. 1 depicts a semi-actuated prosthetic knee constructed in accordance with a first embodiment of the invention.

With initial reference to FIG. 1, a semi-actuated prosthetic knee 100 constructed in accordance with a first embodiment of the invention is configurable to be coupled to an above-knee amputee's remaining lower limb 110 through a socket 111. Semi-actuated prosthetic knee 100, among other components, comprises a thigh link 103 coupled to a knee mechanism 107 and a shank link 105 coupled to an artificial foot 108. Knee mechanism 107 is configured to allow flexion and extension movements of thigh link 103 and a shank link 105 relative to each other along flexion direction 101 and extension direction 102. A hydraulic torque generator 104 is configured to generate torque between thigh link, 103 and shank link 105.

Semi-actuated prosthetic knee 100 further includes a hydraulic power unit indicated at 200 coupled to hydraulic torque generator 104. Hydraulic power unit 200, among other components, includes a hydraulic valve circuit 204, which is hydraulically coupled to torque generator 104. Hydraulic power unit 200 further includes a hydraulic pump 201 mechanically coupled to an electric motor 202 and hydraulically coupled to hydraulic valve circuit 204.

Semi-actuated prosthetic knee 100 further includes an electric power source 205 capable of providing electric power to electric motor 202 and other components of semi-actuated prosthetic knee 100. A motor controller 128 (sometimes referred to as an amplifier) converts the output of electric power source 205 to an appropriate voltage or current for electric motor 202. Semi-actuated prosthetic knee 100 further includes a signal processor 130 that among other tasks controls electric motor 202 and implements a controller that includes a set of states. Semi-actuated prosthetic knee 100 additionally includes a stance sensor 124 producing stance signal 234. Stance signal 234, among other information, includes information identifying which part of artificial foot 108 is in contact with the ground.

In operation when semi-actuated prosthetic knee 100 is in its actuated mode, semi-actuated prosthetic knee 100 is configured such that it transfers electric power from electric power source 205 to electric motor 202, powering electric motor 202 and hydraulic pump 201. In this actuated mode, hydraulic valve circuit 204 is configured such that hydraulic pump 201 hydraulically couples to torque generator 104. This hydraulic coupling between hydraulic pump 201 and torque generator 104 allows signal processor 130 to control torque generator 104. The ability to inject power to torque generator 104 allows one to control the motion of knee mechanism 107 or impose desirable torque onto knee mechanism 107 during various phases of the walking cycle.

When semi-actuated prosthetic knee 100 is in an un-actuated mode, hydraulic power unit 200 is configured such that no electric power from electric power source 205 is transferred to electric motor 202. In this un-actuated mode hydraulic valve circuit 204 modulates the resistance of the fluid flow in torque generator 104. The ability to modulate the resistance of fluid flow in torque generator 104 allows one to control the resistance of knee mechanism 107 to forces and torques during various phases of the walking cycle with reduced use of electric power since electric motor 202 is not consuming any electric power in this un-actuated mode.

Examples of hydraulic torque generators 104 include, without limitation, linear hydraulic piston-cylinders, rotary hydraulic actuators, rack-and-pinion-type rotary actuators and rotary hydraulic vane type actuators where pressurized hydraulic fluid, by pushing against moving surfaces, generate force or torque.

Examples of electric power source 205 include, without limitation, batteries, Nickel-Metal Hydride (NiMH) batteries, Lithium batteries, Alkaline batteries, rechargeable Alkaline batteries, Lithium-ion batteries, and Lithium ion polymer batteries.

Examples of electric motor 202 include, without limitation, electric motors, including, without limitation, AC (alternating current) motors, brush-type DC (direct current) motors, brushless DC motors, electronically commutated motors (ECMs), stepping motors, and combinations thereof.

Examples of hydraulic pump 201 include, without limitation, gear pumps, gerotor pumps, rotary vane pumps, screw pumps, bent axis pumps, axial piston pumps swashplate pumps, radial piston pumps, and peristaltic pumps.

Examples of stance sensor 124 include, without limitation, force sensors, strain gage force sensors, piezoelectric force sensors, force sensing resistors, load cells, deflection-based positioning sensors, encoders, potentiometers, pressure sensors in a trapped hydraulic fluid, and combinations thereof.

Examples of knee mechanism 107 include, without limitation, rotary pivots, four-bar linkages, sliding joints, rolling element joints, and combinations thereof.

Signal processor 130 comprises an element or combination of elements selected from the group consisting of analog devices; analog computation modules; digital devices including, without limitation, small-, medium-, and large-scale integrated circuits, application specific integrated circuits, programmable gate arrays, programmable logic arrays; electromechanical relays, solid state switches, MOSFET switches and digital computation modules including, without limitation, microcomputers, microprocessors, microcontrollers, and programmable logic controllers. In operation signal processor 130 collects information from various sensors and after some computation commands what various components of hydraulic circuit should do.

In some embodiments of the invention, as shown in FIG. 1, semi-actuated prosthetic knee 100 further comprises a knee angle sensor 120 which generates a knee angle signal indicated at 155 representing the angle between thigh link 103 and shank link 105. Knee angle sensor 120 comprises an element or combination of elements selected from a the group consisting of an encoder, digital encoder, magnetic encoder, optical encoder, potentiometer, LVDT, and resolver.

Figure 22:
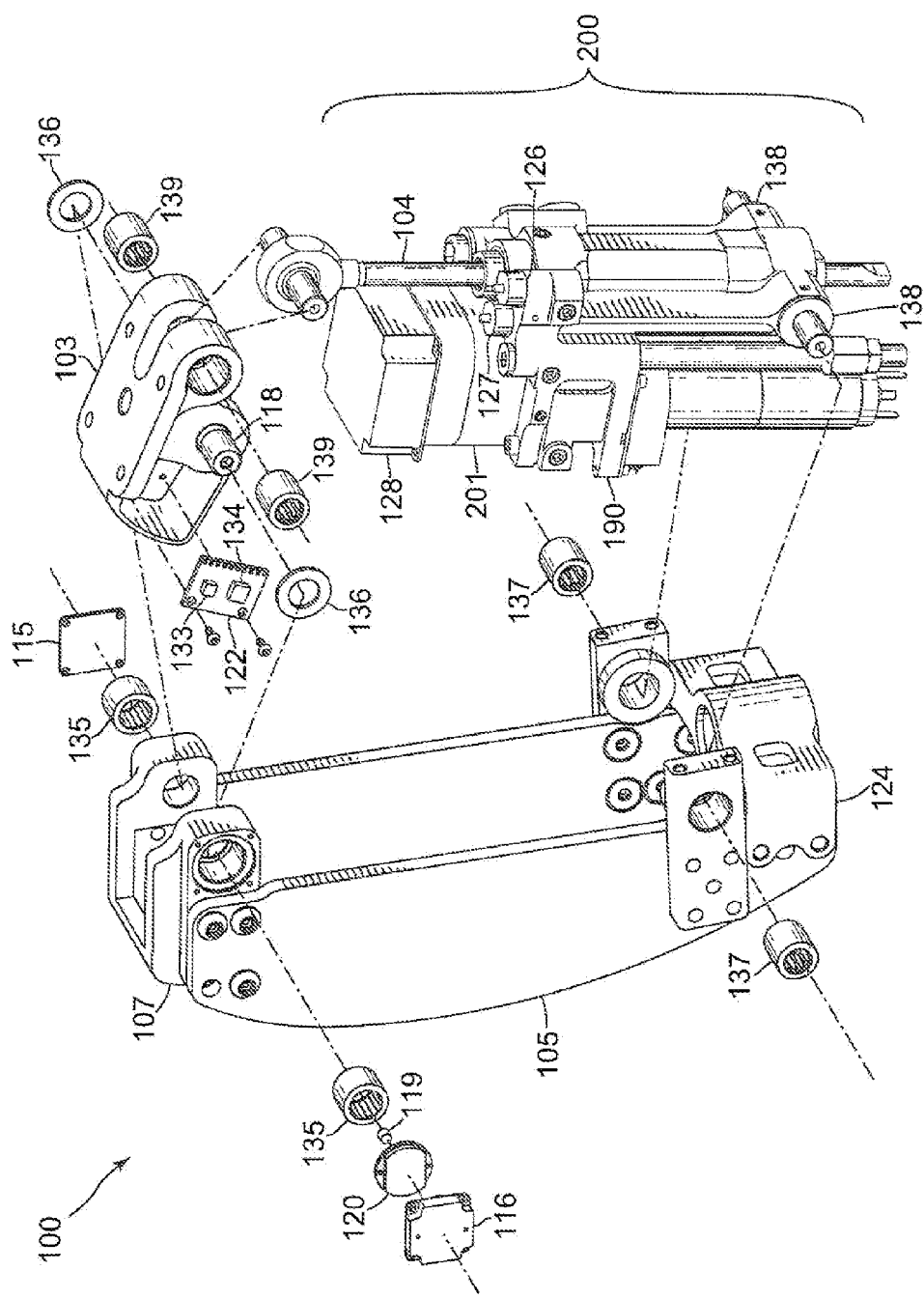
FIG. 22 is an exploded view of the semi-actuated prosthetic knee of FIG. 21.

In some embodiments, as shown in FIG. 1, semi-actuated prosthetic knee 100 further comprises a thigh angle sensor 122, which generates a thigh angle signal indicated at 156 representing the absolute angle of thigh link 103. Thigh angle sensor 122 comprises an element or combination of elements selected from a the group consisting of, accelerometers, gyroscopes, inclinometers, encoders, potentiometers and combinations thereof. FIG. 22 represents an embodiment of the invention where thigh angle sensor 122 fixed to thigh link 103 comprises an accelerometer 133 and a gyroscope 134.

Figure 16:
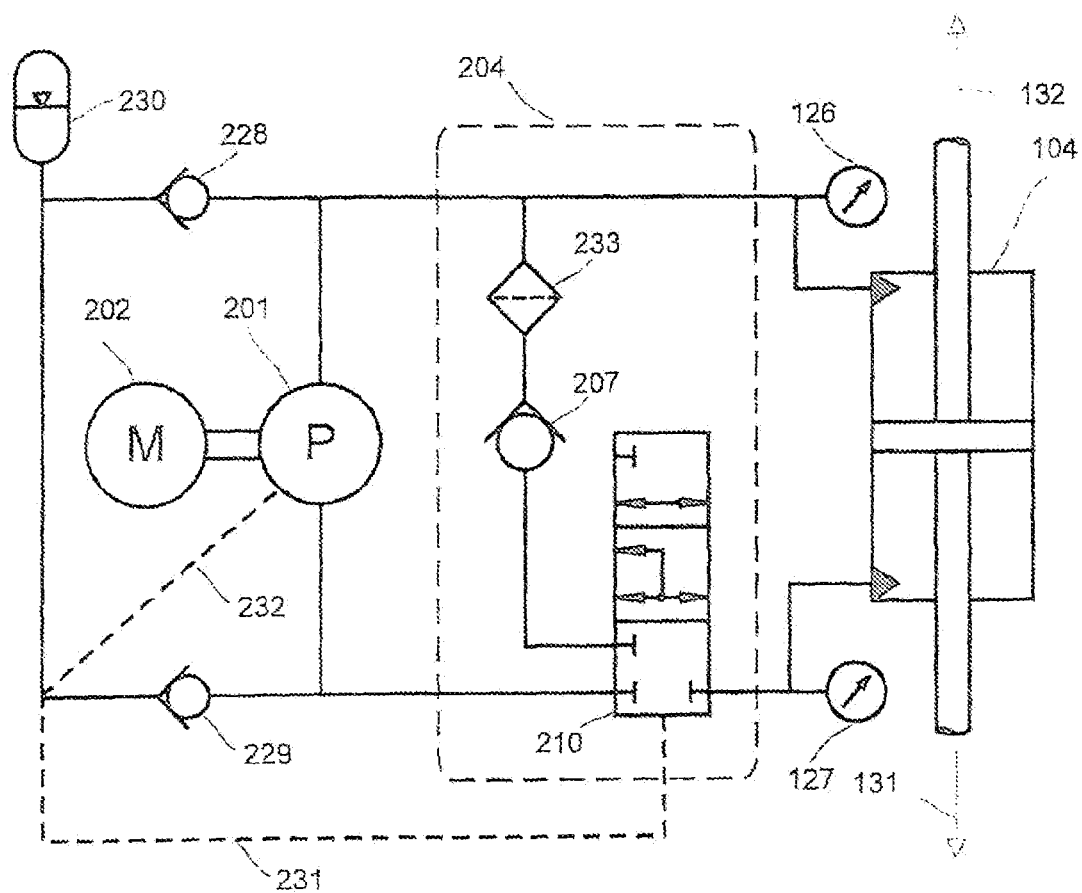
FIG. 16 is a diagram of an alternative hydraulic valve circuit including a fluid reservoir.

In some embodiments of the invention semi-actuated prosthetic knee 100 further comprises a torque sensor or a force sensor (as detailed below) representing the torque or force of torque generator 104. In some embodiments of the invention a force sensor is installed on the piston of linear torque generator 104. In some embodiments of the invention, the force sensor for semi-actuated prosthetic knee 100 comprises two pressure sensors 126 and 127 measuring the fluid pressure in both sides of torque generator 104, as depicted in FIG. 16. The measurements from two pressure sensors 126 and 127 also represent the force in torque generator torque generator 104.

In some embodiments as shown in FIG. 1, stance sensor 124 comprises a force-torque sensor installed on shank link 105 measuring the force and the moment in the sagittal plane.

Figure 2:
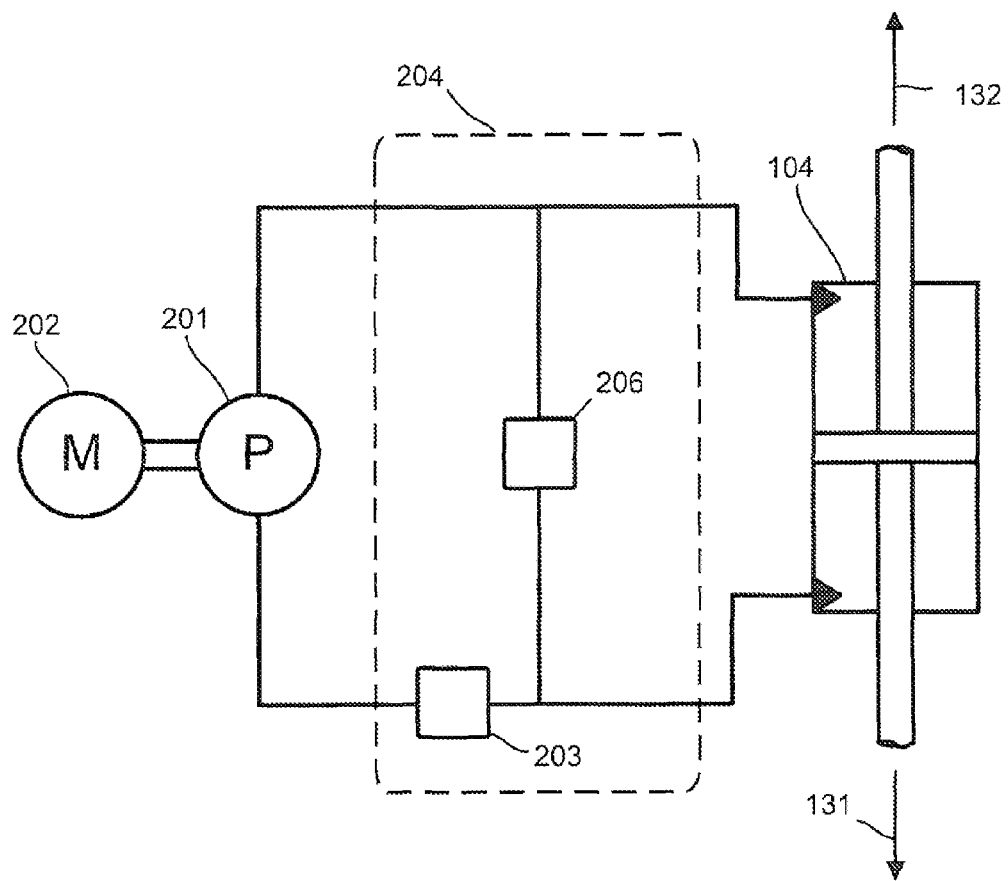
FIG. 2 is a diagram of a first hydraulic valve circuit of the present invention.

In some embodiments, as shown in FIG. 2, hydraulic valve circuit 204 comprises a first controllable valve 206 capable of allowing the hydraulic flow in two directions and a pump valve 203 serially connected to each other. Hydraulic pump 201 is coupled to two end ports of this serially-connected chain of first controllable valve 206 and pump valve 203. Torque generator 104 is coupled to two ports of first controllable valve 206. In some cases, when semi-actuated prosthetic knee 100 operates in its actuated mode, first controllable valve 206 is closed. This allows the entire hydraulic pump output flow to travel to torque generator 104. This further allows signal processor 130 to control torque generator 104 by controlling electric motor 202. The ability to inject power to torque generator 104, in the actuated mode, allows one to control the motion of knee mechanism 107 or impose desirable torque onto knee mechanism 107.

When semi-actuated prosthetic knee 100 operates in its un-actuated mode, pump valve 203 is either closed or partially closed. When pump valve 203 is fully closed, no flow passes through hydraulic pump 201. Through the use of signal processor 130, one can adjust the opening of first controllable valve 206 to modulate and adjust properly the resistance of fluid flow in torque generator 104. When pump valve 203 is partially closed, one can only modulate the resistance of fluid flow in torque generator 104 from zero to the combined flow resistance of pump valve 203 and hydraulic pump 201. The ability to modulate the resistance of fluid flow in torque generator 104 allows one to control the resistance of knee mechanism 107 to forces and torques with reduced use of electric power since electric motor 202 is not consuming any electric power in this un-actuated mode.

When semi-actuated prosthetic knee 100 operates in a power regenerative mode, pump valve 203 is not closed, allowing at least a portion of the hydraulic flow from torque generator 104 to turn hydraulic pump 201 while motor controller 128 applies a non-zero current onto electric motor 202 to resist the hydraulic flow in hydraulic pump 201.

For better clarification of the embodiments of hydraulic valve circuit 204, the flexion and extension will be defined as follows. The flexion of prosthetic knee 100 takes place when the piston of torque generator 104 moves in direction of arrow 131 depicted in FIG. 2. Extension of prosthetic knee 100 takes place when the piston of torque generator 104 moves in direction of arrow 132 depicted in FIG. 2.

Figure 3:
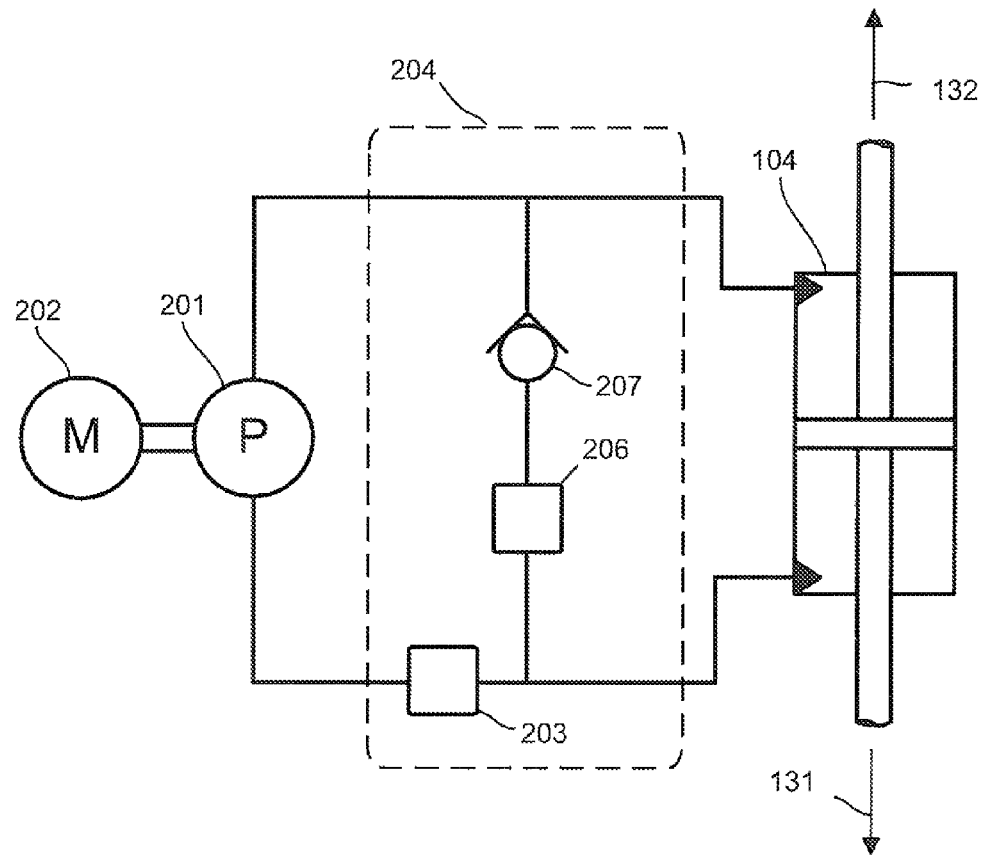
FIG. 3 is a diagram of the hydraulic valve circuit of FIG. 2, further comprising a first check valve.

In some embodiments, as shown in FIG. 3, hydraulic valve circuit 204, among other components, further comprises a first check valve 207 installed in series with first controllable valve 206. The operation of this embodiment is similar to the operation of the embodiment shown in FIG. 2, except that first hydraulic controllable valve 206 modulates the resistance of the fluid flow in torque generator 104 in one direction only. In comparison with the embodiment of FIG. 2, this embodiment constrains the range of resistance of fluid flow in torque generator 104 in flexion direction to always be more than the flow resistance that hydraulic pump 201 creates. It further allows free extension of torque generator 104 if first controllable valve 206 is open without compromising the ability to inject power in the extension direction of torque generator 104. Similar to the embodiment of FIG. 2, when semi-actuated prosthetic knee 100 operates in its actuated mode, first controllable valve 206 is closed. This allows signal processor 130 to control torque generator 104 by controlling electric motor 202. The ability to inject power to torque generator 104, in the actuated mode, allows one to control the motion of knee mechanism 107 or impose desirable torque onto knee mechanism 107.

Figure 4:
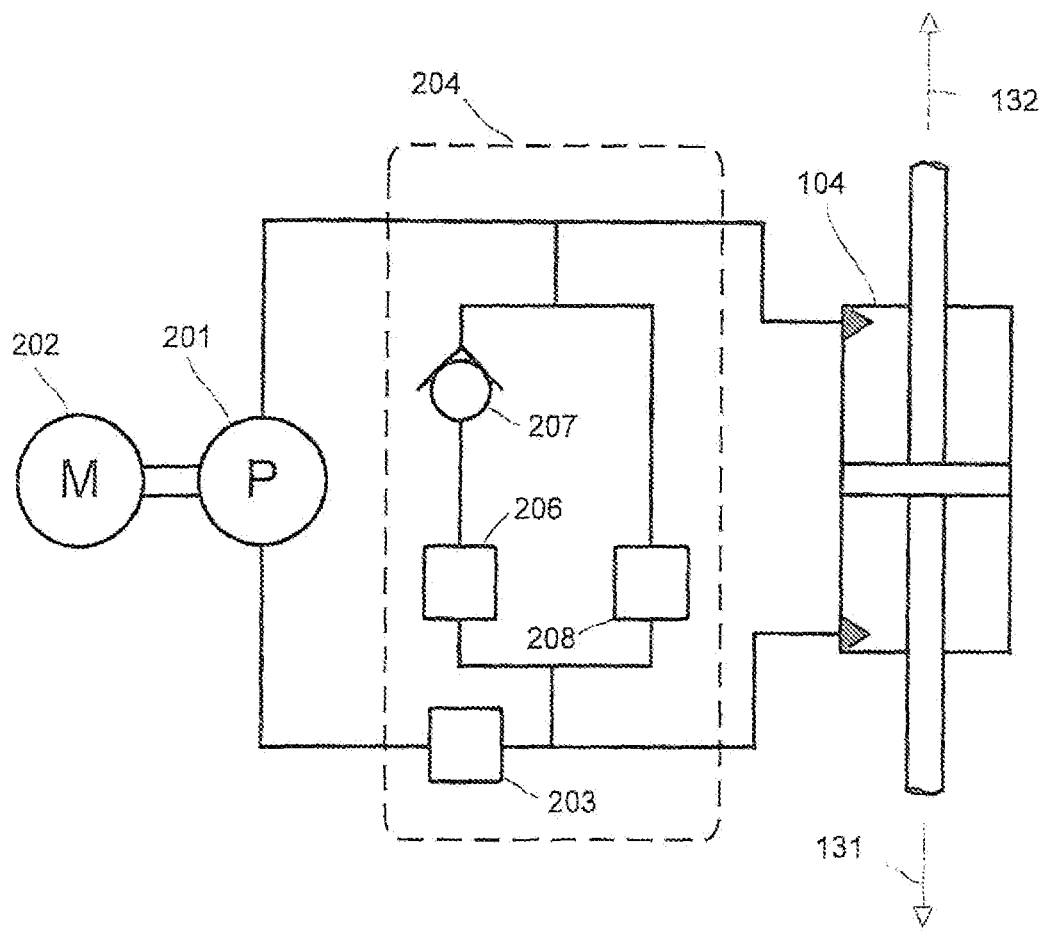
FIG. 4 is a diagram of the hydraulic valve circuit of FIG. 3, further comprising a second controllable valve.

In some embodiments, as shown in FIG. 4, hydraulic valve circuit 204, among other components, further comprises a second controllable valve 208 installed in parallel with serially-installed first controllable valve 206 and first check valve 207. Through the use of signal processor 130, one can adjust the opening of first controllable valve 206 and second controllable valve 208 to modulate and adjust properly the resistance of fluid flow in torque generator 104. The operation of this embodiment is similar to the operation of the embodiment shown in FIG. 3, except that this embodiment does not constrain the range of resistance of fluid flow in flexion direction in torque generator 104. When semi-actuated prosthetic knee 100 operates in its actuated mode, first controllable valve 206 and second controllable valve 208 are closed. This allows signal processor 130 to control torque generator 104 by controlling electric motor 202. The ability to inject power to torque generator 104, in the actuated mode, allows one to control the motion of knee mechanism 107 or impose desirable torque onto knee mechanism 107.

Figure 5:
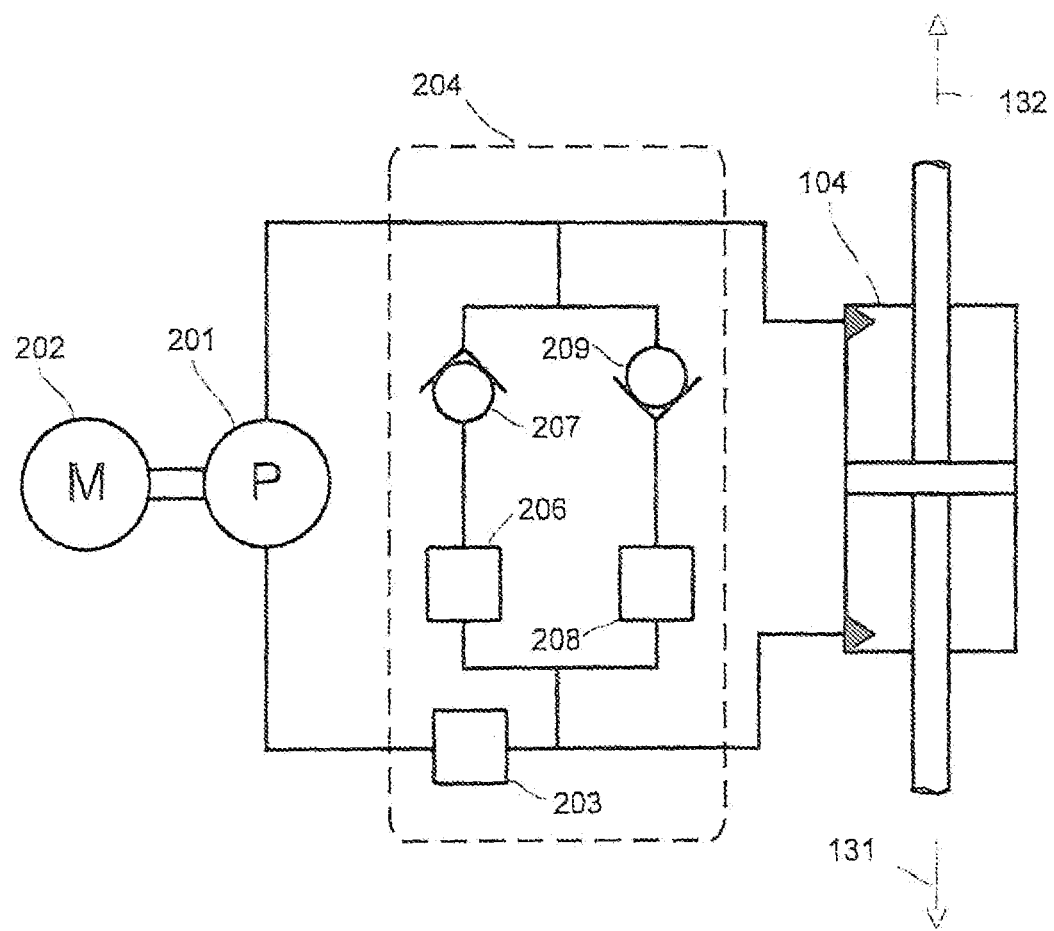
FIG. 5 is a diagram of the hydraulic valve circuit of FIG. 4, further comprising a second check valve.

In some embodiments, as shown in FIG. 5, hydraulic valve circuit 204, includes a second check valve 209 and second controllable valve 208 installed in series relative to each other and installed in parallel with serially installed first controllable valve 206 and first check valve 207. The operation of this embodiment is similar to the operation of the embodiment shown in FIG. 4 except it allows free flexion of torque generator 104 if second controllable valve 208 is open without compromising the ability to inject power in the flexion direction of torque generator 104. Similar to the embodiment of FIG. 4, when hydraulic valve circuit 204 of FIG. 5 operates in its actuated mode, first controllable valve 206 and second controllable valve 208 are closed and that allows one to control the motion of knee mechanism 107 or impose desirable torque onto knee mechanism 107.

Both first controllable valve 206 and second controllable valve 208 comprise any valve or combination of valves that allow for variation or adjustment of their openings either electronically or manually. Examples of first controllable valve 206 and second controllable valve 208 include, without limitation, a flow control valve, a pressure control valve, actuated needle valves, solenoid valves and an on-off valve.

Figure 6:
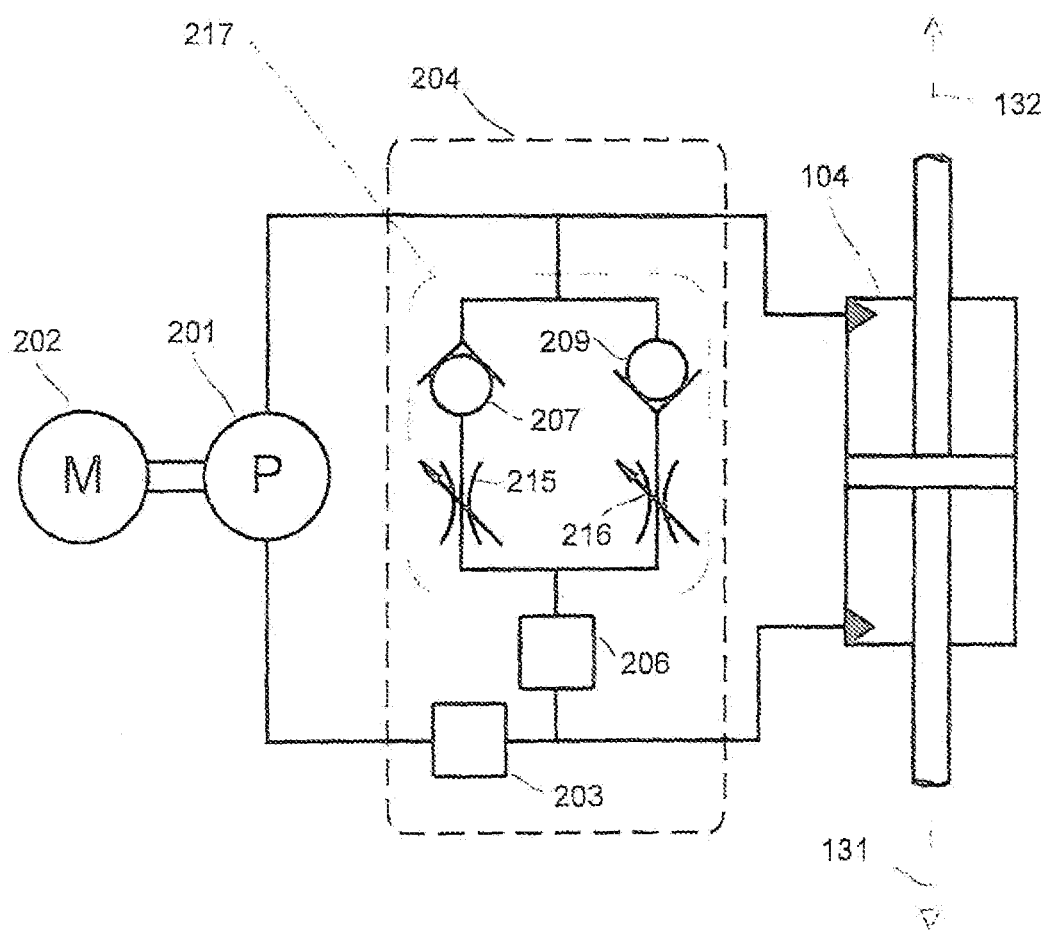
FIG. 6 is a diagram of an alternative hydraulic valve circuit including a parallel path circuit.

FIG. 6 shows another embodiment of hydraulic valve circuit 204. The embodiment of hydraulic valve circuit 204 of FIG. 6 is the same as embodiment of FIG. 3 except first check valve 207 in FIG. 3 is replaced by parallel path circuit 217. Parallel path circuit 217 comprises a first check valve 207 and a first adjustable restrictor valve 215 installed in series relative to each other and installed in parallel with serially installed second check valve 209 and a second adjustable restrictor valve 216.

In operation, when semi-actuated prosthetic knee 100 operates in its actuated mode, first controllable valve 206 is closed. This allows the entire hydraulic pump output flow to travel to torque generator 104. This further allows signal processor 130 to control torque generator 104 by controlling electric motor 202. The ability to inject power to torque generator 104, in actuated mode, allows one to control the motion of knee mechanism 107 or impose desirable torque onto knee mechanism 107. When semi-actuated prosthetic knee 100 operates in its un-actuated mode, pump valve 203 is closed so that no flow passes through hydraulic pump 201. Through the use of signal processor 130, one can adjust the opening of first controllable valve 206 to modulate the resistance of fluid flow in torque generator 104. Adjustable restrictor valve 215 is adjusted to provide resistance to fluid flow in the extension direction of torque generator 104. Adjustable restrictor valve 216 is adjusted to provide resistance to fluid flow in the flexion direction of torque generator 104. The ability to modulate the resistance of fluid flow in torque generator 104 allows one to control the resistance of knee mechanism 107 to forces and torques, with reduces use of electric power since electric motor 202 is not consuming any electric power in this un-actuated mode.

Figure 7:
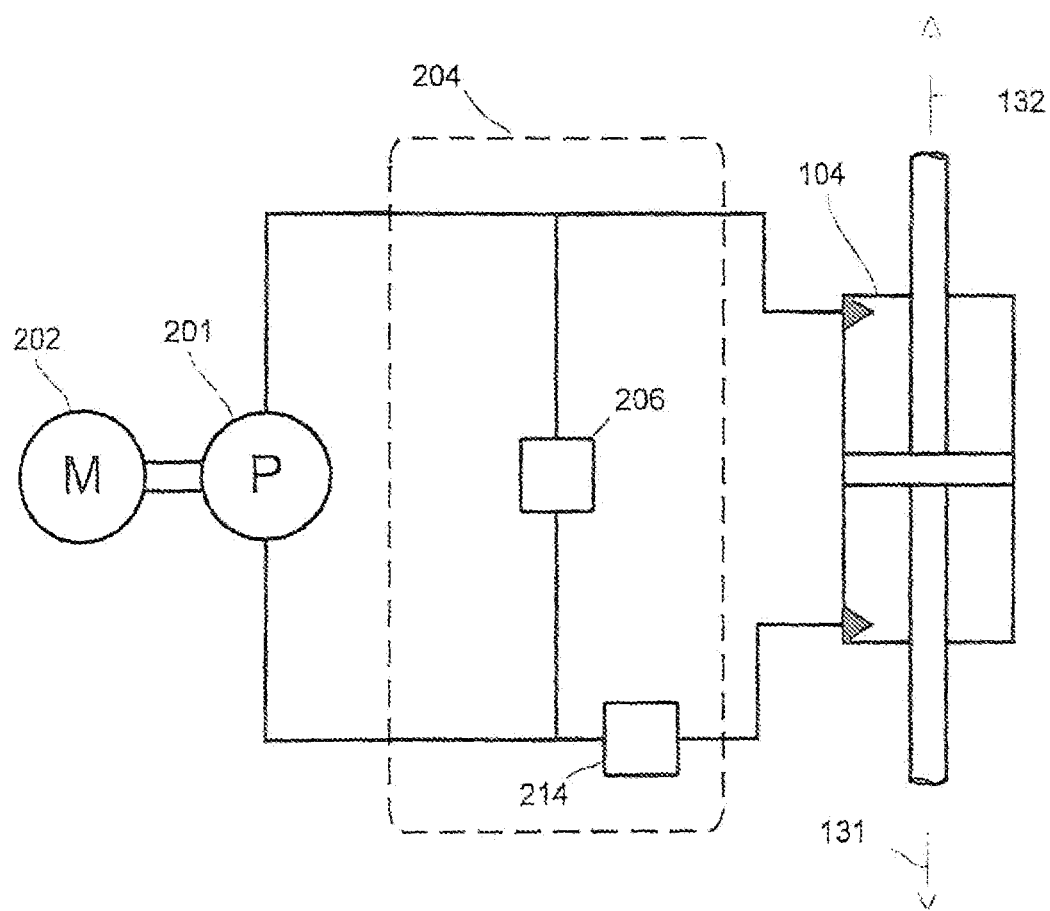
FIG. 7 is a diagram of an alternative hydraulic valve circuit including an actuator valve.

In some embodiments, as shown in FIG. 7, hydraulic valve circuit 204 comprises a first controllable valve 206 capable of controlling the hydraulic flow in two directions and an actuator valve 214 serially connected to each other. In this embodiment, torque generator 104 is coupled to two free ports of this serially connected first controllable valve 206 and said actuator valve 214. Hydraulic pump 201 is coupled to two ports of first controllable valve 206.

In operation, when semi-actuated prosthetic knee 100 operates in its actuated mode, first controllable valve 206 is closed. This allows the entire hydraulic pump output flow to travel to torque generator 104. This further allows signal processor 130 to control torque generator 104 by controlling electric motor 202. The ability to inject power to torque generator 104, in actuated mode, allows one to control the motion of knee mechanism 107 or impose desirable torque onto knee mechanism 107. When semi-actuated prosthetic knee 100 operates in its un-actuated mode, through the use of signal processor 130, one can adjust the opening of actuator valve 214 to modulate the resistance of fluid flow in torque generator 104. The ability to modulate the resistance of fluid flow in torque generator 104 allows one to control the resistance of knee mechanism 107 to forces and torques with reduced use of electric power since electric motor 202 is not consuming any electric power in this un-actuated mode.

When semi-actuated prosthetic knee 100 operates in a power regenerative mode, actuator valve 214 is not closed, allowing at least a portion of the hydraulic flow from torque generator 104 to turn hydraulic pump 201 while motor controller 128 applies a non-zero current onto electric motor 202 to resist the hydraulic flow in hydraulic pump 201.

Figure 8:
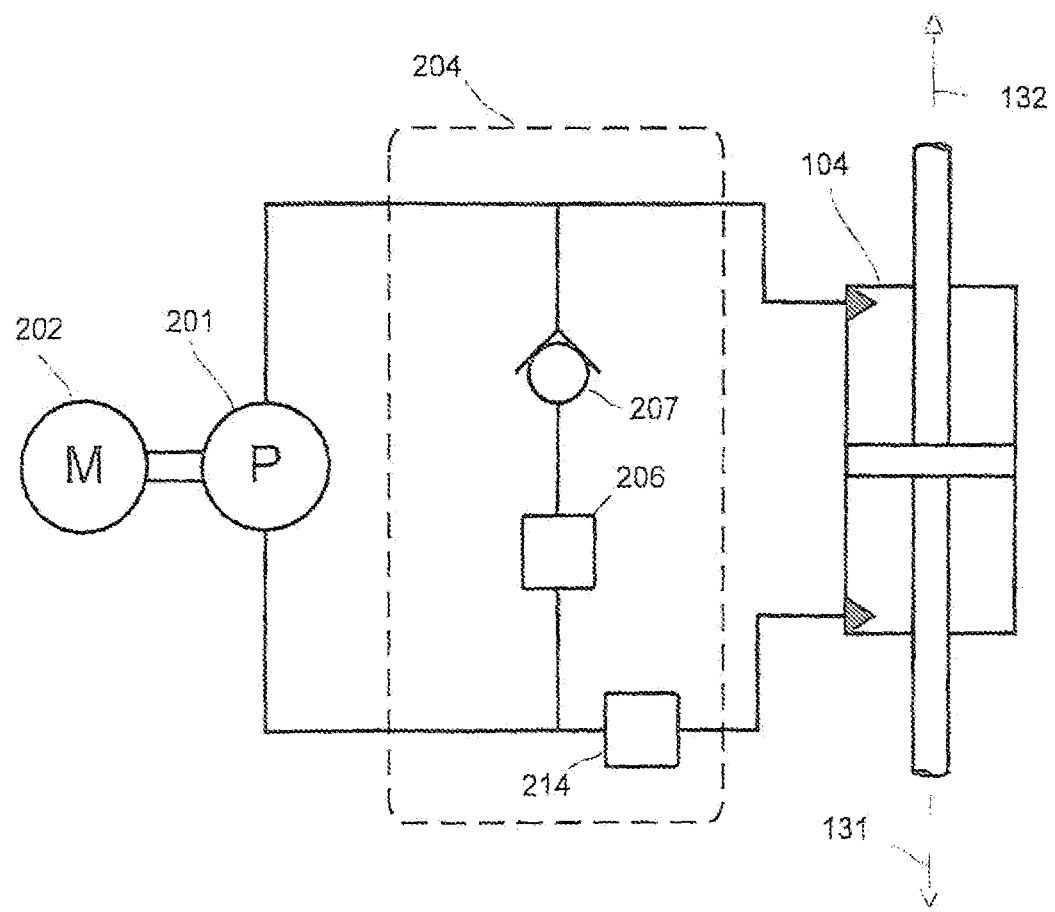
FIG. 8 is a diagram of the hydraulic valve circuit of FIG. 7, further comprising a first check valve.

In some embodiments, as shown in FIG. 8, hydraulic valve circuit 204, among other components, further comprises a first check valve 207 installed in series with first controllable valve 206 allowing the hydraulic flow in one direction only. In comparison with the embodiment of FIG. 7, this embodiment constrains the resistance of fluid flow in torque generator 104 in the flexion direction to always be more than the flow resistance that hydraulic pump 201 creates. It further allows free extension of torque generator 104 if first controllable valve 206 is open without compromising the ability to inject power in the extension direction of torque generator 104. When semi-actuated prosthetic knee 100 operates in its actuated mode, first controllable valve 206 is closed. This allows one to control the motion of knee mechanism 107 or impose desirable torque onto knee mechanism 107.

Figure 9:
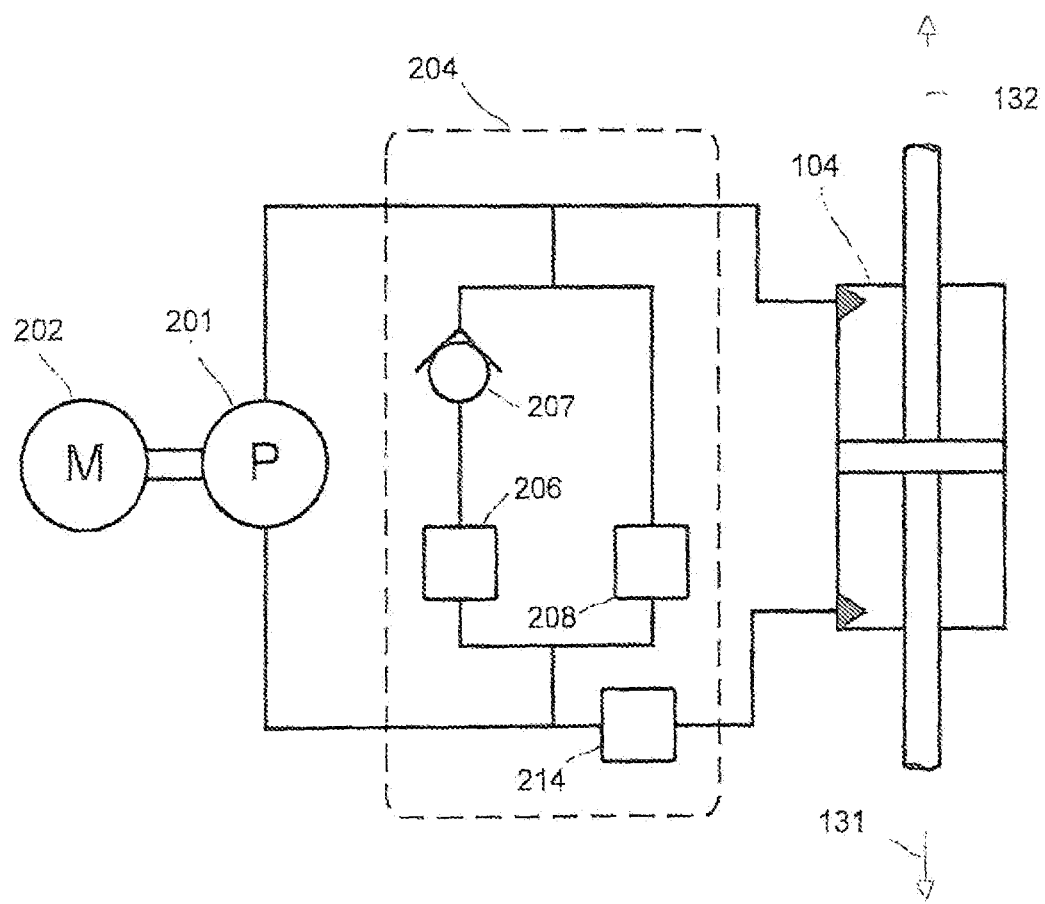
FIG. 9 is a diagram of the hydraulic valve circuit of FIG. 8, further comprising a second controllable valve.

In some embodiments, as shown in FIG. 9, hydraulic valve circuit 204, among other components, further comprises a second controllable valve 208 installed in parallel with serially-installed first controllable valve 206 and first check valve 207. The operation of this embodiment is similar to the operation of the embodiment shown in FIG. 8 except this embodiment does not constrain the resistance of fluid flow in torque generator 104 in the flexion direction to always be more than the flow resistance that hydraulic pump 201 creates. In operation, when hydraulic valve circuit 204 of FIG. 9 operates in its actuated mode, first and second controllable valves 206 and 208 are closed. This allows the entire hydraulic pump output flow to travel to torque generator 104. This further allows signal processor 130 to control torque generator 104 by controlling electric motor 202. The ability to inject power to torque generator 104, in actuated mode, allows one to control the motion of knee mechanism 107 or impose desirable torque onto knee mechanism 107.

Figure 10:
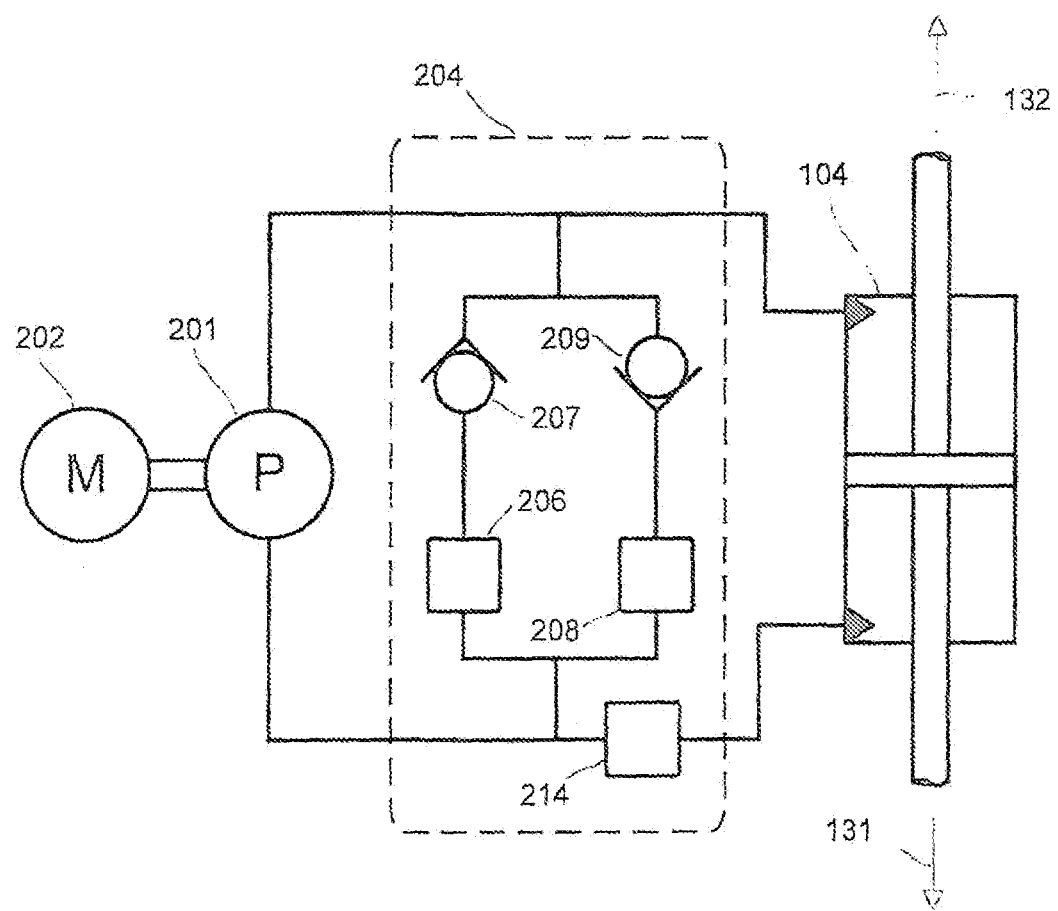
FIG. 10 is a diagram of the hydraulic valve circuit of FIG. 9, further comprising a second check valve.

In some embodiments, as shown in FIG. 10, hydraulic valve circuit 204 comprises a second check valve 209 and second controllable valve 208 installed in series relative to each other and installed in parallel with serially installed first controllable valve 206 and first check valve 207. The operation of this embodiment is similar to the operation of the embodiment shown in FIG. 9 except it allows free flexion of torque generator 104 if second controllable valve 208 is open without compromising the ability to inject power in the flexion direction of torque generator 104. When semi-actuated prosthetic knee 100 operates in its actuated mode, first and second controllable valves 206 and 208 are closed. This allows one to control the motion of knee mechanism 107 or impose desirable torque onto knee mechanism 107.

Figure 11:
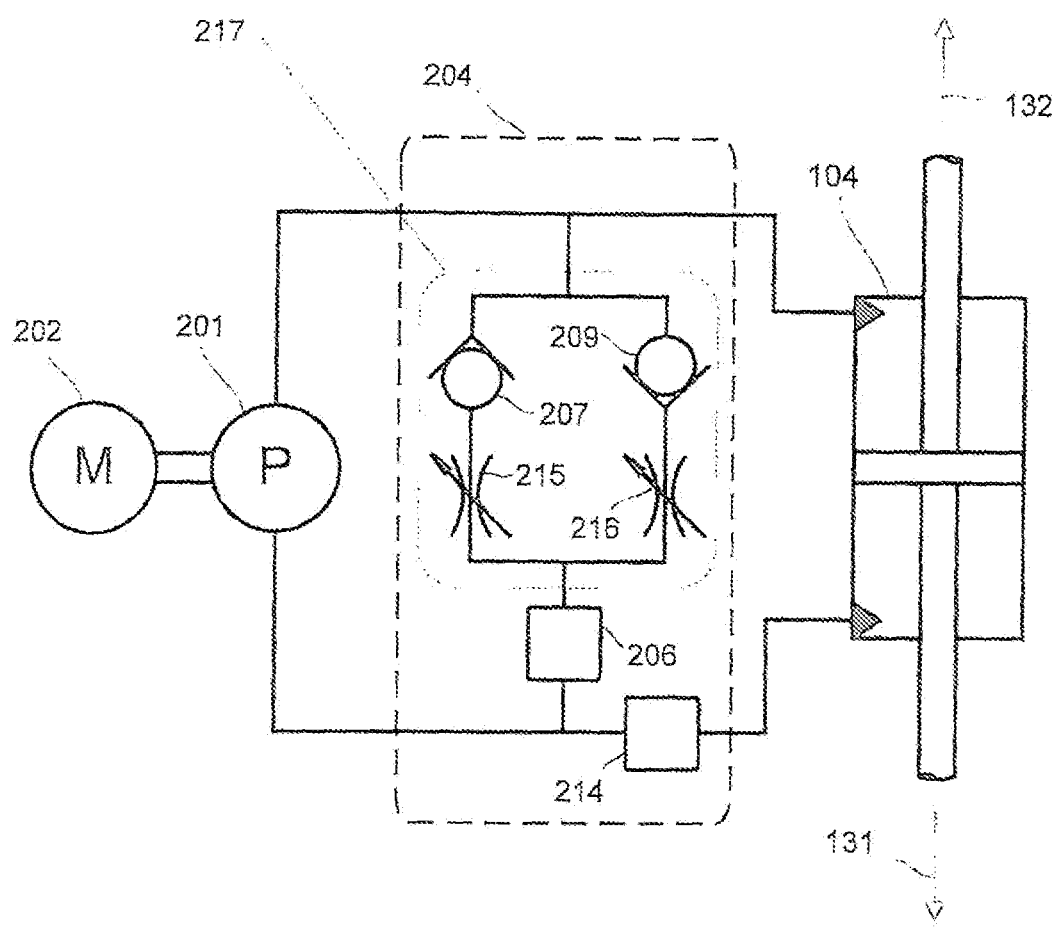
FIG. 11 is a diagram of an alternative hydraulic valve circuit including a parallel path circuit.

FIG. 11 shows another embodiment of hydraulic valve circuit 204. The embodiment of hydraulic valve circuit 204 of FIG. 11 is the same as embodiment of FIG. 8 except check valve 207 in FIG. 8 is replaced by parallel path circuit 217. Parallel path circuit 217 comprises a first check valve 207 and first adjustable restrictor valve 215 installed in series relative to each other and installed in parallel with serially installed second check valve 209 and second adjustable restrictor valve 216.

In operation, when semi-actuated prosthetic knee 100 operates in its actuated mode, first controllable valve 206 is closed. This allows the entire hydraulic pump output flow to travel to torque generator 104. This further allows signal processor 130 to control torque generator 104 by controlling electric motor 202. The ability to inject power to torque generator 104, in actuated mode, allows one to control the motion of knee mechanism 107 or impose desirable torque onto knee mechanism 107. When semi-actuated prosthetic knee 100 operates in its un-actuated mode, one can adjust the opening of actuator valve 214 to modulate the resistance of fluid flow in torque generator 104. First adjustable restrictor valve 215 is adjusted to provide resistance to fluid flow in the extension direction of torque generator 104. Second adjustable restrictor valve 216 is adjusted to provide resistance to fluid flow in the flexion direction of torque generator 104. The ability to modulate the resistance of fluid flow in torque generator 104 allows one to control the resistance of knee mechanism 107 to forces and torques with reduced use of electric power since electric motor 202 is not consuming any electric power in this un-actuated mode.

Figure 12:
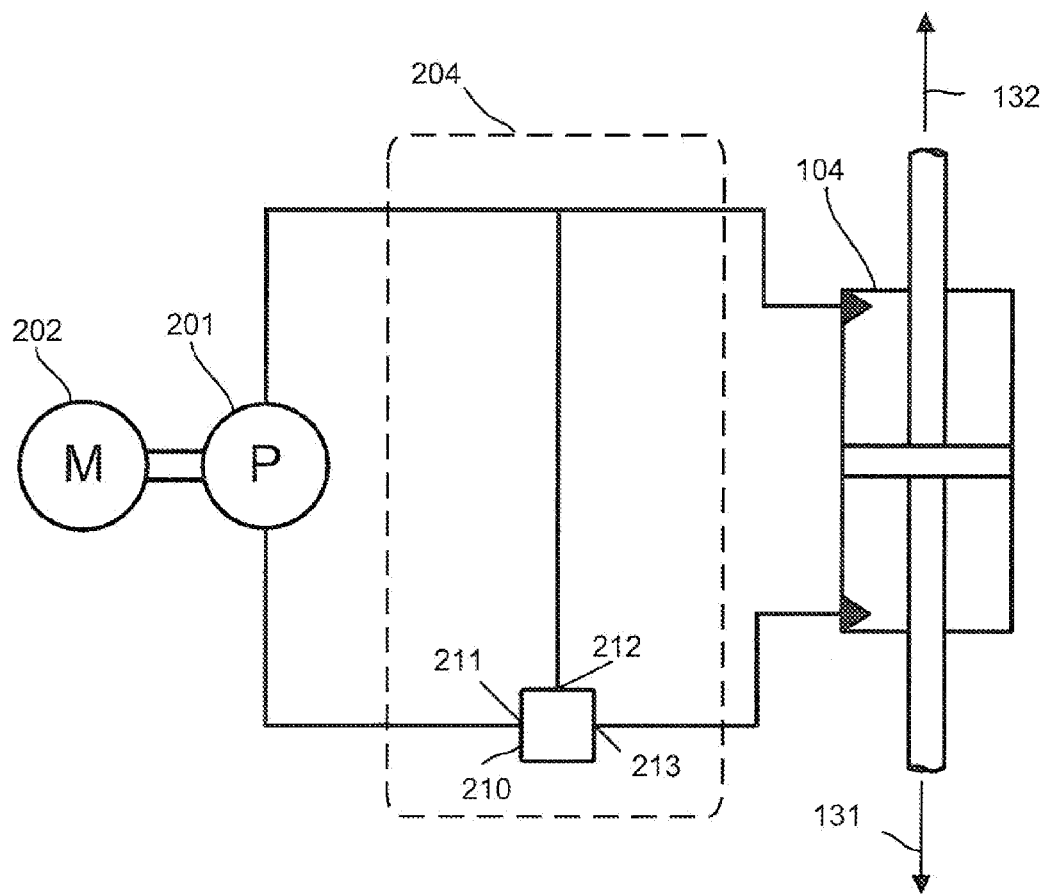
FIG. 12 is a diagram of an alternative hydraulic valve circuit including a three-way valve.

In some embodiments, as shown in FIG. 12, hydraulic valve circuit 204 comprises a three-way valve 210 capable of controlling the hydraulic flow. In operation, when semi-actuated prosthetic knee 100 operates in its actuated mode, three-way valve connects port 211 to port 213 and blocks port 212. This allows for fluid flow between hydraulic pump 201 and torque generator 104 such that the entire hydraulic pump output flow travels to torque generator 104. This further allows signal processor 130 to control torque generator 104 by controlling electric motor 202. The ability to inject power to torque generator 104, in this actuated mode, allows one to control the motion of knee mechanism 107 or impose desirable torque onto knee mechanism 107. When semi-actuated prosthetic knee 100 operates in an un-actuated mode, three-way valve 210 connects port 212 to port 213. Through the use of signal processor 130, one can adjust the opening of port 213 to modulate the resistance of fluid flow in torque generator 104. The ability to modulate the resistance of fluid flow in torque generator 104 allows one to control the resistance of knee mechanism 107 to forces and torques with reduced use of electric power since electric motor 202 is not consuming any electric power in this un-actuated mode. When semi-actuated prosthetic knee 100 operates in a power regenerative mode, three-way valve 210 connects port 211 to port 213 allowing at least a portion of the hydraulic flow from torque generator 104 to turn hydraulic pump 201 while motor controller 128 applies a non-zero current onto electric motor 202 to resist the hydraulic flow in hydraulic pump 201.

Figure 13:
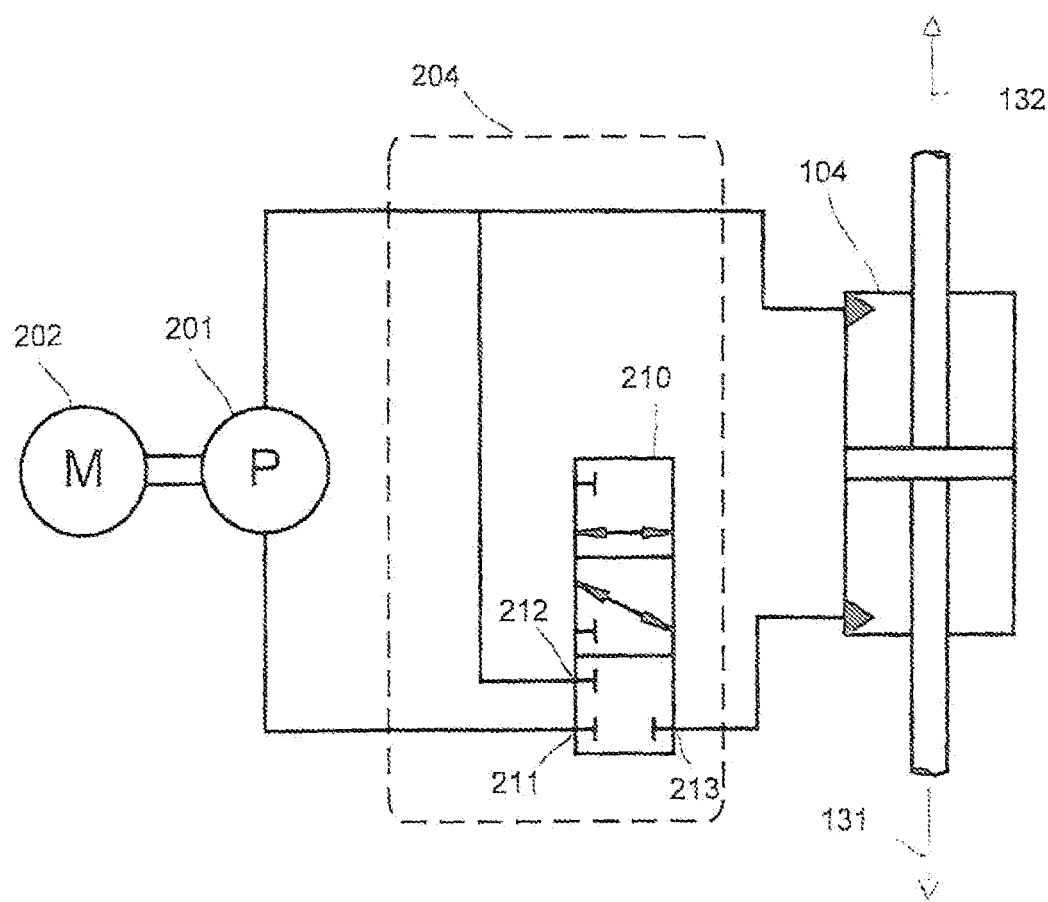
FIG. 13 depicts the three way valve of the hydraulic valve circuit of FIG. 12 in use.

FIG. 13 shows a realization of the embodiment of FIG. 12. More specifically, FIG. 13 shows a three-way valve 210 that has at least three positions. When three-way valve 210 is in its first position, three-way valve connects port 211 to port 213 and blocks port 212. This allows semi-actuated prosthetic knee 100 to operate in actuated mode. When three-way valve 210 is in its second position, it connects port 212 to port 213 and blocks port 211. Through the use of signal processor 130, one can adjust the opening of port 212, port 213 or both port 212 and 213 to modulate and adjust properly the resistance of fluid flow in torque generator 104. When three-way valve 210 is in its third position (shown in FIG. 13), none of the ports are connected to each other.

Figure 14:
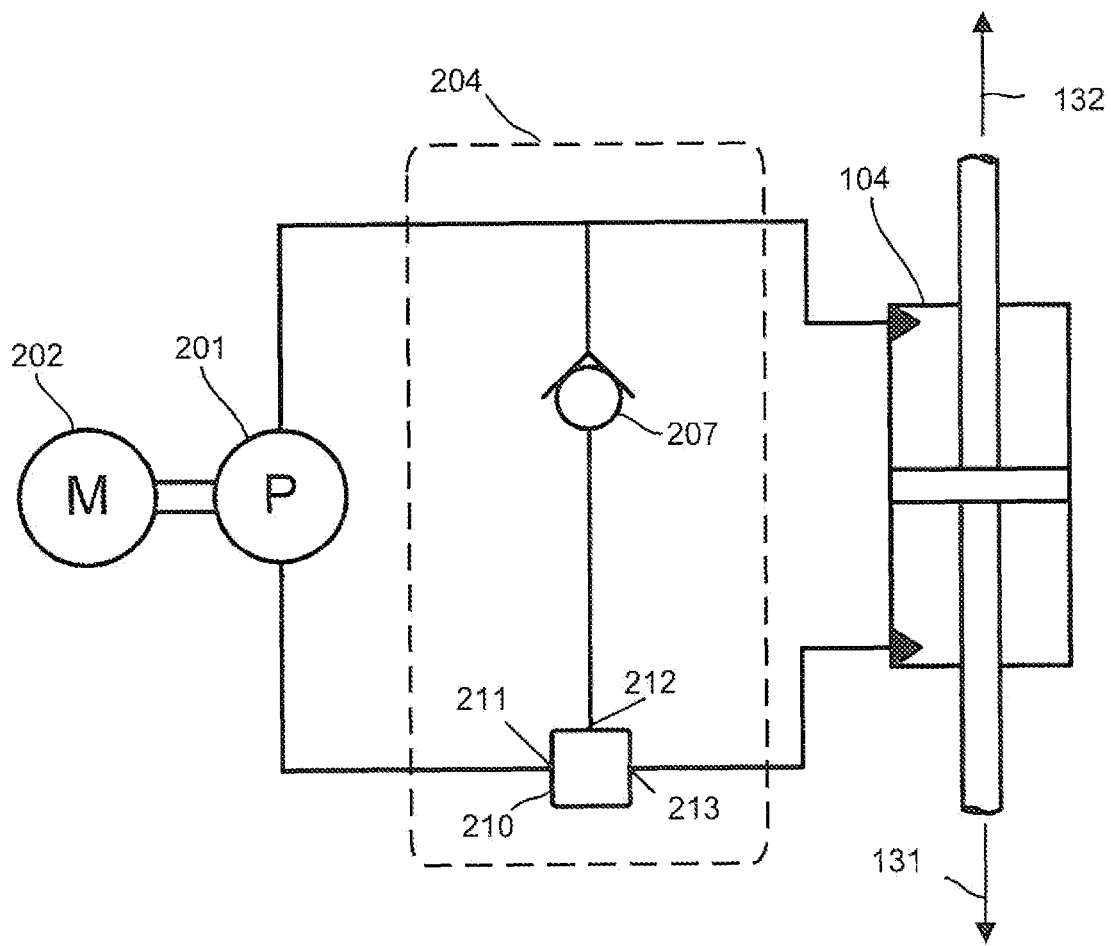
FIG. 14 is a diagram of the hydraulic valve circuit of FIG. 12, further comprising a first check valve.

FIG. 14 shows another embodiment of the embodiment of FIG. 12 where hydraulic valve circuit 204 further comprises a first check valve 207 coupled to port 212. In comparison with the embodiment of FIG. 12, this embodiment constrains the range of resistance of fluid flow in torque generator 104 in flexion direction to always be more than the flow resistance that hydraulic pump 201 creates. It further allows free extension of torque generator 104 if all ports 211, 212 are 213 are connected to each other without compromising the ability to inject power in the extension direction of torque generator 104. When semi-actuated prosthetic knee 100 operates in its actuated mode, three-way valve 210 connects port 211 to port 213 and blocks port 212. This allows for fluid flow between hydraulic pump 201 and torque generator 104 such that the entire hydraulic pump output flow travels to torque generator 104. This further allows signal processor 130 to control the motion of knee mechanism 107 or impose desirable torque onto knee mechanism 107 by controlling electric motor 202.

Figure 15:
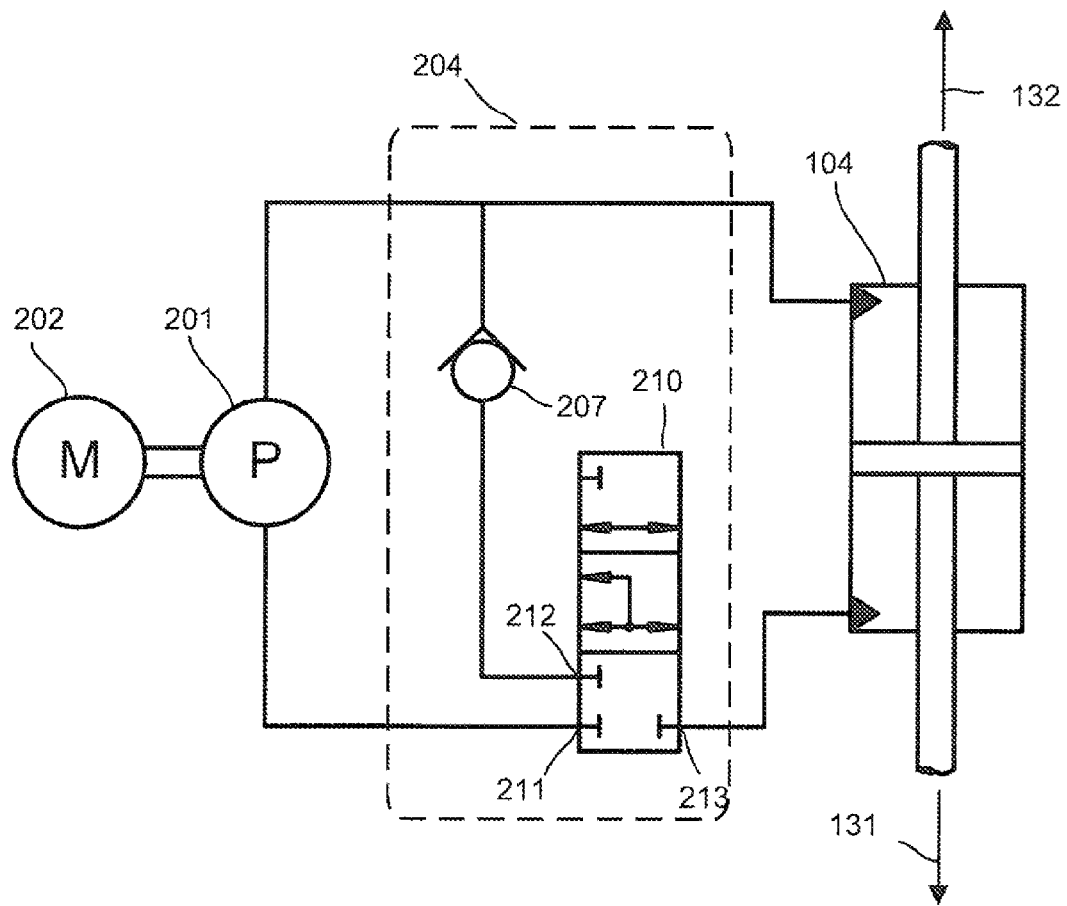
FIG. 15 depicts the three way valve of the hydraulic valve circuit of FIG. 14 in use.

FIG. 15 shows a realization of the embodiment of FIG. 14. FIG. 15 shows a three valve 210 that has at least three positions. When three-way valve 210 is in its first position (actuated mode), three-way valve 210 connects port 211 to port 213 and blocks port 212. When three-way valve 210 is in its second position, all ports are connected to each other. Through the use of signal processor 130, one can adjust the opening of port 212, port 213 or both port 212 and 213 to properly modulate and adjust the resistance of fluid flow in torque generator 104. When three-way valve 210 is in its third position (shown in FIG. 15), none of the ports are connected to each other.

FIG. 16 shows the same embodiment of FIG. 15 with a few added features. A reservoir 230 ensures sufficient oil is in the system in the presence of any leakage or thermal expansion. Two check valves 228 and 229 ensure hydraulic fluid is not pushed back to reservoir 230. Two hydraulic fluid paths 231 and 232 ensure any leakage from the three-way valve 210 and hydraulic pump 201 are fed back to reservoir 230. Pressure sensors 126 and 127 measure the hydraulic fluid pressure in first and second chambers of torque generator 104. A filter 233 collects any contaminants in the fluid.

Figure 17:
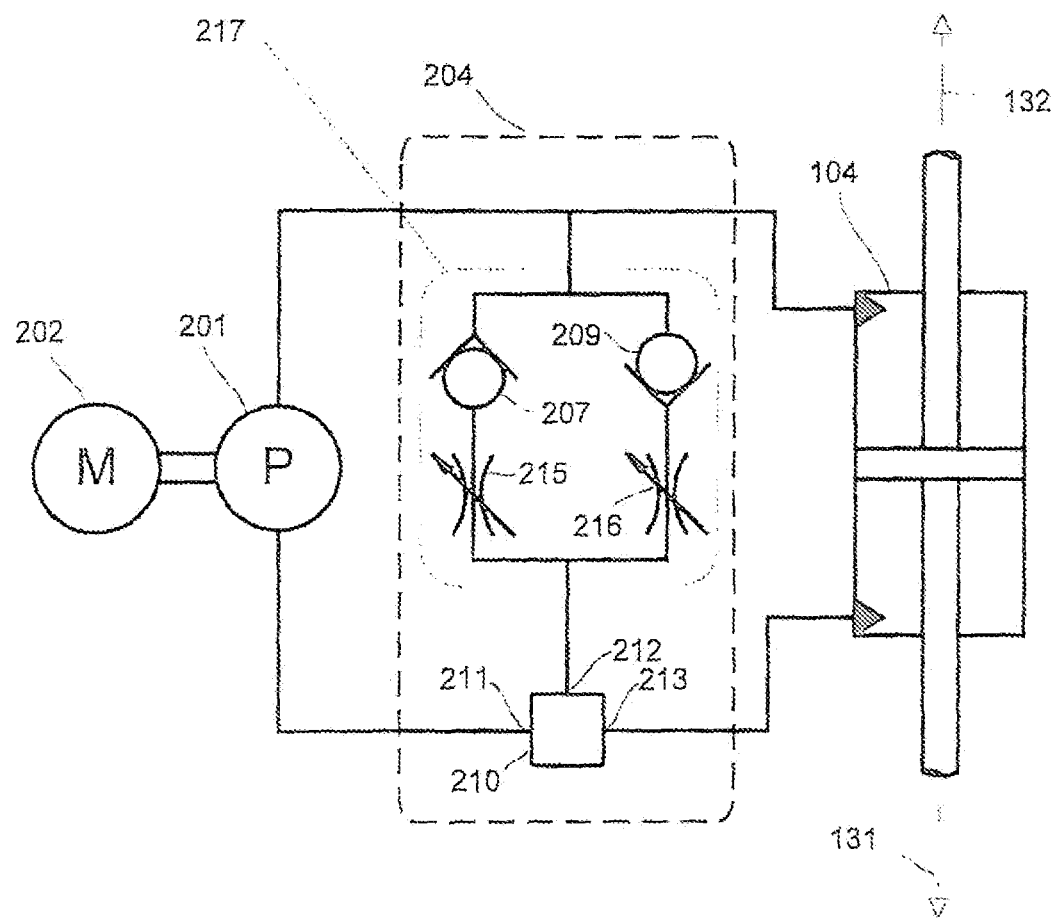
FIG. 17 is a diagram of the hydraulic valve circuit of FIG. 12, further including a parallel path circuit.

FIG. 17 shows another embodiment of FIG. 12 wherein hydraulic valve circuit 204 further comprises a parallel path circuit 217 coupled to port 212. In operation, when semi-actuated prosthetic knee 100 operates in its actuated mode, three-way valve 210 connects port 211 to port 213 and blocks port 212. This allows for fluid flow between hydraulic pump 201 and torque generator 104 such that the entire said hydraulic pump output flow travels to torque generator 104. This further allows signal processor 130 to control torque generator 104 by controlling electric motor 202. The ability to inject power to torque generator 104 in this actuated mode allows one to control the motion of knee mechanism 107 or impose desirable torque onto knee mechanism 107. When semi-actuated prosthetic knee 100 operates in its un-actuated mode, three-way valve 210 connects port 212 to port 213 and blocks port 211. Through the use of signal processor 130, one can adjust the opening of port 213 or port 212 to modulate the resistance of fluid flow in torque generator 104. First adjustable restrictor valve 215 is adjusted to provide resistance to fluid flow in the extension direction of torque generator 104. Second adjustable restrictor valve 216 is adjusted to provide resistance to fluid flow in the flexion direction of torque generator 104. The ability to modulate the resistance of fluid flow in torque generator 104 allows one to control the resistance of knee mechanism 107 to forces and torques with reduced use of electric power since electric motor 202 is not consuming any electric power in this un-actuated mode.

Figure 18:
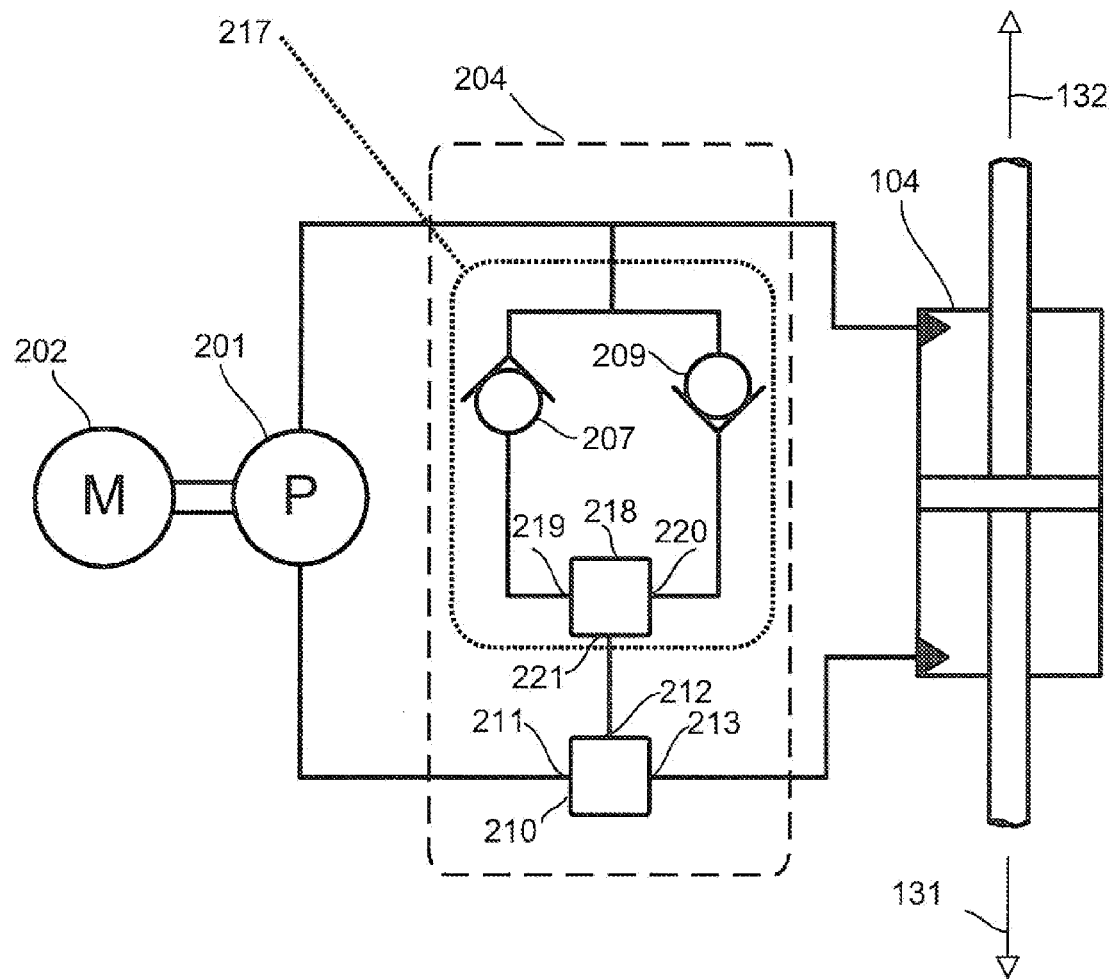
FIG. 18 is a diagram of an alternative hydraulic valve circuit including a second three-way valve.

FIG. 18 shows another embodiment of hydraulic valve circuit 204. The embodiment of FIG. 18 is the same as the embodiment of FIG. 17 except adjustable restrictor valves 215 and 216 are replaced by a second three-way valve 218. In operation when semi-actuated prosthetic knee 100 operates in an actuated mode, three-way valve 210 connects port 211 to port 213 and blocks port 212. This allows for fluid flow between hydraulic pump 201 and torque generator 104 such that the entire hydraulic pump output flow travels to torque generator 104. This further allows signal processor 130 to control torque generator 104 by controlling electric motor 202. When semi-actuated prosthetic knee 100 operates in an un-actuated mode, first three-way valve 210 connects port 212 to port 213. Second three-way valve 218 modulates the resistance to hydraulic flow between a port 219 and a port 221 when torque generator 104 moves in the extension direction and modulates the resistance to hydraulic flow between a port 220 and port 221 when torque generator 104 moves in the flexion direction. This embodiment allows free extension of torque generator 104 without compromising the ability to inject power in the extension direction of torque generator 104 if port 219 and port 221 are connected and port 220 is blocked and if ports 211, 212 and 213 are connected to each other. This embodiment further allows free flexion of torque generator 104 without compromising the ability to inject power in the flexion direction of torque generator 104 if port 220 and port 221 are connected and port 219 is blocked and if ports 211, 212 and 213 are connected to each other.

Figure 19:
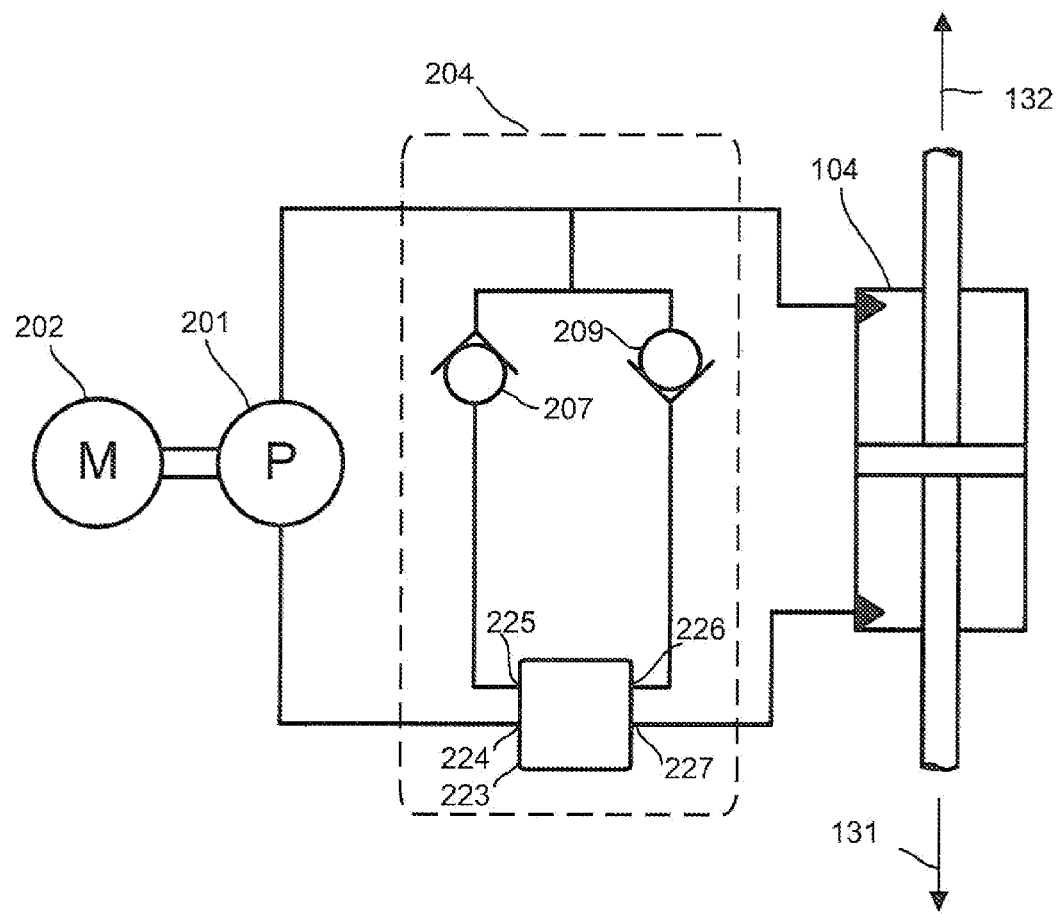
FIG. 19 is a diagram of an alternative hydraulic valve circuit including a four-way valve.

FIG. 19 shows another embodiment of hydraulic valve circuit 204. The embodiment of FIG. 19 is the same as the embodiment of FIG. 18 except two three-way valves 210 and 218 are replaced by a four way valve 223. In operation when semi-actuated prosthetic knee 100 operates in an actuated mode, four-way valve 223 connects a port 224 to a port 227 and blocks ports 225 and 226. This allows for fluid flow between hydraulic pump 201 and torque generator 104 such that the entire said hydraulic pump output flow travels to torque generator 104. This further allows signal processor 130 to control torque generator 104 by controlling electric motor 202. When semi-actuated prosthetic knee 100 operates in an un-actuated mode, four-way valve 223 modulates the resistance to hydraulic flow between port 225 and port 227 when torque generator 104 moves in the extension direction and modulates the resistance to hydraulic flow between port 226 and port 227 when torque generator 104 moves in the flexion direction. This embodiment allows free extension of torque generator 104 without compromising the ability to inject power in the extension direction of torque generator 104 if ports 224, 225, and 227 are connected and port 226 is blocked. This embodiment further allows free flexion of torque generator 104 without compromising the ability to inject power in the flexion direction of torque generator 104 if ports 224, 226, and 227 are connected and port 225 is blocked.

As can be seen from FIGS. 1 through 19, hydraulic power unit 200 comprises two paths that connect to torque generator 104: one through hydraulic pump 201 and the second through a hydraulic valve circuit 204. In the actuated mode, hydraulic pump 201 hydraulically couples to torque generator 104. In un-actuated mode, the flow to torque generator 104 is modulated by at least one valve.

Figure 20:
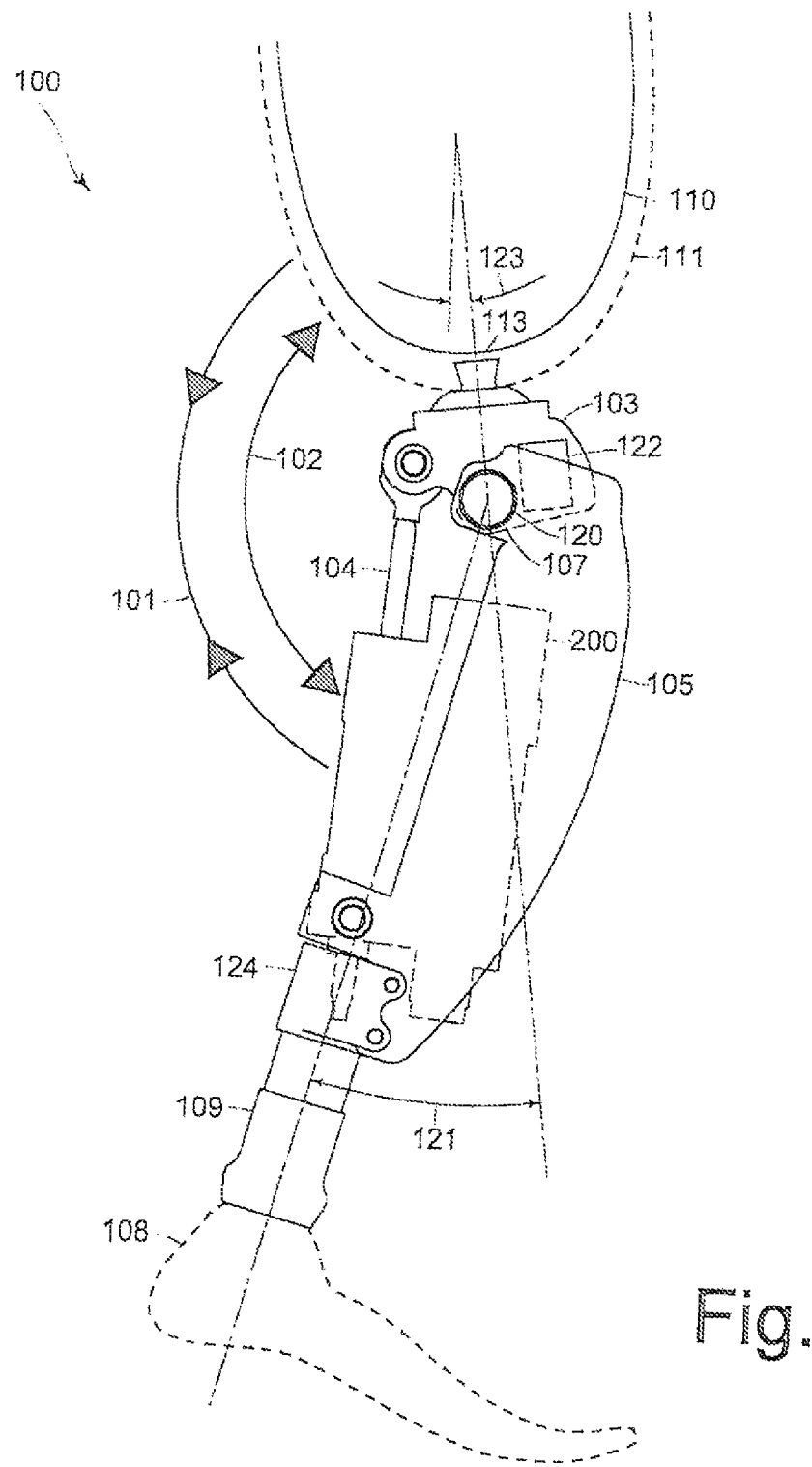
FIG. 20 is a side view of the semi-actuated prosthetic knee of FIG. 1.

FIG. 20 represents the schematic of one embodiment of semi-actuated prosthetic knee 100. As previously noted, semi-actuated prosthetic knee 100, among other components, comprises a thigh link 103, a shank link 105, and a knee mechanism 107, coupled by torque generator 104. Knee mechanism 107 is configured to allow movement of thigh link 103 relative to shank link 105 along flexion direction 101 and extension direction 102. Semi-actuated prosthetic knee 100 is configurable to be coupled to an above-knee amputee's remaining lower limb 110 through a socket 111. More specifically, socket 111 is coupled to thigh link 103 with a pyramid adapter 113 or similar adapter known in the art. An ankle pylon 109 connects shank link 105 to artificial foot 108 through stance sensor 124. Knee angle sensor 120 measures an angle 121 between thigh link 103 and shank link 105. Thigh angle sensor 122 located on thigh link 103 measures an absolute angle 123 of thigh link 103. The profile of hydraulic power unit 200 is shown in FIG. 20.

Figure 21:
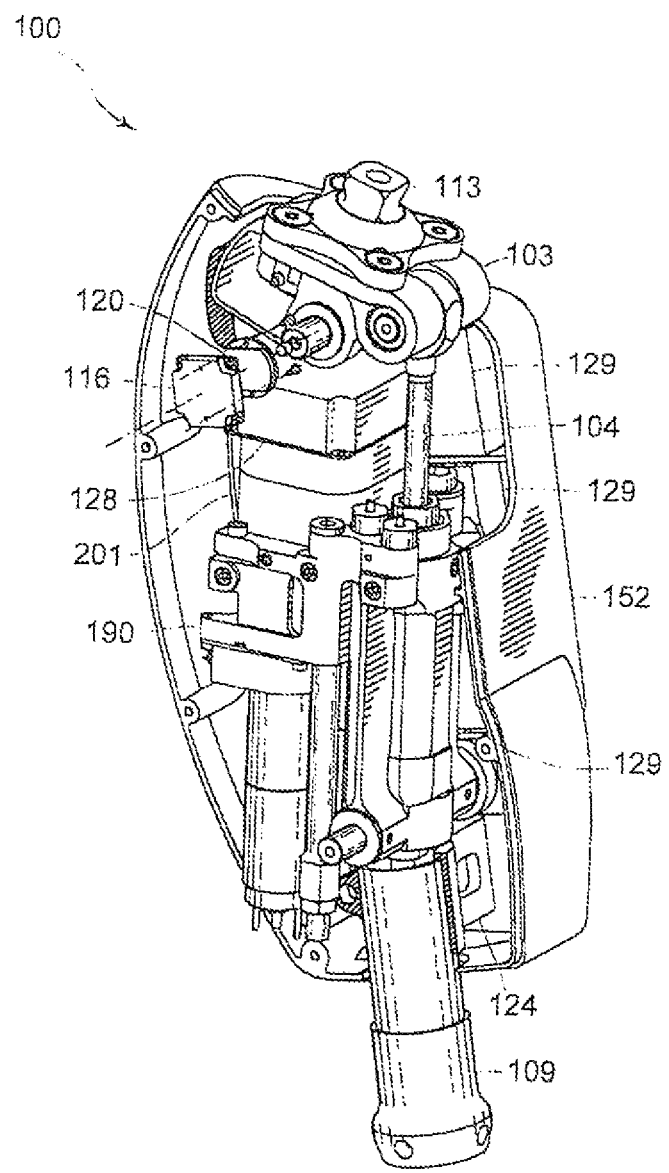
FIG. 21 is a more detailed perspective view of the semi-actuated prosthetic knee of FIG. 20.

FIGS. 21 and 22 represent a cutaway perspective drawing and exploded view of the semi-actuated prosthetic knee 100 presented in FIG. 20. In the embodiment of FIGS. 21 and 22, pyramid adapter 113 connects to thigh link 103. Thigh angle sensor 122 fixed to thigh link 103 comprises an accelerometer 133 and a gyroscope 134. A shaft 118 extending from thigh link 103 is stationary with respect to thigh link 103. Knee angle sensor 120 is in the form of a magnetic encoder fixed to an encoder housing 116 and stationary with respect to shank link 105. Magnetic encoder 120 measures the angle of a magnet 119 embedded in shaft 118. Shaft 118 is secured to thigh link 103 and turns inside needle bearings 135. Thrust bushings 136 provide axial support between thigh, link 103 and knee mechanism 107. A bearing cover 115 protects needle bearing 135. Hydraulic power unit 200 comprises, among other elements, motor controller 128, hydraulic pump 201, a hydraulic manifold 190, torque generator 104 and pressure sensors 126 and 127. Power unit 200 pivots with respect to shank link 105 on needle bearings 137. Thrust bushings 138 provide axial support between power unit 200 and shank link 105. Torque generator 104 couples to thigh link 103 through needle bearings 139 to complete the linkage between thigh link 103, shank link 105, and torque generator 104. Stance sensor 124 connects shank link 105 to ankle pylon 109. Batteries 129 are used to provide electric power for the prosthetic knee 100.

Figure 23:
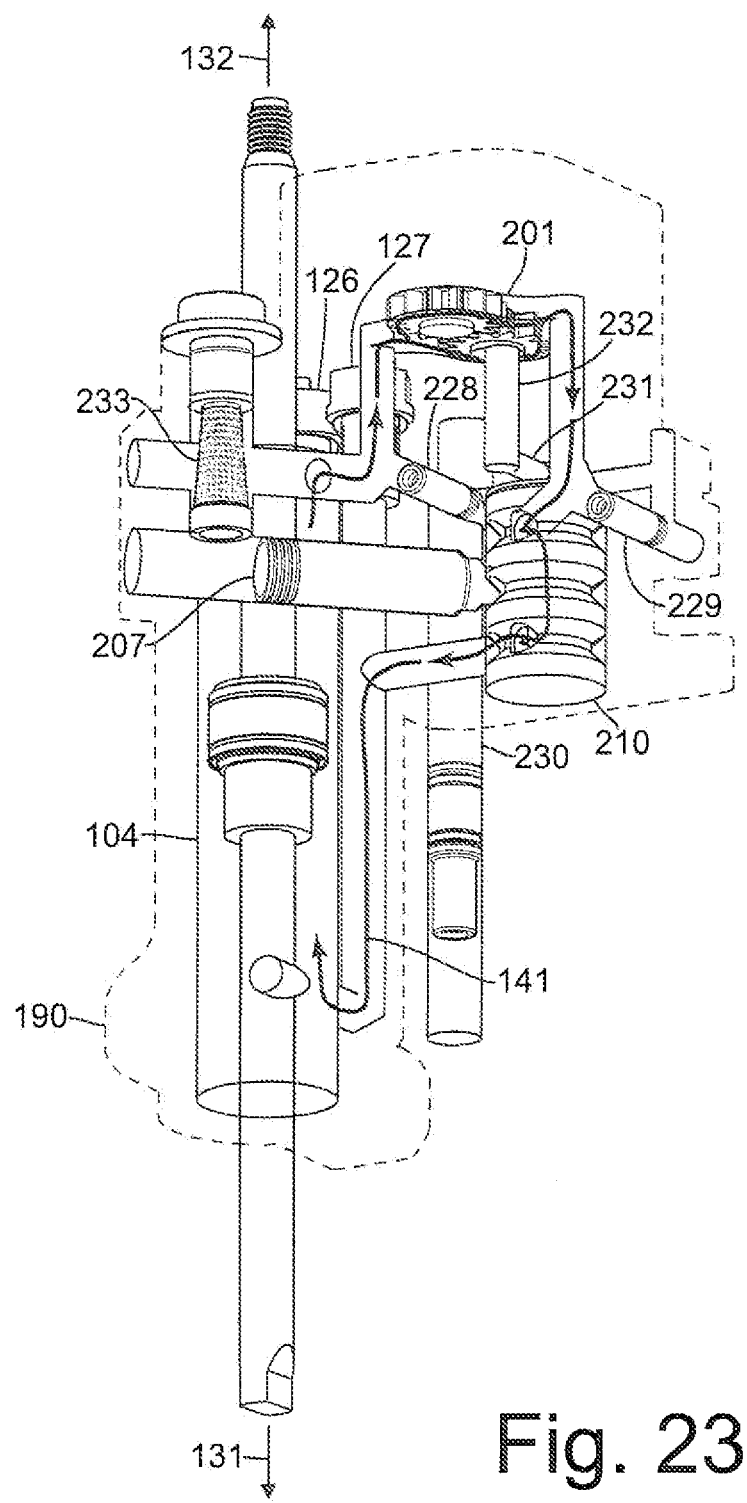
FIG. 23 is a partial perspective view of the hydraulic valve circuit of FIG. 16 with fluid flow during an actuated mode in extension.
Figure 24:
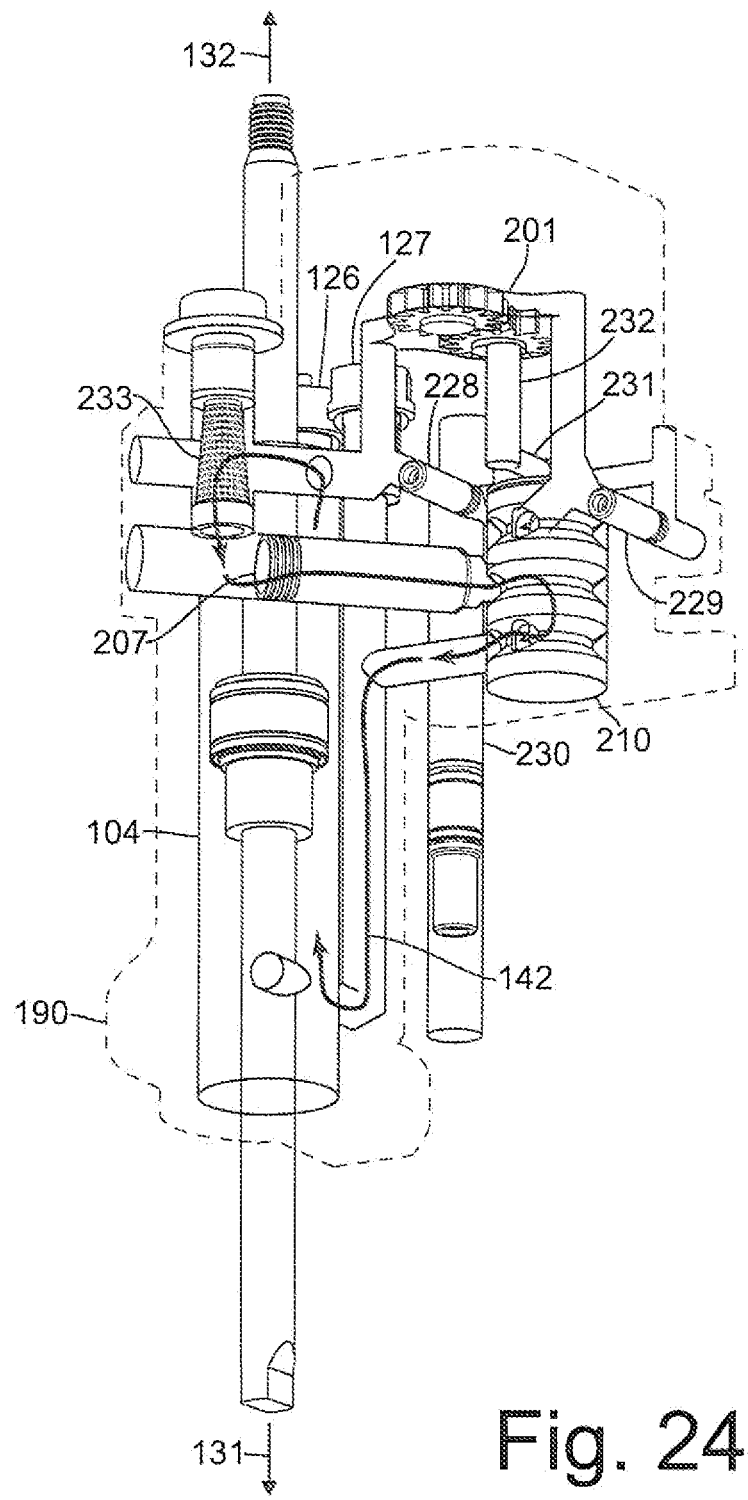
FIG. 24 is a partial perspective view of the hydraulic valve circuit of FIG. 16 with fluid flow during an un-actuated mode in extension.

FIG. 23 shows a perspective drawing of the hydraulic valve circuit shown in FIG. 16. An arrow 141 represents the path of hydraulic flow during an actuated mode in extension direction represented by arrow 132. Three-way valve 210 incorporates three ports 211, 212, and 213 (depicted in FIG. 16) that connect to hydraulic pump 201, check valve 207 and torque generator 104, respectively. Check valves 228 and 229 prevent the fluid flow back to reservoir 230. Hydraulic fluid paths 231 and 232 define passages from hydraulic pump 201 and three-way hydraulic valve 210 to reservoir 230. FIG. 24 also shows a perspective drawing of the hydraulic valve circuit of FIG. 16, where an arrow 142 shows the path of the hydraulic flow during un-actuated mode in extension direction.

Figure 25:
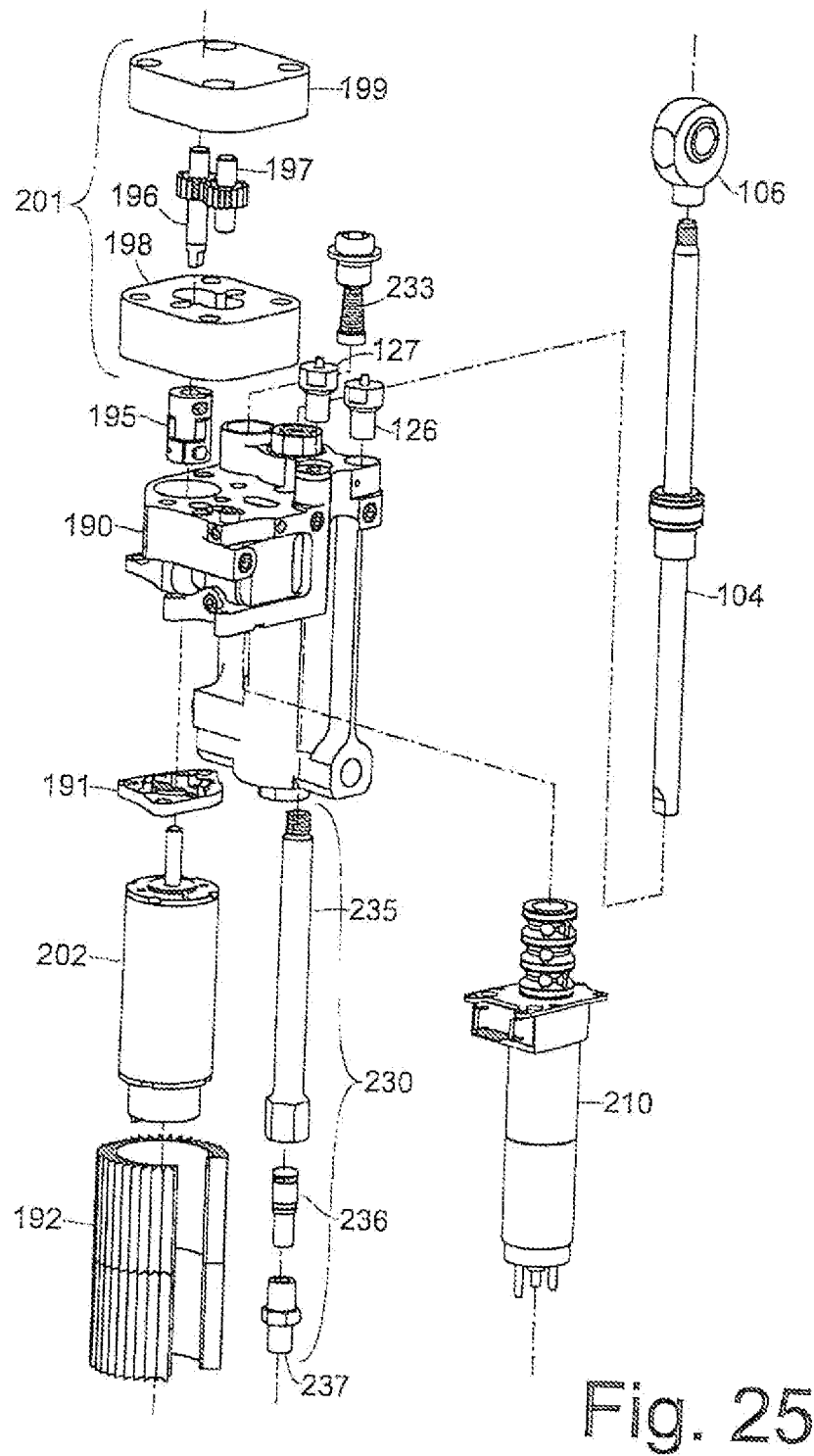
FIG. 25 is an exploded view of the power unit in FIG. 1.

FIG. 25 shows the exploded view of hydraulic power unit 200. Hydraulic pump 201 includes a pump cover 199 and a pump base 198. A driver gear 196 is coupled to electric motor 202 through a coupler 195. A driven gear 197 of hydraulic pump 201 is engaged to driver gear 196. Manifold 190 includes all hydraulic passages. Reservoir 230 includes an air/fluid divider 236 and an air valve 237. Air valve 237 allows for pressurizing the air in reservoir 230. A heat sink 192 allows for heat transfer from electric motor 202. Pressure sensors 126 and 127 measure the hydraulic pressure in two chambers of the torque generator 104. A rod end 106 connects torque generator 104 to thigh link 103. Components labeled 191 and 235 are a motor mounting plate and a reservoir housing, respectively.

Figure 26:
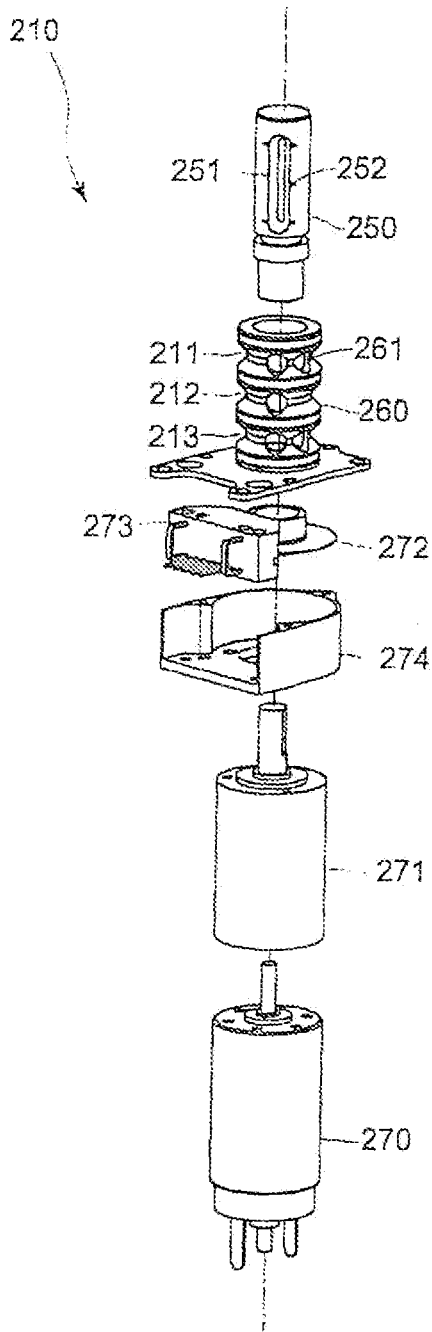
FIG. 26 is an exploded view of the three-way valve of FIG. 25.
Figure 27:
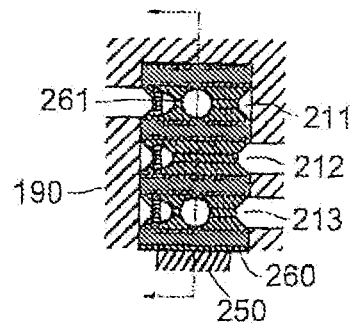
FIG. 27 is a partial cross-sectional side view of the three-way valve of FIG. 26 in a first position.
Figure 28:
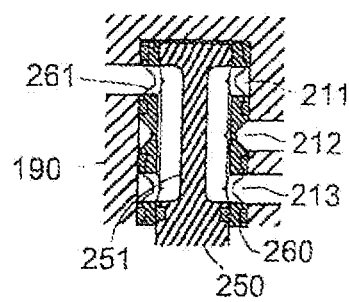
FIG. 28 is a partial cross-sectional side view of the three-way valve of FIG. 26 in a second position.
Figure 29A:
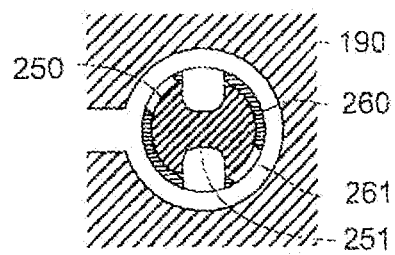
FIG. 29A is a partial cross-sectional top view of the three-way valve of FIG. 26 in a first position.
Figure 29B:
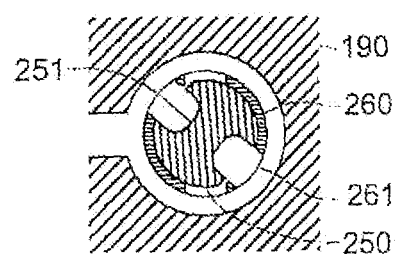
FIG. 29B is a partial cross-sectional top view of the three-way valve of FIG. 26 in a second position.
Figure 29C:
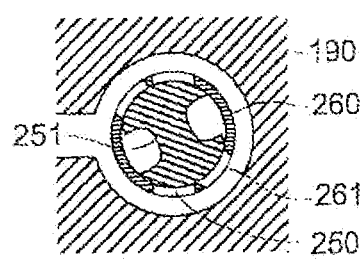
FIG. 29C is a partial cross-sectional top view of the three-way valve of FIG. 26 in a third position.
Figure 29D:
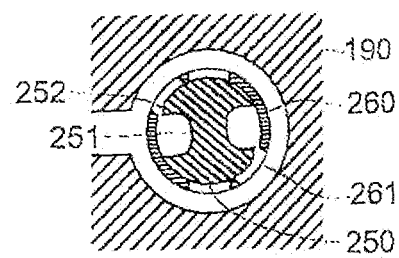
FIG. 29D is a partial cross-sectional top view of the three-way valve of FIG. 26 in a fourth position.

FIG. 26 describes the details of three-way valve 210. A valve electric motor 270 is coupled to a valve transmission 271. An encoder, which includes an encoder housing 274, an encoder disk 272 and an encoder read head 273, measures the valve position. A valve housing 260 has three ports 211, 212, and 213. In this embodiment, there are five orifices 261 in valve housing 260. A valve barrel 250 is coupled to valve transmission 271 output shaft. Two slots 251 are created in valve barrel 250 as shown in FIGS. 26 and 28. As valve barrel 250 is turned by valve electric motor 270, three-way valve 210 assumes one of at least three positions described by FIG. 16. As shown in FIG. 29A, when three-way valve 210 is in its first position, port 211 and port 213 are fully open to each other. When three-way valve 210 is in its second position (FIG. 29B), port 211, port 212 and port 213 are connected. When three-way valve 210 is in its third position (FIG. 29C), no ports are connected. As can be seen from FIG. 26 and FIG. 29D there are some notches 252 on slot 251 that allow for controllable openings of the ports. Needless to say, valve barrel 250 can be in other positions besides positions depicted in FIG. 29A-D. To obtain the desired resistance to fluid flow, the valve can be adjusted by signal processor in real time to achieve optimal performance.

Figure 30:
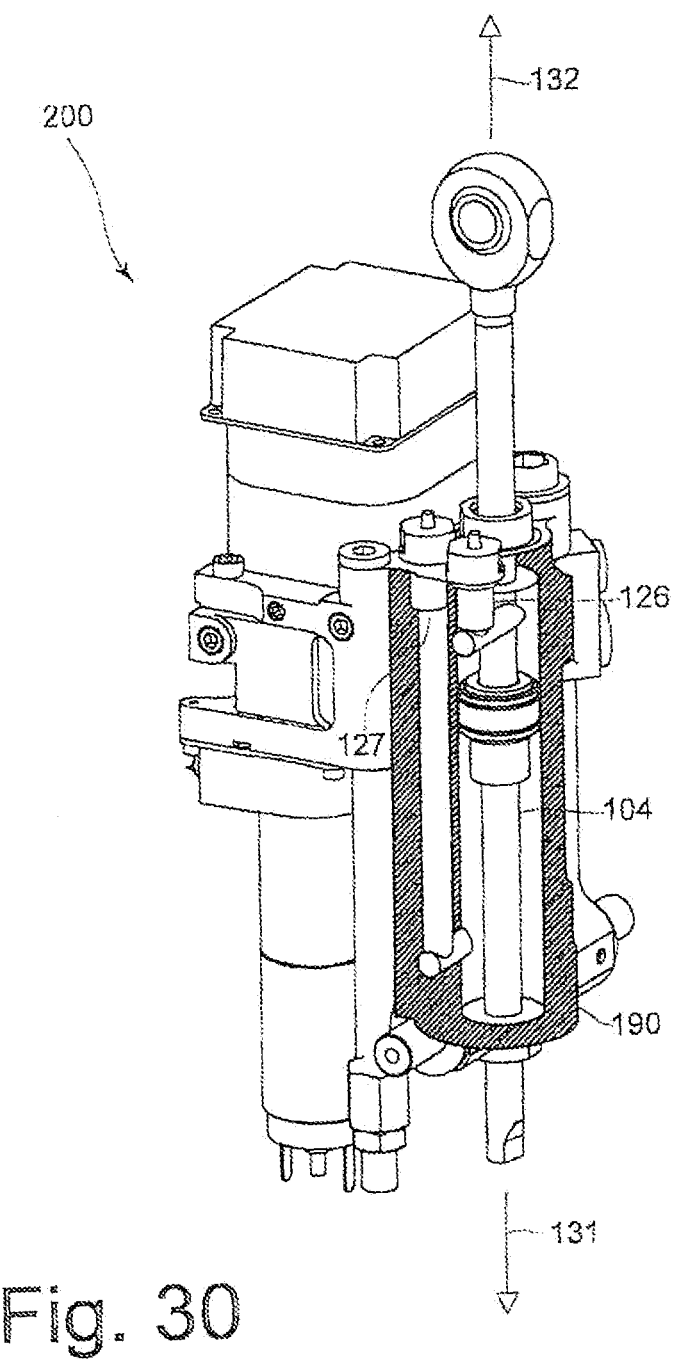
FIG. 30 is a partial cross-sectional view of a hydraulic power circuit of the present invention.

FIG. 30 represents an embodiment of semi-actuated prosthetic knee 100 where pressure sensors 126 and 127 measure the hydraulic pressure on both sides of torque generator 104. Additionally, FIG. 30 represents an embodiment of hydraulic power unit 200 where hydraulic manifold 190 is shown cut away so that connection paths between torque generator 104 and pressure sensors 126 and 127 are visible.

Figure 31:
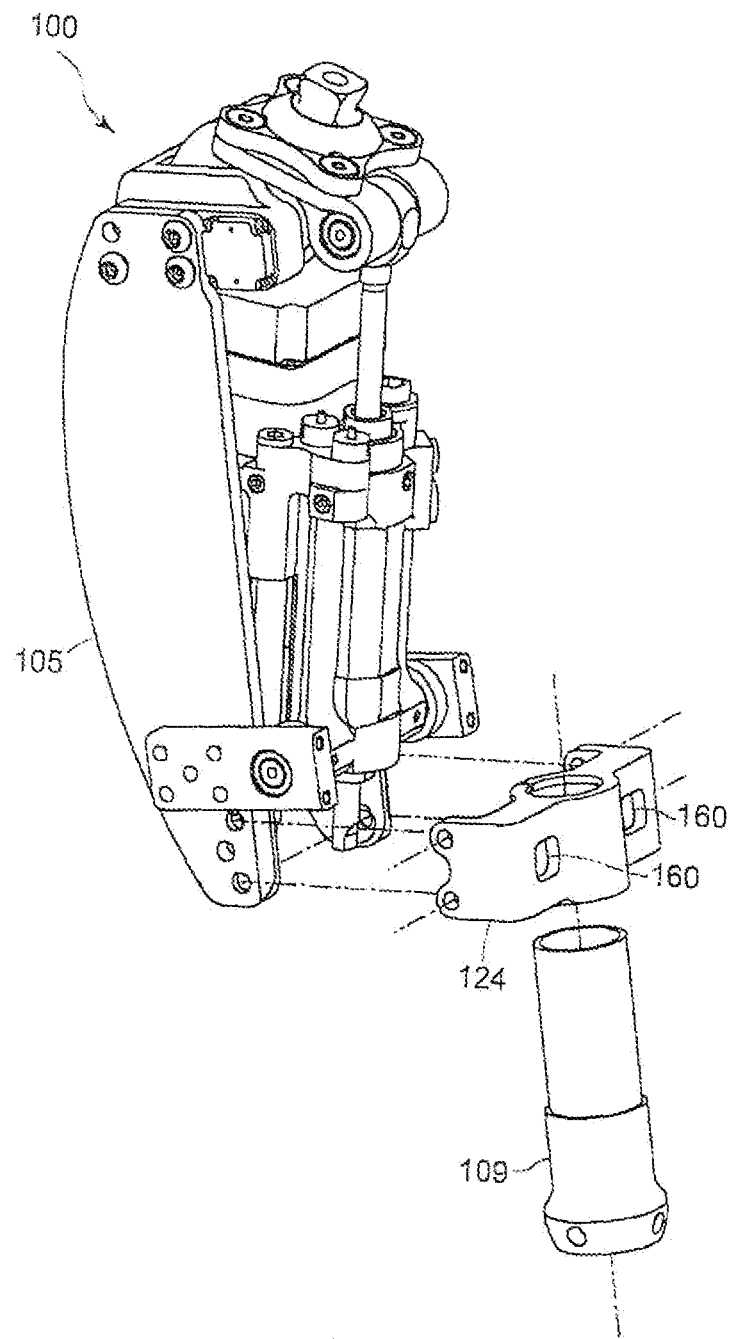
FIG. 31 is a partial exploded view of the semi-actuated knee of FIG. 20.
Figure 32A:
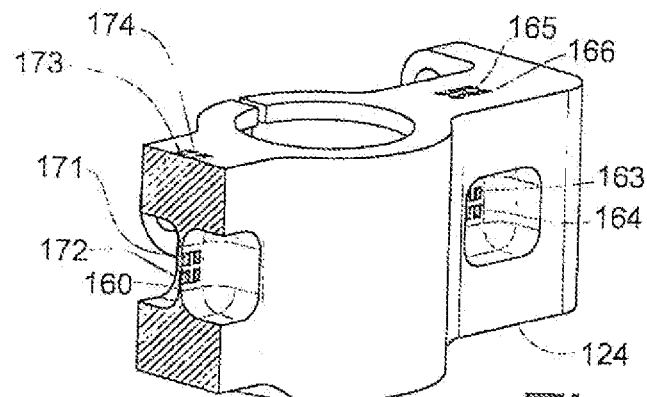
FIG. 32A is a partial cross-sectional back perspective view of a stance sensor of the present invention.
Figure 32B:
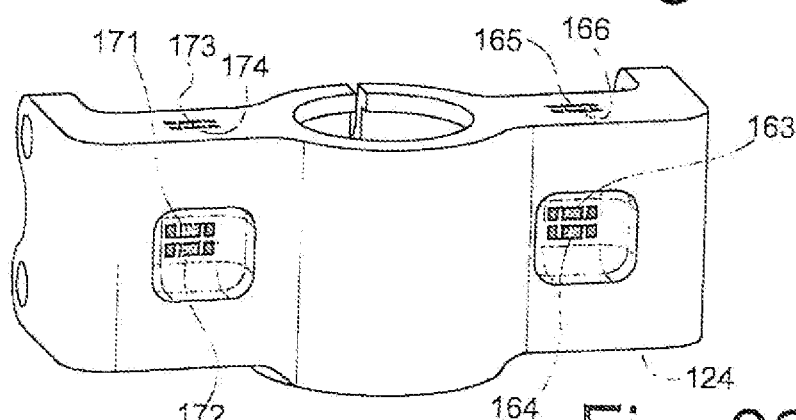
FIG. 32B is a back perspective view of the stance sensor of FIG. 32A.
Figure 32C:
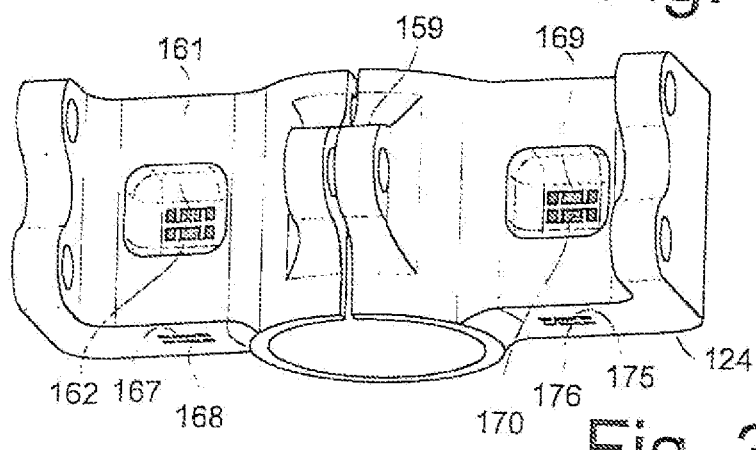
FIG. 32C is a front perspective view of the stance sensor of FIG. 32A.

FIG. 31 shows the implementation of stance sensor 124 in the embodiment of semi-actuated knee 100 shown in FIG. 20. Stance sensor 124 connects ankle pylon 109 to shank link 105. In this embodiment, stance sensor 124 is instrumented with several strain gages 161-172 to measure forces and moments transmitted through shank link 105 during stance phase. FIGS. 32A-32C shows the locations of strain gages 161-172 on stance sensor 124. Stance sensor 124 comprises a tube clamp 159 as depicted in FIG. 32C that clamps to ankle pylon 109.

Strain gages 161, 162, 163, 164 are electrically connected in a wheatstone bridge configuration to measure the vertical shear strains in a shear web 160 due to vertical forces on one of the webs. Strain gages 169, 170, 171, 172 are electrically connected in a wheatstone bridge configuration to measure the vertical shear strain in the second shear web. Summing the vertical shear measurements from both webs 160 cancels out frontal plane moments which might contaminate the vertical shear measurements. Strain gages 165, 166, 167, 168 are electrically connected in a wheatstone bridge configuration to measure the shear strains due to sagittal plane moment loads on the right side of stance sensor 124. Strain gages 173, 174, 175, 176 are electrically connected in a wheatstone bridge configuration to measure the shear strains due to sagittal plane moment loads on the left side of stance sensor 124. Summing the moment load measurements from the left and right sides of stance sensor 124 cancels out rotational moments which might contaminate the sagittal moment measurements. Since rotational moments on stance sensor 124 are small in normal operation in comparison with sagittal plane moments, strain gages 165, 166, 167, 168 or strain gages 173, 174, 175, 176 may be electrically connected in an alternative wheatstone bridge configuration to measure horizontal shear strains due to horizontal forces on the right or left side of stance sensor 124.

FIG. 33 shows semi-actuated prosthetic knee 100 where covers 151 and 152 are removed.

Figure 34:
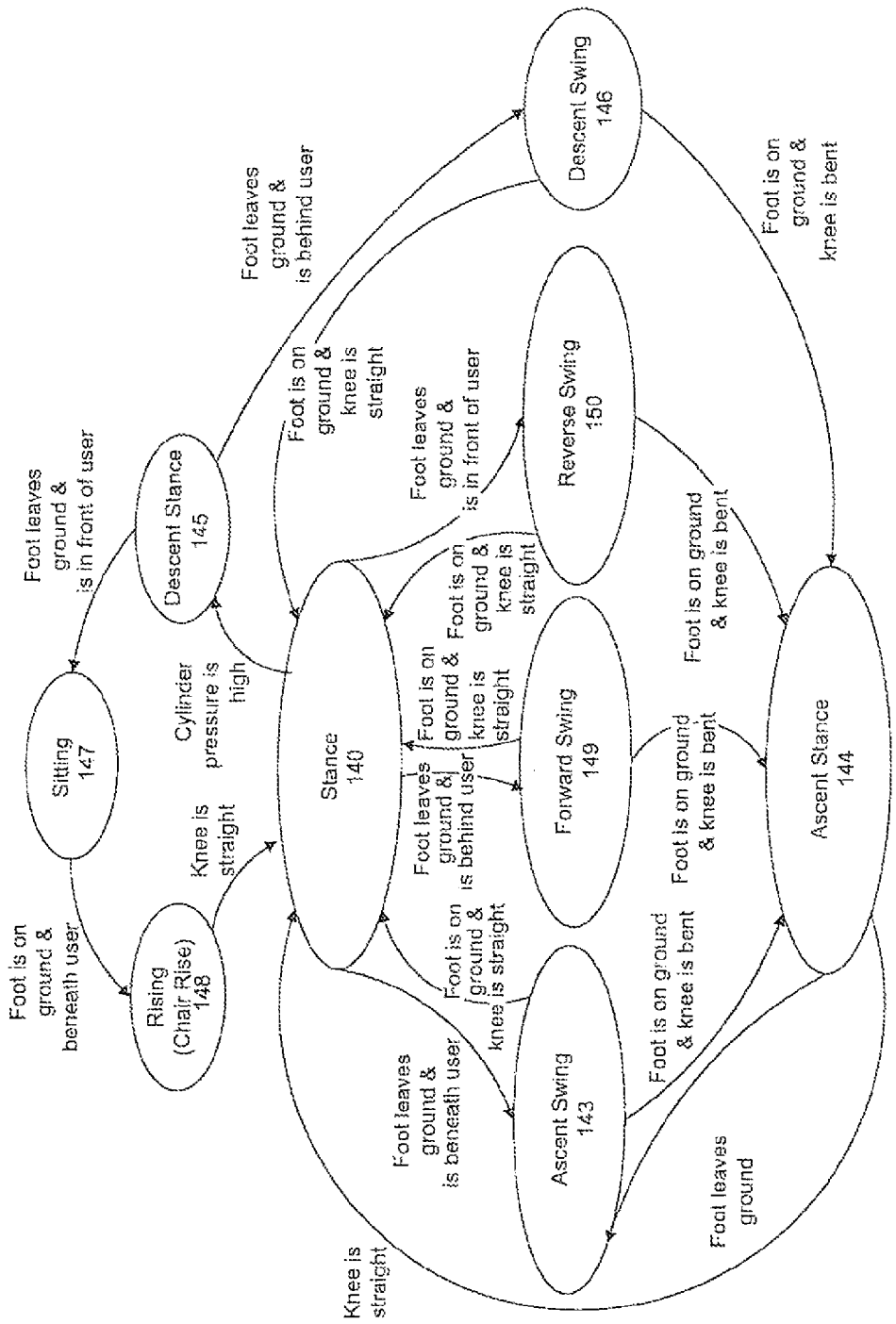
FIG. 34 is a diagram of states implemented by a signal processor in accordance with the invention.

In some embodiments, signal processor 130 receives information from various sensors and implements various controllers onto the knee. These controllers are referred to as "states" in this document. FIG. 34 is a diagram of states implemented by signal processor 130. All states are labeled. The arrows show the conditions under which signal processor 130 moves the prosthetic knee from one state to another. Below the states and the conditions to move to that state is described.

Stance

In operation, signal processor 130 begins to implement a stance state 140 when stance sensor 124 indicates that artificial foot 108 has contacted the ground as depicted in FIG. 20. In some embodiments of the invention, during a portion of stance state 140, semi-actuated prosthetic knee 100 operates in the un-actuated mode. This means that during this portion of stance state 140 where semi-actuated prosthetic knee 100 operates in the un-actuated mode, semi-actuated prosthetic knee 100 is configured such that no electric power from electric power source 205 is transferred to electric motor 202 and hydraulic valve circuit 204 modulates the resistance of the fluid flow in torque generator 104. The ability to modulate the resistance of fluid flow in torque generator 104 allows one to control the resistance of knee mechanism 107 to forces and torques during a portion of stance state 140, which reduced use of electric power since electric motor 202 is not consuming any electric power in this un-actuated mode.

In some embodiments of the invention when stance sensor 124 indicates that the heel of artificial foot 108 is taking more load than the toe of artificial foot 108, hydraulic power unit 200 imposes a greater resistance to fluid flow in torque generator 104 than of when stance sensor 124 indicates that the toe of artificial foot 108 is taking more load than the heel of artificial foot 108.

Forward Swing

In some embodiments of the invention, signal processor 130 begins to implement a forward swing state 149 when semi-actuated prosthetic knee 100 is operating in stance state 140 and signal processor 130 learns that artificial foot 108 has separated from the ground generally behind the amputee's trunk. In some embodiments of the invention, during a portion of forward swing state 149, semi-actuated prosthetic knee 100 operates in the actuated mode. This means during this portion of forward swing 149 where semi-actuated prosthetic knee 100 operates in the actuated mode, semi-actuated prosthetic knee 100 is configured such that it transfers electric power from electric power source 205 to electric motor 202 powering electric motor 202 and hydraulic pump 201. In this actuated mode, hydraulic valve circuit 204 is configured such that hydraulic pump 201 hydraulically couples to torque generator 104 such that the entire hydraulic pump output flow travels to torque generator 104. This hydraulic coupling between hydraulic pump 201 and torque generator 104 allows signal processor 130 to control torque generator 104 directly by controlling electric motor 202. The ability to inject power to torque generator 104 allows one to control the motion of knee mechanism 107 or impose desirable torque onto knee mechanism 107 during a portion or entire forward swing state 149.

In some embodiments of the invention, during a portion of forward swing state 149, signal processor 130 controls the angle between thigh link 103 and shank link 105 such that artificial foot 108 follows a trajectory. In some other embodiments of the invention, during a portion of forward swing state where prosthetic knee 100 operates in the actuated mode, signal processor 130 controls the angle between thigh link 103 and shank link 105 as a function of thigh angle signal 156 (depicted in FIG. 1) such that artificial foot 108 follows a trajectory. This allows the amputee to move artificial foot 108 forward and backward (i.e. change direction) during swing and have artificial foot 108 on a trajectory. In some embodiments, the trajectory for artificial foot 108 is a straight line generally parallel to the ground. It should be understood that one can use a shank angle sensor in conjunction with knee angle sensor 120 to arrive at thigh angle signal 156. In more detailed embodiment of the invention, during a portion of forward swing state 149 where prosthetic knee 100 operates in the actuated mode, signal processor 130 controls the angle between thigh link 103 and shank link 105 first as a function of thigh angle signal 156 and then as a function of time. For example in some embodiments, after regulating artificial foot 108 on a trajectory up to a point that artificial foot 108 is in front of the amputee's body, signal processor 130 extends the knee in a time suitable for the current walking speed. In some other embodiments of the invention, during a portion of forward swing state 149 where prosthetic knee 100 operates in the actuated mode, signal processor 130 controls the angle between thigh link 103 and shank link 105 such that the absolute angle of shank link 105 follows a trajectory.

Reverse Swing

In some embodiments of the invention, signal processor 130 begins to implement a reverse swing state 150 when semi-actuated prosthetic knee 100 is operating in stance state 140 and signal processor 130 learns that artificial foot 108 has separated from the ground in front of the amputee's trunk. In some embodiments of the invention, during a portion of reverse swing state 150, semi-actuated prosthetic knee 100 operates in the actuated mode.

This means that during this portion of reverse swing, the ability to inject power to torque generator 104 allows one to control the motion of knee mechanism 107 or impose desirable torque onto knee mechanism 107 during a portion or entire reverse swing state 150.

In some embodiments of the invention, during a portion of reverse swing state 150, signal processor 130 controls the angle between thigh link 103 and shank link 105 such that artificial foot 108 follows a trajectory. In some other embodiments of the invention, during a portion of reverse swing state 150 where semi-actuated prosthetic knee 100 operates in the actuated mode, signal processor 130 controls the angle between thigh link 103 and shank link 105 as a function of thigh angle signal 156 such that artificial foot 108 follows a trajectory. This allows the amputee to move artificial foot 108 forward and backward (i.e. change direction) during reverse swing 150 and have artificial foot 108 on a trajectory. In some embodiments, the trajectory for artificial foot 108 is a straight line generally parallel to the ground. Again, it should be understood that one can use a shank angle sensor in conjunction with knee angle sensor 120 to arrive at thigh angle signal 156. In a more detailed embodiment of the invention, during a portion of reverse swing state 150 where prosthetic knee 100 operates in the actuated mode, signal processor 130 controls the angle between thigh link 103 and shank link 105 first as a function of thigh angle signal 156 and then as a function of time. For example in some embodiments, after regulating artificial foot 108 on a trajectory up to a point that artificial foot 108 is behind the amputee's body, signal processor 130 extends the knee in a time suitable for walking backwards. In some other embodiments of the invention, during a portion of reverse swing state 150 where prosthetic knee 100 operates in the actuated mode, signal processor 130 controls the angle between thigh link 103 and shank link 105 such that the absolute angle of shank link 105 follows a trajectory.

Ascent Swing

In some embodiments of the invention, signal processor 130 begins to implement an ascent swing state 143 when semi-actuated prosthetic knee 100 is operating in stance state 140 and signal processor 130 learns that said artificial foot 108 just separated from the ground generally beneath the amputee's trunk. In some embodiments of the invention, during a portion of ascent swing state 143, semi-actuated prosthetic knee 100 operates in the actuated mode. This means during this portion of ascent swing state 143 where semi-actuated prosthetic knee 100 operates in the actuated mode prosthetic knee 100 is configured such that it transfers electric power from electric power source 205 to electric motor 202 turning electric motor 202 and hydraulic pump 201.

In some embodiments of the invention, during a portion of ascent swing state 143, signal processor 130 controls the angle between thigh link 103 and shank link 105 such that artificial foot 108 follows a trajectory. In some other embodiments of the invention, during a portion of ascent swing state signal processor 130 controls the angle between thigh link 103 and shank link 105 as a function of thigh angle signal 156 such that artificial foot 108 follows an arbitrary trajectory. This allows the amputee to move artificial foot 108 up and down (i.e. change direction) during ascent swing and have artificial foot 108 on a trajectory. In some embodiments, the trajectory for artificial foot 108 is a path that moves up and then forward in order to place the artificial foot on top of a stair step. Again, it should be understood that one can use a shank angle sensor in conjunction with knee angle sensor 120 to arrive at thigh angle signal 156. In some other embodiments of the invention, during a portion of ascent swing state 143 where prosthetic knee 100 operates in the actuated mode, signal processor 130 controls the angle between thigh link 103 and shank link 105 such that the absolute angle of shank link 105 follows a trajectory or maintains a constant value.

Ascent Stance

In some embodiments of the invention, signal processor 130 begins to implement an ascent stance state 144 when stance sensor 124 indicates that artificial foot 108 has contacted the ground with the knee angle substantially bent. During a portion of this ascent stance state 144, semi-actuated prosthetic knee 100 operates in the actuated mode.

In some embodiments of the invention, during a portion of ascent stance state 144, signal processor 130 controls the angle between thigh link 103 and shank link 105 such that the knee angle follows a trajectory. In some other embodiments of the invention, during a portion of ascent stance state 144, signal processor 130 controls the torque generated by torque generator 104. In some further embodiments of the invention, during a portion of ascent stance state 144, signal processor 130 controls the current to electric motor 202. In some other embodiments of the invention, during a portion of ascent stance state 144, signal processor 130 controls the speed of electric motor 202.

In some embodiments of the invention, signal processor 130 begins to implement an ascent swing state 143 when semi-actuated prosthetic knee 100 is operating in ascent stance state 144 and signal processor 130 learns that said artificial foot 108 just separated from the ground (regardless of the position of the foot). Signal processor 130 begins to implement a stance state 140 when semi-actuated prosthetic knee 100 is operating in ascent stance state 144 and knee angle signal 155 indicates that semi-actuated prosthetic knee 100 is not bent.

Descent Stance

In some embodiments of the invention, signal processor 130 begins to implement a descent stance state 145 when semi-actuated prosthetic knee 100 is operating in stance state 140 and the torque in torque generator 104 is larger than a particular value. During descent stance state 145, the user intends to bend semi-actuated prosthetic knee 100 and that causes an increase in the torque of torque generator 104. In one embodiment, pressure sensors 126 and 127 are used to measure the force in torque generator 104, thereby reflecting the torque associated in torque generator 104. In some embodiments of the invention, signal processor 130 begins to implement a descent stance state 145 when semi-actuated prosthetic knee 100 is operating in stance state 140 and pressure sensors 126 and 127 indicate high pressure difference between first and second torque generator chambers. In some embodiments of the invention, during a portion of descent stance state 145, semi-actuated prosthetic knee 100 operates in the un-actuated mode.

This means during this portion of descent stance state 145 where semi-actuated prosthetic knee 100 operates in the un-actuated mode, semi-actuated prosthetic knee 100 is configured such that no electric power from electric power source 205 is transferred to electric motor 202 and hydraulic valve circuit 204 modulates the resistance of the fluid flow in torque generator 104. The ability to modulate the resistance of fluid flow in torque generator 104 allows one to control the resistance of knee mechanism 107 to forces and torques during a portion of descent stance state 145 with reduced use of electric power since electric motor 202 is not consuming any electric power in this un-actuated mode.

In some embodiments the semi-actuated prosthetic knee 100 includes a power regenerative mode, which is used during descent stance state 145. In this mode, pump valve 203 is not closed allowing at least a portion of the hydraulic flow from torque generator 104 to turn hydraulic pump 201 and the motor controller forces electric motor 202 to generate electric power. This could be accomplished in a number of ways which are not hydraulic as well.

Descent Swing

In some embodiments of the invention, signal processor 130 begins to implement a descent swing state 146 when signal processor 130 learns that during descent stance state 145 artificial foot 108 just separated from the ground and is positioned behind the amputee's trunk. In some embodiments of the invention, during a portion of descent swing state 145, semi-actuated prosthetic knee 100 operates in the actuated mode.

In some embodiments of the invention, during a portion of descent swing state 145, signal processor 130 controls the angle between thigh link 103 and shank link 105 such that artificial foot 108 follows a trajectory. In some other embodiments of the invention, during a portion of ascent swing state signal processor 130 controls the angle between thigh link 103 and shank link 105 as a function of thigh angle signal 156 such that artificial foot 108 follows a trajectory. In a more detailed embodiment of the invention, during a portion of descent swing state 146 where prosthetic knee 100 operates in the actuated mode, signal processor 130 controls the angle between thigh link 103 and shank link 105 first as a function of thigh angle signal 156 and then as a function of time. For example in some embodiments, after regulating artificial foot 108 on a trajectory up to a point that artificial foot 108 is estimated to have cleared a standard stair, signal processor 130 extends the knee in a time suitable for walking down stairs. In some other embodiments of the invention, during a portion of descent swing state 146 where prosthetic knee 100 operates in the actuated mode, signal processor 130 controls the absolute angle of shank link 105 to follow an arbitrary trajectory.

Sitting

In some embodiments of the invention, signal processor 130 begins to implement a sitting state 147 when signal processor 130 learns that during descent stance state 145 artificial foot 108 just separated from the ground in front of the amputee's trunk. In some embodiments of the invention, during a portion of sitting state 147, semi-actuated prosthetic knee 100 operates in the un-actuated mode. This means during this portion of sitting state 147 where semi-actuated prosthetic knee 100 operates in the un-actuated mode, semi-actuated prosthetic knee 100 is configured such that no electric power from electric power source 205 is transferred to electric motor 202 and hydraulic valve circuit 204 modulates the resistance of the fluid flow in torque generator 104 so prosthetic knee 100 flexes smoothly with little or no resistance. The ability to modulate the resistance of fluid flow in torque generator 104, allows one to control the resistance of knee mechanism 107 to forces and torques during a portion of stance state 140 with reduced use of electric power since electric motor 202 is not consuming any electric power in this un-actuated mode.

Rising (Chair Rise)

In some embodiments of the invention, signal processor 130 begins to implement a rising state 148 when stance sensor 124 indicates that, during sitting state 147, artificial foot 108 has contacted the ground beneath the amputee. During a portion of this rising state 148 semi-actuated prosthetic knee 100 operates in the actuated mode. In some embodiments of the invention, during a portion of rise state 148, signal processor 130 controls the angle between thigh link 103 and shank link 105 such that the knee angle follows a trajectory. In some other embodiments of the invention, during a portion of rise state 148, signal processor 130 controls the torque generated by torque generator 104. In some further embodiments of the invention, during a portion of rise state 148, signal processor 130 controls the current to electric motor 202. In some other embodiments of the invention, during a portion of rise state 148, signal processor 130 controls the speed of electric motor 202.

Figure 35:
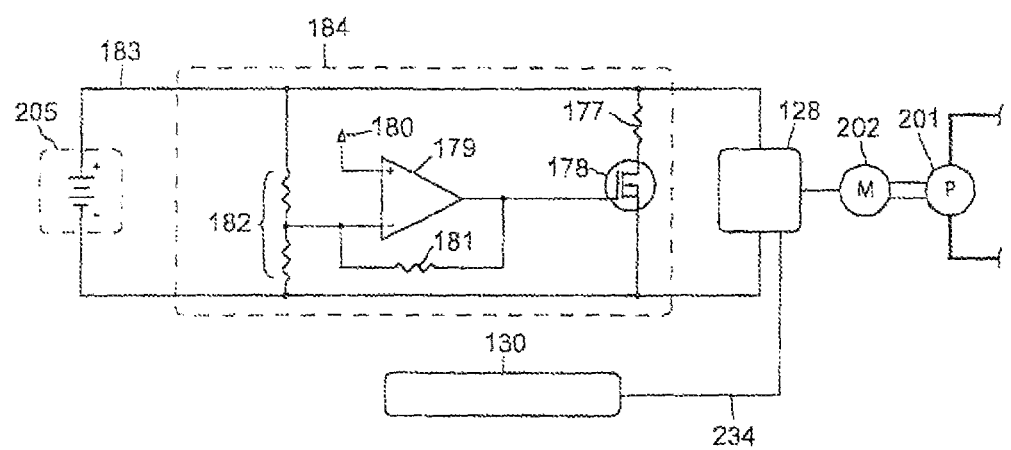
FIG. 35 is an electrical schematic showing the connection of an electric power source to a motor controller.

FIG. 35 is an electrical schematic showing the connection of electric power source 205 to motor controller 128, including an overcharge protection circuit 184. In power regenerative mode, hydraulic fluid flows through hydraulic pump 201, which causes electric motor 202 to turn and generate electricity. The signal processor 130, commands a desired current to the motor controller 128, which increases the voltage of a bus 183 such that energy flows from the electric motor 202 into the power source 205, thus regenerating power. If the bus voltage becomes sufficiently high, a voltage divider 182 causes a comparator 179 to turn on a switch 178 which diverts regenerating current away from power source 205 and instead dissipates a fraction of the energy in a power resistor 177. A voltage reference 180 sets the trip point for the comparator 179 and a feedback resistor 181 provides hysteresis.

The foot trajectory described above in connection with a prosthesis can be applied to lower extremity human exoskeletons. Just as the prosthetic knee described above controls the knee angle based on the thigh angle signal, in a lower extremity exoskeleton, the motion controller can coordinate the motion of multiple actuated joints using the same technique. As a result the motion controller will need to define multiple constraints for determining the desired joint trajectories. The goal of the technique is to use the coordinated motion of the joints to control the motion of the foot 301 relative to the ground 313. For the purposes of explanation, the description will focus on the embodiment of this device as single leg 309 with controlled hip 308 and knee joints 306. This is in no way meant to limit the applicability of this invention to only lower extremity exoskeletons with two controlled joints. For example, other lower extremity exoskeletons to which this technique appliesarean embodiment with actuated hip, knee and ankle joints or one with actuated hip and knee joints on two legs.

One embodiment of this invention coordinates the hip 308 and knee joints 306 of the swing leg 310 to meet two constraints where at least one of those constraints are Cartesian conditions of the position of the foot 301. The constraints that place Cartesian conditions on the foot relative to the ground are referenced as Cartesian constraints. When controlling the position of the foot, the specific embodiment can be configured to focus on any portion of the foot such as but not limited to the toe, the heel, the ball or the ankle of the foot 301. The point on the foot 301 selected to control the position of will be referred to under the general name of "ground contact point" to encompass these possible embodiments. This is significant because in mobile bipedal robotics, the trajectories for the swing leg 310 are typically planned offline in the form of predefined hip and knee angle trajectory constraints and do not take into account the position of the foot 301 relative to the ground 313.

The technique of predefining joint angle trajectories has worked well in previous autonomous bipedal robotics because the device has complete control over all aspects of the entire pose of the robot. In exoskeleton devices, the user maintains a significant ability to impact the pose of the device so it must use trajectories that are invariant to the pose the user creates. The inventors have discovered that predefining joint trajectories is difficult to use in a lower extremity exoskeleton because the user can vary the posture of the device with respect to the earth by leaning it backward and forward. That means that a predefined hip and knee angle trajectory may result in the foot 301 striking the ground 313 during mid swing if the user leans the device 309 forward, and it may result in a step terminating in mid air if the user leans the device 309 backwards. Therefore a system that controls the position of the foot 301 with respect to the ground 313 is much easier to use, especially for a novice user. As a result, the presented technique is valuable for allowing a mixture of Cartesian constraints and joint angle constraints that can be predefined without being affected by the pose of the device.

Figure 36:
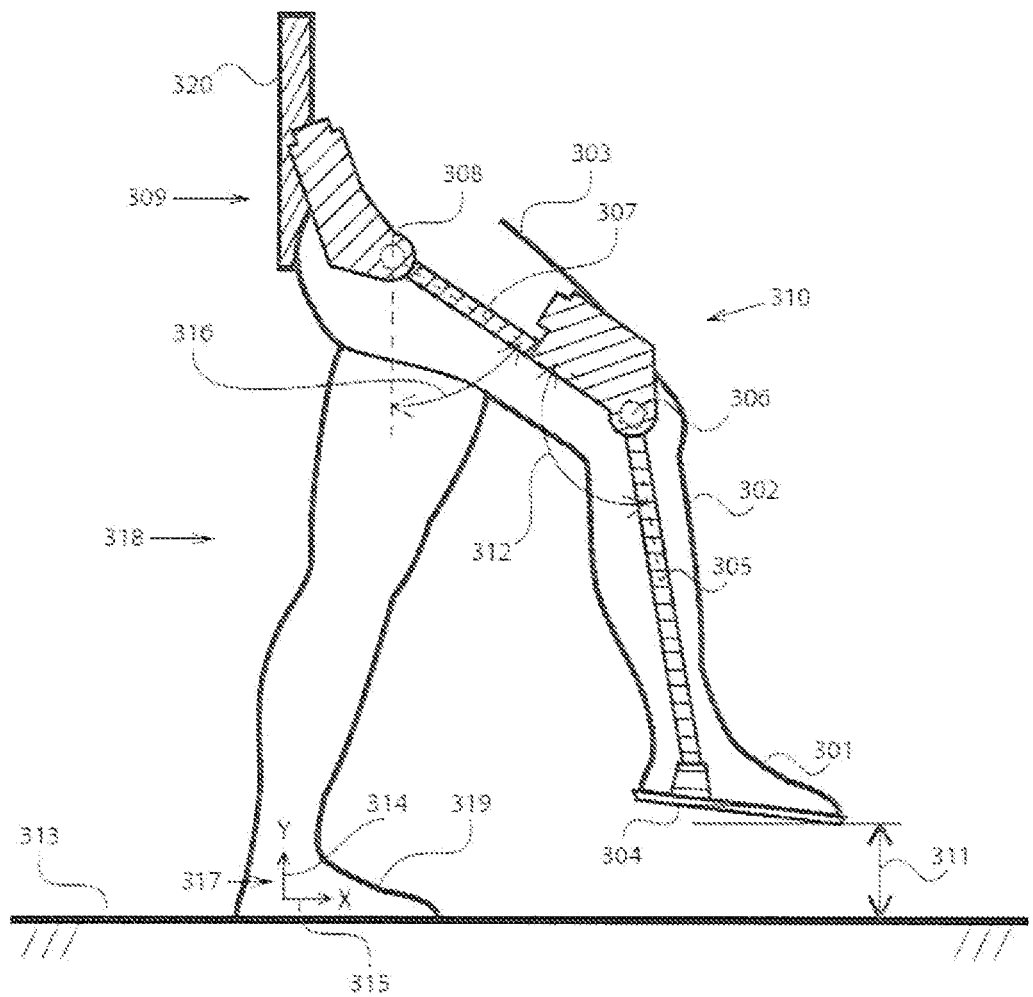
FIG. 36 is a schematic view of an exoskeleton system employing foot trajectory capabilities in accordance with an aspect of the invention.
Figure 37:
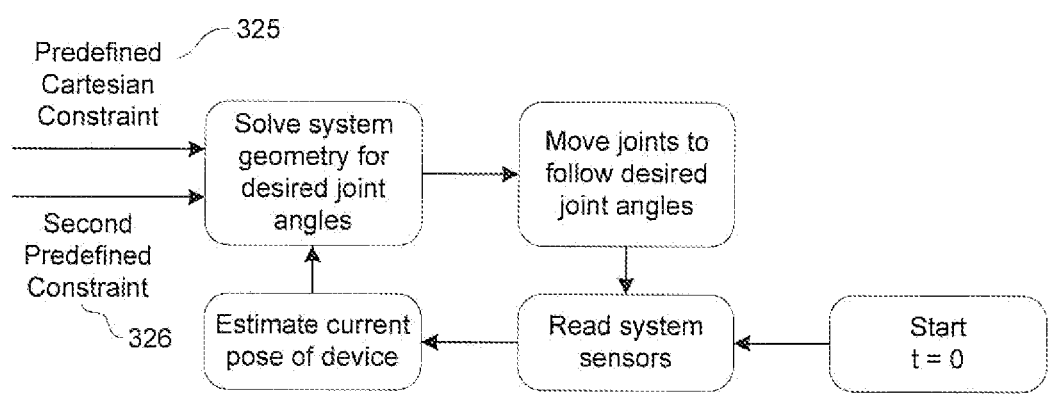
FIG. 37 sets forth a flow chart associated with the system of FIG. 36.

In one such embodiment, the invention can be configured to maintain a desired toe height trajectory relative to the ground and a desired knee angle trajectory as can be seen in FIG. 36. To do this the invention calculates a current pose estimate which estimates the positions of the exoskeleton links 305 and 307 with respect to the ground 313. The motion controller then uses the active feedback to the system provided by the sensors and pose estimate to calculate the specific hip 316 and knee angles 312 required to meet the constraints and moves the hip 308 and knee 306 joints to those positions. FIG. 36 shows a predefined Cartesian constraint 325, the desired toe elevation 311, and a second predefined constraint 326 is shown in the flow chart of FIG. 37. In this case second predefined constraint 326 defines the desired knee angle 312. The remaining hip angle 316 for the swing leg 310 can then be solved to satisfy these two constraints using many techniques known to one who is skilled in the art. FIG. 37 shows the order in which measurements are used to make calculations.

There are many other embodiments of this invention that are similar but incorporate different constraints. Often, it is desirable for the predefined constraints to not be constant and instead to vary throughout the step with respect to time or another step parameter. A set of constraints as it varies throughout the step is referred to as a trajectory. The method equally applies to other embodiments with a combination of vertical 314, or horizontal 315 Cartesian constraints and knee 312 or hip joint 316 angles constraints on the swing leg 310. A Cartesian constraint is defined as a constraint that describes a Cartesian condition on the position of the foot 301.

Figure 38:
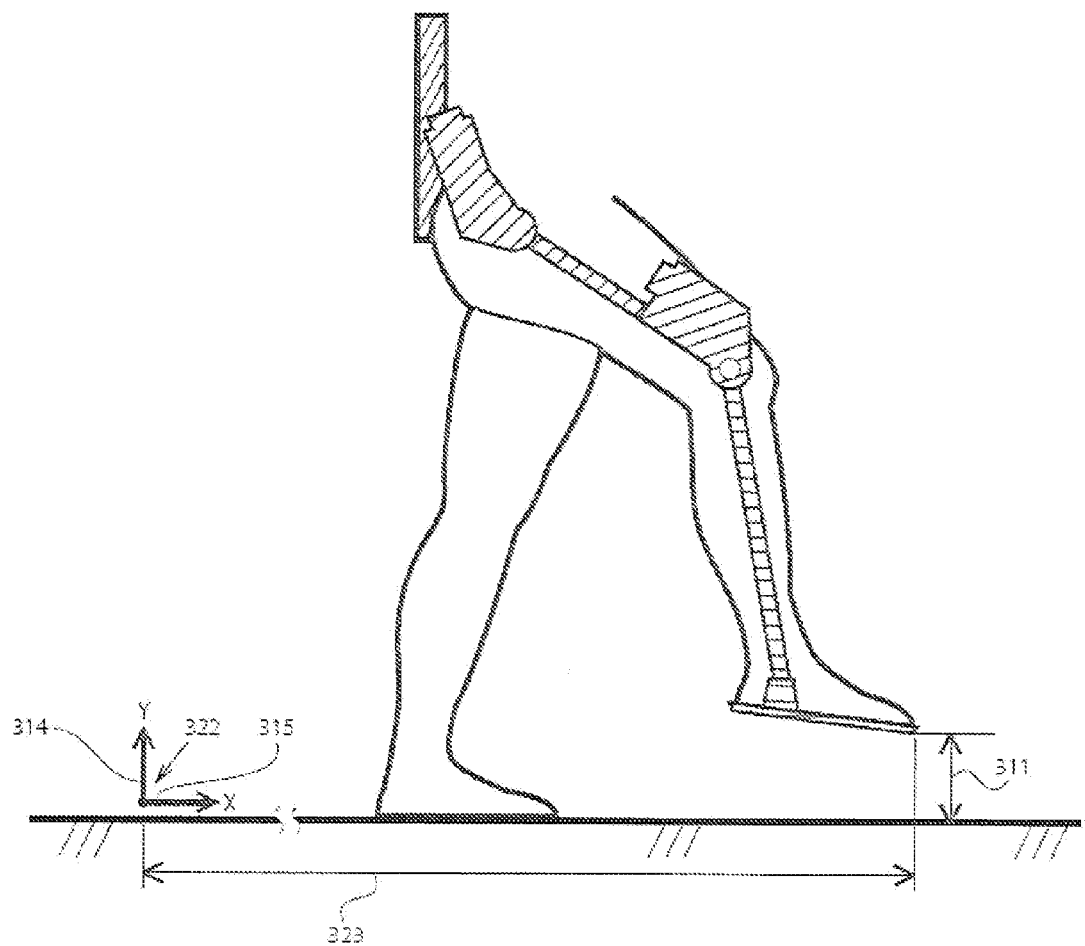
FIG. 38 is a schematic view of an exoskeleton system, similar to that of FIG. 36, in accordance with another embodiment of the invention.

In order to apply this technique, the Cartesian constraints must have a Cartesian coordinate reference. This reference establishes the origin for the Cartesian constraint being used to provide physical context for the constraint. In FIG. 36 the Cartesian coordinate reference 317 is defined as a point on the stance foot 319, indicating that all Cartesian constraints are in reference to the position of the stance foot. Another embodiment of this method could define the Cartesian constraints with respect to an external or global coordinate system 322. Such an embodiment defines the Cartesian coordinate reference as a fixed point in the surrounding environment of the device 309 as shown in FIG. 38 where coordinates 311 and 323 could be defined using a fixed positioning system in the room the device 309 is operating in. Many other embodiments exist that use a wide range of Cartesian coordinate references such as, but not limited to the following: the ground 313 potentially measured directly with a non-contact range sensor attached to the foot 301 or another part of the exoskeleton, a point on the stance leg 318 either on or off the ground 313, or a point on the torso 320.

Figure 39:
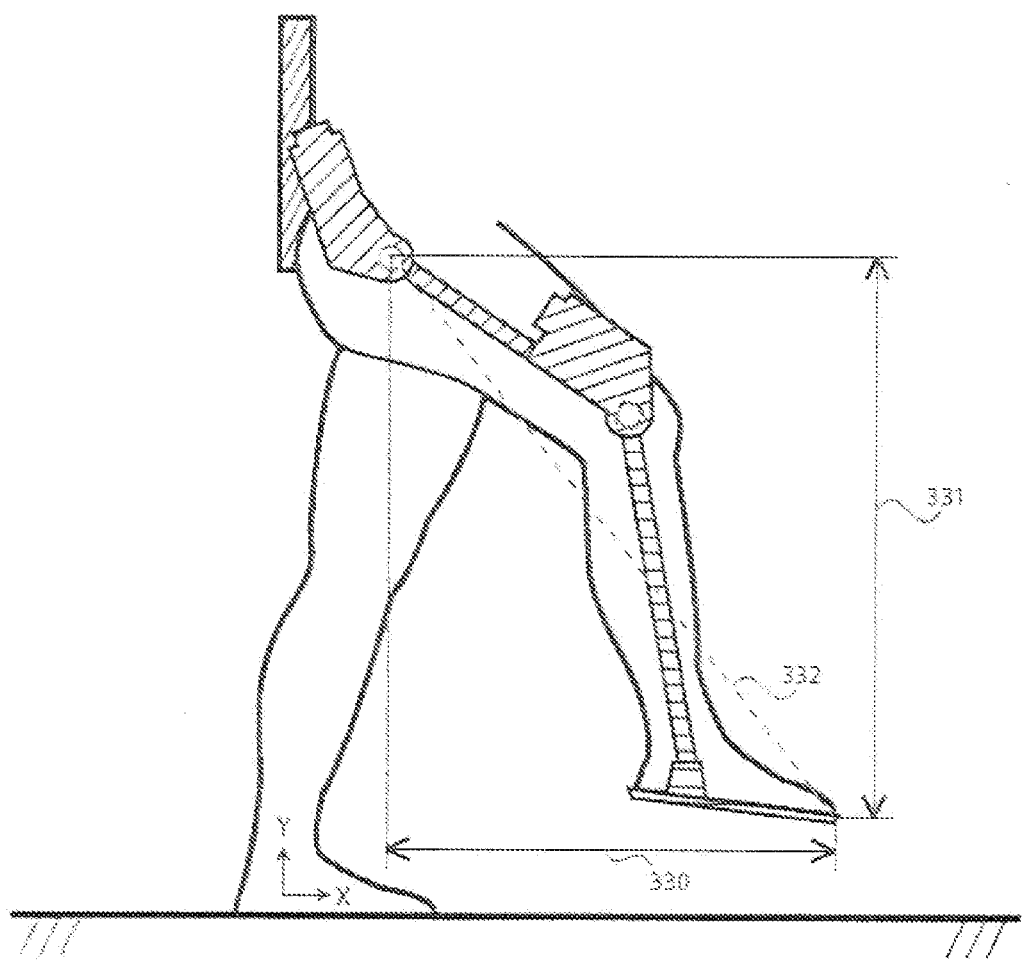
FIG. 39 illustrates an exemplary trajectory operation for the exoskeleton system of FIG. 38.

Additional embodiments can also use Cartesian constraints that are not defined strictly in the horizontal 315 or vertical axis 314 but rather are defined as fixing some combination of them both. An example is shown in FIG. 39 where horizontal dimension 330 and vertical dimension 331 are controlled such that there is a fixed ratio between them which will result in the toe remaining on the dotted path 332. Combining this path constraint with a knee angle 312 trajectory will provide two constraints to allow for calculating the remaining swing leg joint angle that meets both constraints. This of course, is just one example of an almost infinite number of relationships that could be defined.

Figures 40A, 40B:
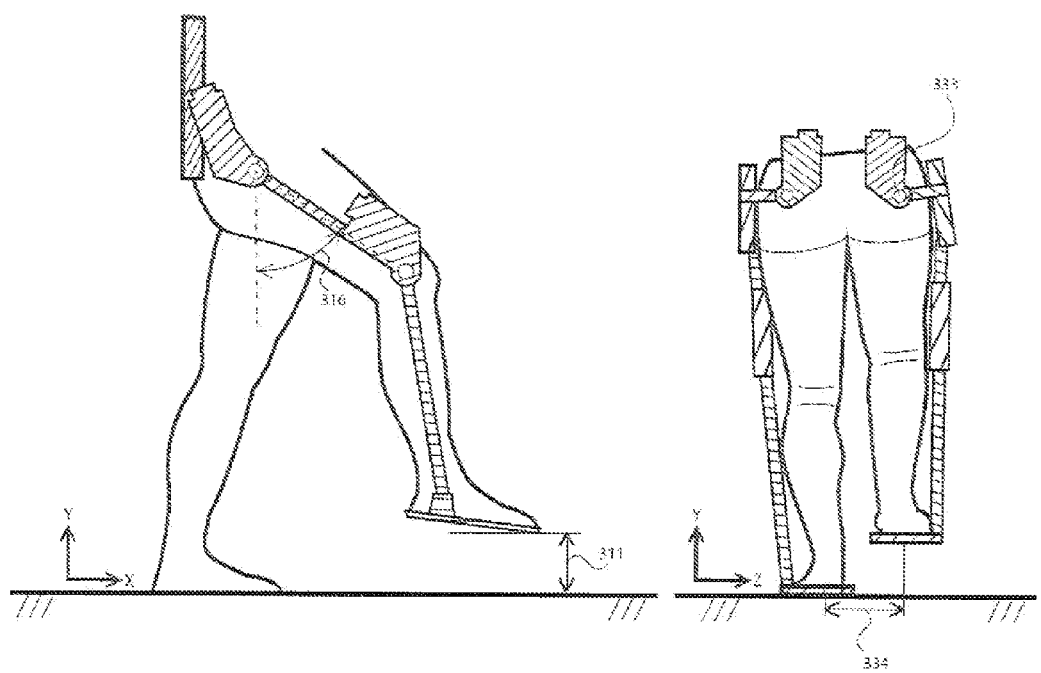
FIGS. 40A and 40B illustrates side and rear views respectively, of another embodiment of the exoskeleton system, of the invention.

This invention can also extend to embodiments that use more or less than two constraints as long as one of those constraints is a Cartesian constraint. For example, the same method extends to a system that only has one computer controlled joint such as a knee 306 that is attempting to meet the single constraint of maintaining a clearance height 311 of the ground contact point. In this scenario it is necessary that the system has at least as many controllable degrees of freedom as the number of desired constraints they intend to satisfy. As a result, a system with only a controllable knee joint 306 cannot meet both a desired ground contact X 323 and Y 311 constraint because the geometry of the system provides no solvable set to guarantee meeting two constraints on the system. Similarly, the method can apply to systems with more than two constraints as long as there are more controllable degrees of freedom than the number of desired constraints. One such embodiment is a system that has controlled hip 308 and knee joint 306 in the sagittal plane and a controlled hip joint 333 in the frontal plane that seeks to meet three constraints. An example set of constraints for this system could be the ground contact Y coordinate 311, the hip angle 316 and the frontal plane excursion of the ground contact point 334 as shown in FIG. 40. These constraints are a valid set of constraints because they are three independent constraints which fully define the desired geometry of the system.

Another set of embodiments of this invention coordinates the motion of the hip 308 and knee 306 to accomplish a desired foot motion where the constraints change throughout the step. One method for moving between constraints and determining the phase of the swing state is using a finite state machine. These embodiments allow the system to complete a different step depending on how the foot is progressing through the step. These methods can use all of the same constraints presented in the previous embodiments of the invention. In typical applications, the constraints applied when used in a state machine embodiment are in the form of constraint trajectories that are defined with respect to time through the step.

Figure 41:
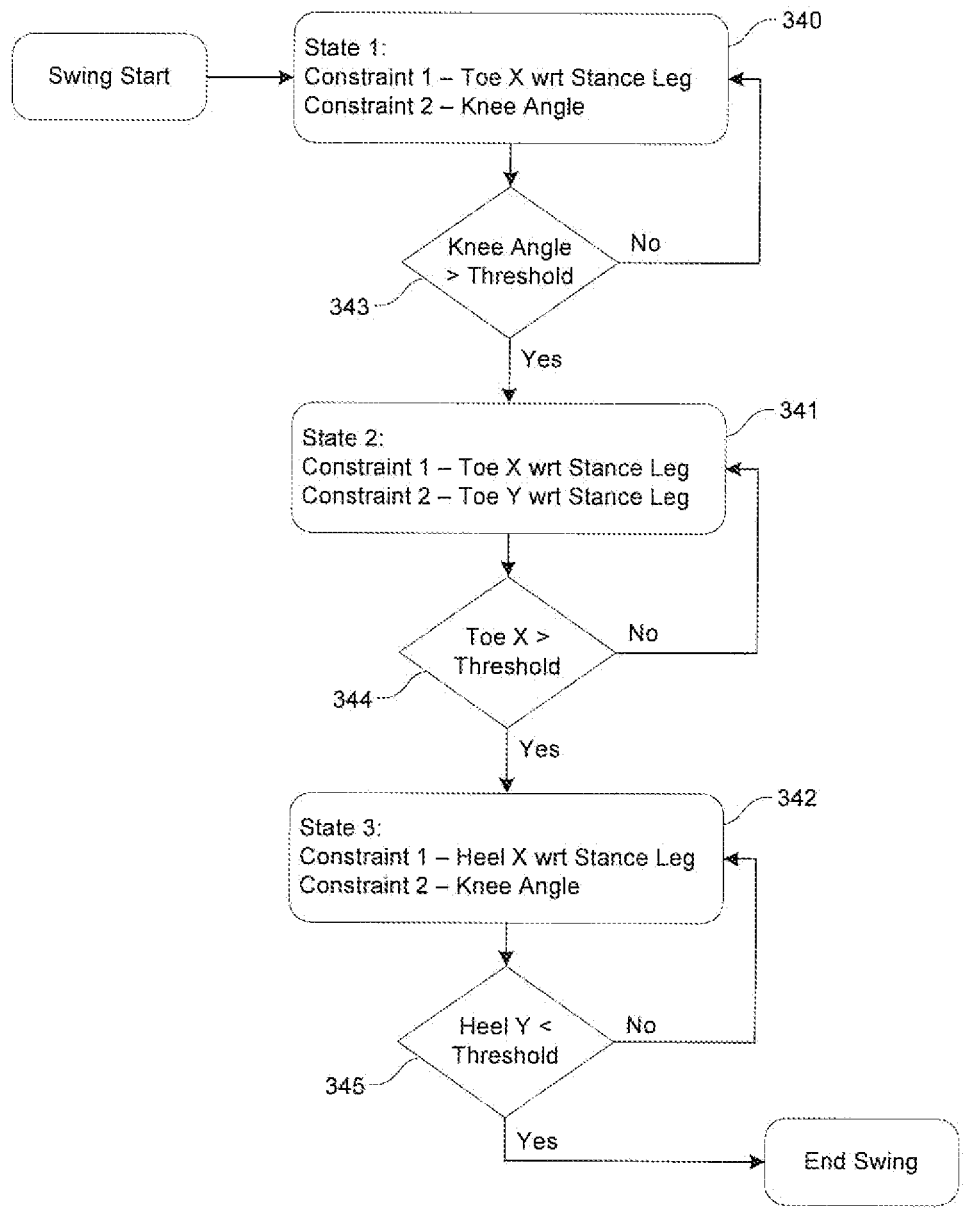
FIG. 41 is a flow chart for a simple finite state machine employed with the exoskeleton system of the invention.
Figure 42:
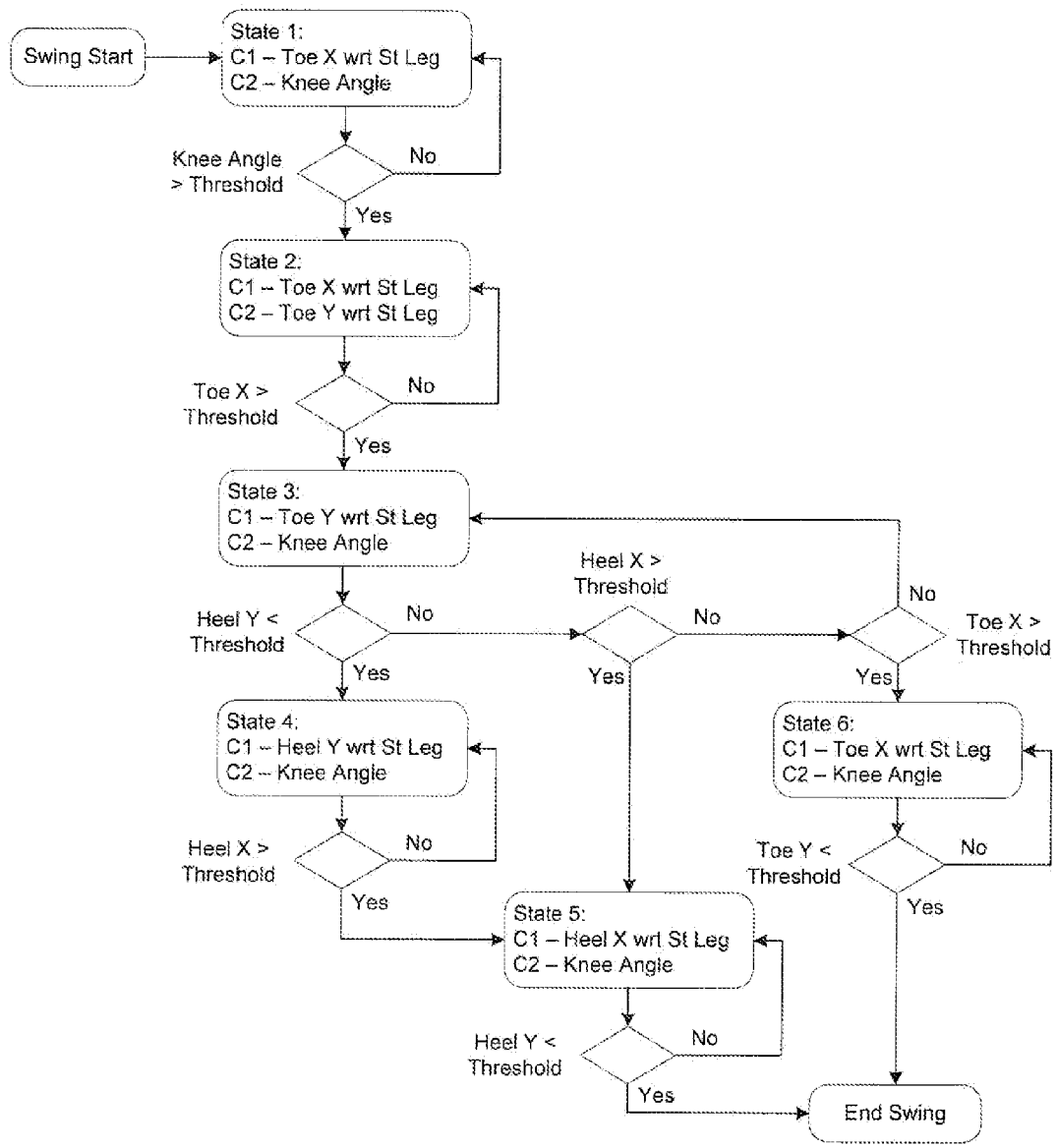
FIG. 42 is a modified, more complex, version of a flow chart for use in connection with, the invention.

In one embodiment, the system uses a simple finite state machine to define the states of the swing based on their differing constraints as shown in FIG. 41. In the first state 340, the swing leg 310 is intended to buckle and prepare to swing through. This can be defined with constraints of the toe X coordinate 323 relative to a point on the stance leg 318 and the swing knee angle 312 trajectory. The transition to the next state 343 can be defined in many ways, but in this example the transition is happening at a predefined knee angle 312 threshold. In the second state 341, the swing leg 310 progresses the foot 301 through the minimum clearance stage. This motion can be defined using constraints of the toe X coordinate 323 and the toe Y coordinate 311 relative to a point on the stance leg 318 (a simple path in x, y space). After the minimum clearance stage is complete, this state transitions to the next state 344 based on a set toe X coordinate 323 relative to a point on the stance leg 318. In the third state 345, the swing leg 310 prepares for heel strike using constraints on the heel X coordinate relative to a point on the stance leg and the knee angle 312 trajectory. This can be expanded to a more complex embodiment of the invention that incorporates more states to better isolate the desired behavior of the foot 301 at any one time as shown in FIG. 42.

Although described with reference to preferred embodiments of the invention, it should be understood that various changes and/or modifications can be made to the invention without departing from the spirit thereof. In general, the invention should only be limited by the scope of the claims.

The invention claimed is:

1. A method of controlling a powered lower extremity orthotic having at least one leg with at least two actuators configured to be controlled by a signal processor and coupled to the lower limb of a person, comprising:
   controlling a trajectory of a reference point on the at least one leg of said orthotic when the at least one leg is not touching a ground surface to follow a predetermined trajectory that is defined by at least one Cartesian coordinate; and
   switching coordinates used to define said trajectory within a single gait cycle.

2. The method of claim 1 wherein the Cartesian coordinate is measured in a horizontal axis.

3. The method of claim 1 wherein the Cartesian coordinate is measured in a vertical axis.

4. The method of claim 1 wherein the Cartesian coordinate is measured in an axis that is not purely horizontal or vertical.

5. The method of claim 1 wherein the trajectory is defined by a vertical Cartesian coordinate and a knee angle coordinate.

6. The method of claim 1 wherein the trajectory is defined by a vertical Cartesian coordinate and a hip angle coordinate.

7. The method of claim 1 wherein the trajectory is defined by a horizontal Cartesian coordinate and a knee angle coordinate.

8. The method of claim 1 wherein the trajectory is defined by a horizontal Cartesian coordinate and a hip angle coordinate.

9. The method of claim 1 further comprising: measuring the trajectory of said reference point with respect to a torso link configured to couple said orthotic to a pelvis or torso region of the person.

10. The method of claim 1 wherein the trajectory of said reference point is measured with respect to an absolute frame of reference.

11. The method of claim 1 wherein the trajectory of said reference point is measured with respect to the ground.

12. The method of claim 11 further comprising: estimating a position of said reference point from an orientation of a second leg of the orthotic that is in contact with the ground surface.

13. The method of claim 11 directly measuring a height of said reference point from the ground surface with a non-contact sensor.

14. The method of claim 1 further including maintaining a state machine to switch between the coordinates.

15. An artificial leg device, configured to be coupled to the lower limb of a person, comprising:
- an artificial foot having a toe and a heel;
- a shank link coupled to the artificial foot;
- a thigh link configured to be attached to a person;
- a knee mechanism interconnecting said thigh link and said shank link, said knee mechanism allowing flexion and extension movements of said thigh link and said shank link relative to each other;
- a torque generator configured to generate torque between said shank link and said thigh link;
- a knee angle sensor creating a knee angle signal representing an angle between said shank link and said thigh link;
- a stance sensor configured to identify which part of said artificial foot is in contact with a ground surface;
- a power source configured to provide electric power; and
- a signal processor connected to the power source, the torque generator, the knee angle sensor and the stance sensor, wherein said signal processor receives signals from the knee and stance sensors, determines that the artificial foot is in a swing state and controls the angle between said shank link and said thigh link through the torque generator such that said artificial foot follows a predetermined trajectory.

16. The artificial leg device of claim 15, wherein the predetermined trajectory is generally parallel to the ground.

17. An artificial leg device, configured to be coupled to the lower limb of a person, comprising:
- a shank link configured to be attached to a person;
- a thigh link configured to be attached to a person;
- a torso link configured to be attached to a person;
- a knee mechanism interconnecting said thigh link and said shank link, said knee mechanism allowing flexion and extension movements of said thigh link and said shank link relative to each other;
- a knee torque generator configured to generate torque between said shank link and said thigh link;
- a knee angle sensor creating a knee angle signal representing an angle between said shank link and said thigh link;
- a hip mechanism interconnecting said thigh link and said torso link, said hip mechanism allowing flexion and extension movements of said thigh link and said torso link relative to each other;
- a hip torque generator configured to generate torque between said shank link and said torso link;
- a hip angle sensor creating a hip angle signal representing an angle between said torso link and said thigh link;
- a power source configured to provide electric power; and
- a signal processor connected to the power source, the knee torque generator, the hip torque generator, the knee angle sensor and the hip angle sensor, wherein said signal processor receives signals from the knee and hip sensors, and controls the angles between said shank link and said thigh link and between said thigh link and said torso link through the knee torque and hip torque generators respectively such that a reference point on the artificial leg device follows a predetermined trajectory that is defined by at least one Cartesian coordinate.

18. The artificial leg device of claim 17, wherein the Cartesian coordinate is the height of the reference point from a ground surface.

19. An artificial leg device, configured to be coupled to the lower limb of a person, comprising:
- an artificial foot having a toe and a heel;
- a shank link coupled to the artificial foot;
- a thigh link;
- a torso link configured to be attached to the person;
- a knee mechanism interconnecting said thigh link and said shank link, said knee mechanism allowing flexion and extension movements of said thigh link and said shank link relative to each other;
- a knee torque generator configured to generate torque between said shank link and said thigh link;
- a knee angle sensor creating a knee angle signal representing an angle between said shank link and said thigh link;
- a hip mechanism interconnecting said torso link and said thigh link, said hip mechanism allowing flexion and extension movements of said torso link and said thigh link relative to each other;
- a hip torque generator configured to generate torque between said thigh link and said torso link;
- a hip angle sensor creating a hip angle signal representing an angle between said thigh link and said torso link;
- a stance sensor configured to identify which part of said artificial foot is in contact with a ground surface;
- a power source configured to provide electric power; and
- a signal processor connected to the power source, the knee torque generator, the hip torque generator, and each of the knee angle, hip angle and stance sensors, wherein said signal processor receives signals from the knee, hip and stance sensors, determines that the artificial leg is in a swing state and controls the angles between said shank link and said thigh link and between the thigh link and the torso link through the knee and hip torque generators respectively such that said artificial foot follows a predetermined trajectory.

20. The artificial leg device of claim 19, wherein the predetermined trajectory is generally parallel to the ground surface.

* * * * *